United States Patent [19]

Barnes et al.

[11] Patent Number: 4,509,526

[45] Date of Patent: Apr. 9, 1985

[54] METHOD AND SYSTEM FOR NON-INVASIVE ULTRASOUND DOPPLER CARDIAC OUTPUT MEASUREMENT

[75] Inventors: Stephen R. Barnes; Gary L. Tarbox, both of Seattle; Lee L. Huntsman, Bainbridge Island; Barry D. McLaren, Auburn, all of Wash.

[73] Assignee: Lawrence Medical Systems, Inc., Redmond, Wash.

[21] Appl. No.: 464,965

[22] Filed: Feb. 8, 1983

[51] Int. Cl.³ .............................................. A61B 10/00
[52] U.S. Cl. .................................... 128/663; 128/713
[58] Field of Search .................. 128/663, 661, 713

[56] References Cited

U.S. PATENT DOCUMENTS

| | | | |
|---|---|---|---|
| 3,498,290 | 3/1970 | Shaw et al. | 128/663 |
| 4,137,910 | 2/1979 | Murphy | 128/713 X |
| 4,257,278 | 3/1981 | Papadofrougskis et al. | 128/663 X |
| 4,370,985 | 1/1983 | Takeichi et al. | 128/663 |

Primary Examiner—Kyle L. Howell
Assistant Examiner—Francis J. Jaworski
Attorney, Agent, or Firm—Hughes, Barnard & Cassidy

[57] ABSTRACT

A method and system for the noninvasive measurement of cardiac output of a mammalian patient on a real time, beat-by-beat basis as a combined function of the cross-sectional area of the ascending aorta and the systolic velocity of blood flow therethrough is comprised of the steps of and apparatus for pulsedly insonifying the ascending aorta of the patient with repetitive, intermittent ultrasonic energy propagating through the patient's cardiac window; receiving pulses of ultrasonic energy reflected from the anatomical structure within the first insonification zone, including energy reflected from the aortic walls and characteristic of the dimensional separation thereof; developing an aortic diameter signal indicative of dimensional separation; computing the cross-sectional area of the ascending aorta therefrom; then continuously insonifying the ascending aorta with uninterrupted ultrasonic energy; receiving a Doppler-shifted ultrasonic energy signal reflected from pulsatile blood flow through the ascending aorta, and characteristic of systolic velocity of blood flow; subjecting the systolic velocity signal to a frequency spectrum analysis at a predetermined signal sampling rate to yield a velocity component profile signal; integrating the velocity component profile signal over time; computing systolic volume as a combined function of cross-sectional area and the systolic velocity integral for each of n cardiac cycles; and, computing cardiac output as the time-averaged sum of systolic volumes for the n periods.

23 Claims, 39 Drawing Figures

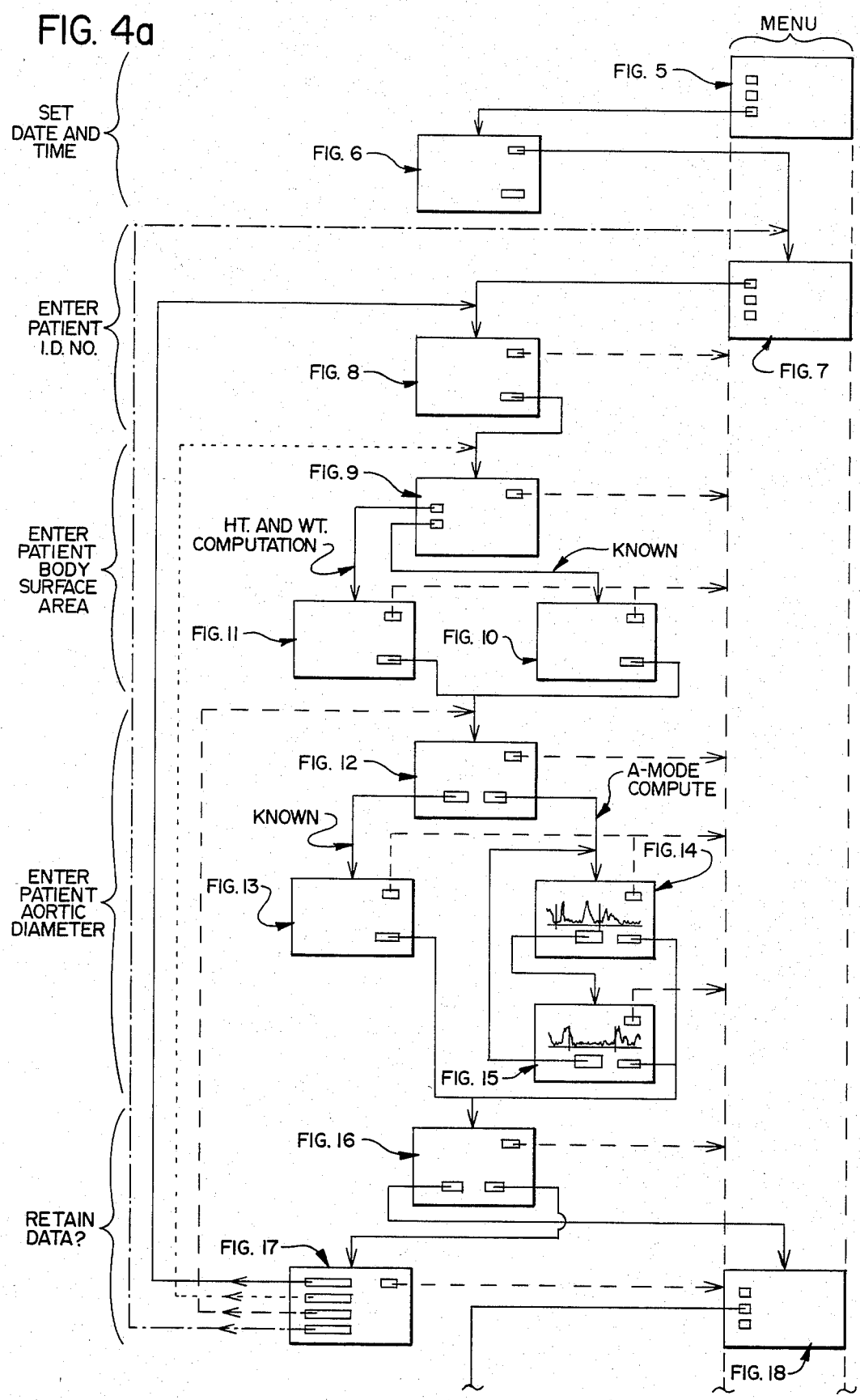

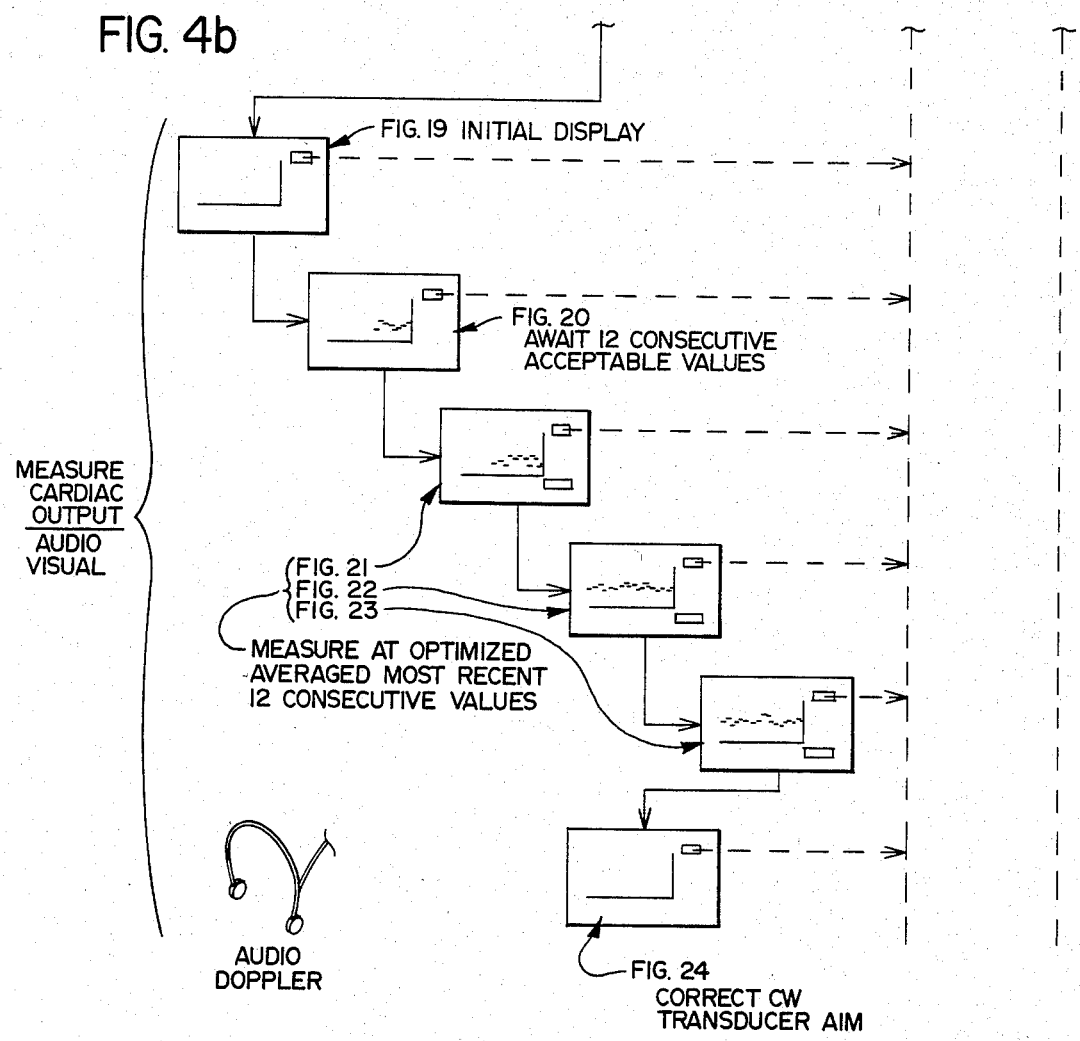

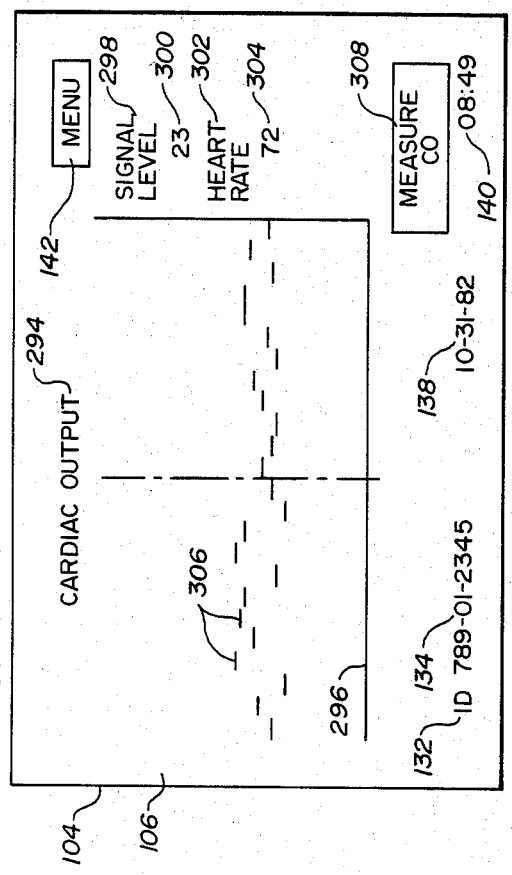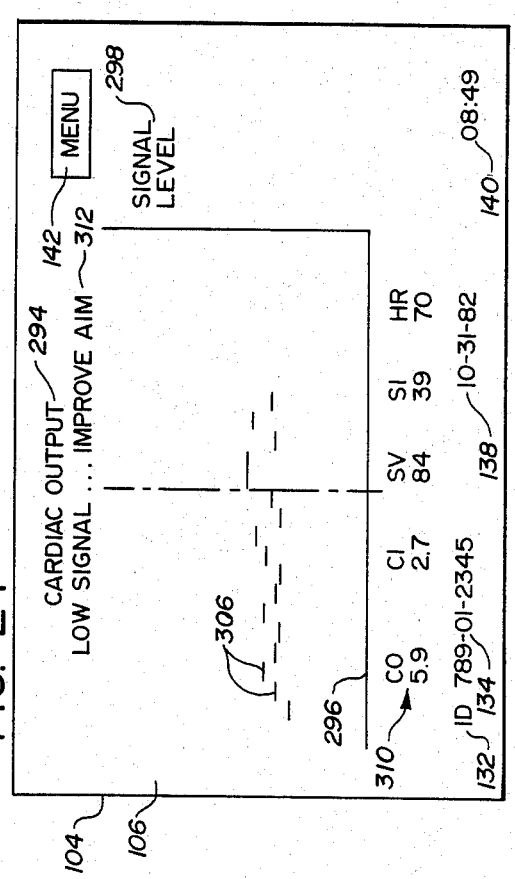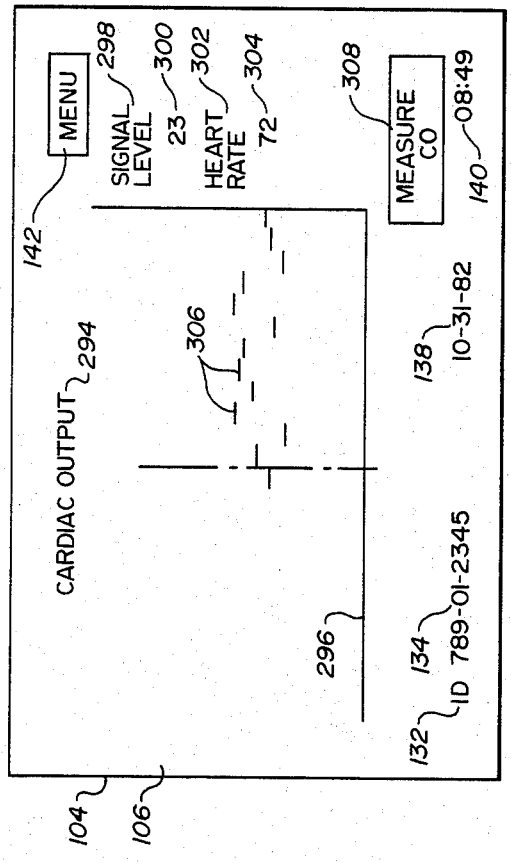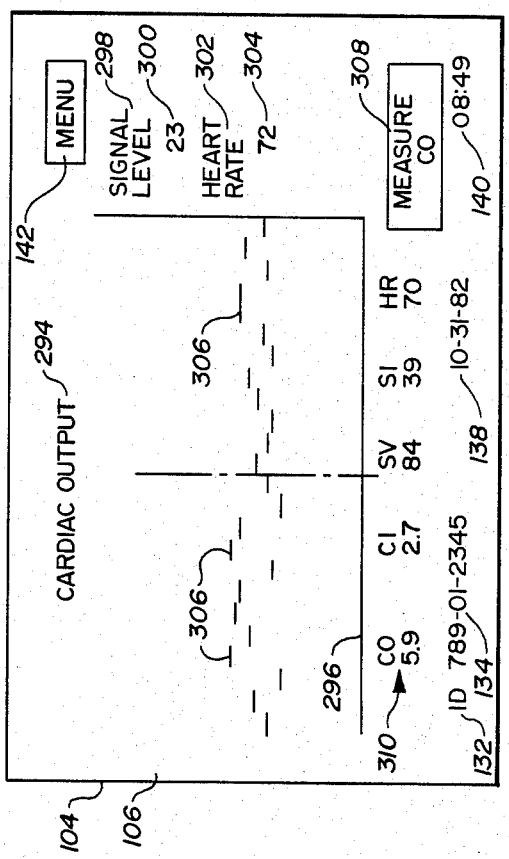

METHOD AND SYSTEM FOR NON-INVASIVE ULTRASOUND DOPPLER CARDIAC OUTPUT MEASUREMENT

BACKGROUND OF THE INVENTION

The present invention relates, generally, to methods and means for measuring the cardiac output of a mammalian patient, more especially to noninvasive methods and means for measuring the cardiac output of a human patient, and most particularly to a dual modality insonification technique for ascertaining the cross-sectional area of the patient's ascending aorta and the systolic velocity profile of blood flow therethrough allowing for a determination of cardiac output, cardiac index, stroke volume and stroke index, amongst other physiological parameters.

SUMMARY OF THE INVENTION

The present invention advantageously provides a simple yet highly efficient method and means for carrying out the measurement of cardiac output of a mammalian patient, and particularly a human patient on a real time, beat-by-beat basis. The method and means of conducting such measurement in accordance with the present invention are especially desirable for facilitating direct operator interaction with the apparatus over the course of the measurement protocol via an interactive visual display which instructs the operator at each step of the sequence and responds to an election of operator options with certain failsafe features guarding against the entry of invalid data and prompting the entry of maximized physiological characteristics of the patient under examination. Still a further advantage of the present invention is the selective, specific use of dual modality insonification with an eye toward employing an ultrasound mode best suited for the measurement task at hand. A related benefit is the facility with which the operator may interact with the system to achieve reliable, repetitive results without requiring extensive training. As respects the system itself, the same provides the benefits of microprocessor control for fast data computation without the need to resort to elaborate hardware or software.

The foregoing, and other, advantages and benefits are realized in a method wherein the diameter of a patient's ascending aorta is provided as an input to the system, either as a known parameter or as measured via A-mode (pulsed) insonification techniques, and the cross-sectional area computed based on a model of the aorta as a right circular cylinder (hence, area as that of a circle); followed by a continuous wave insonification procedure to measure systolic velocity of blood flow through the ascending aorta using Doppler techniques. The variable parameters of area and flow rate provide the basis for determining cardiac output; rationalized to cardiac index as the ratio of cardiac output to the patient's body surface area. The system for implementing that method is comprised of circuitry for generating the pulsed ultrasonic energy, detecting reflected returns and processing same, cooperating with circuitry for producing continuous wave ultrasonic energy and detecting Doppler shifted returns for processing via spectrum analysis; both integrated through a visual or graphic display having a touch-sensitive overlay for direct operator interaction with the system.

A preferred method for the noninvasive measurement of cardiac output is comprised of the steps of pulsedly insonifying the ascending aorta of the patient with repetitive, intermittent ultrasonic energy propagating along a line generally transverse with respect to the axis of the ascending aorta from a position through the cardiac window of the patient to define a first insonification zone enveloping the aortic region; receiving pulses of ultrasonic energy reflected from the anatomical structure within the first insonification zone, including energy reflected from the anterior and posterior walls of the ascending aorta characteristic of the separation thereof along the transverse line of propagation therethrough; discriminating the pulses of received ultrasonic energy to detect the transverse dimension of the ascending aorta between the anterior and posterior walls; developing an aortic diameter signal proportional to and indicative of the transverse separation between walls; computing the cross-sectional area of the ascending aorta in the plane of the transverse line of propagation of pulsed energy, most preferably modeling the aorta throughout the procedure as a right circular cylinder to facilitate the ease of computation—here the area of a circle; thence continuously insonifying the ascending aorta with uninterrupted ultrasonic energy propagating along a line generally axial with respect thereto from a position within the patient's suprasternal notch to define a second insonification zone within the aortic region; receiving Doppler-shifted ultrasonic energy reflected from pulsatile blood flow through the ascending aorta, and principally the red blood cells thereof, frequency shifted from the frequency of the transmitted ultrasonic energy by values characteristic of systolic flow velocity; developing a systolic velocity energy signal as a time domain function proportional to and indicative of the systolic velocity of blood flow; subjecting that systolic velocity energy signal to frequency spectrum analysis, and most preferably to fast Fourier transform analysis, at a predetermined signal sampling rate to develop a velocity component profile signal as a frequency domain function characteristic of the composite of peak frequency components in the sampled signal; integrating the velocity component profile signal over time for each period of pulsatile flow to calculate a systolic velocity integral; computing stroke volume as a combined function of the cross-sectional area of the aorta and the systolic velocity integral for each of n periods; and computing cardiac output as the time-averaged sum of stroke volumes for the n periods. Each stage of the overall protocol is accompanied by a sequence of instructional steps to be followed by the operator, appearing on a cathode ray tube display (CRT) having associated therewith a touch-sensitive overlay facilitating direct operator interaction with the system. The combination of the CRT display and the touch-sensitive overlay provides the operator with a graphic indication of specific optional steps throughout the measurement sequence accompanied by active field areas allowing a given one or more options to be elected simply upon a manual touch of the display. Data is introduced to the system via the display upon a controlled presentation of active areas in the form of an alphanumeric keyboard to facilitate the use of the system by a wide range of individuals having equally diverse backgrounds. Known physiological characteristics of the patient under examination, for example aortic diameter and/or body surface area, may simply be introduced to the system. Otherwise, the system will accept raw data, for example body height and weight to compute the desired characteristic, i.e., body surface area; or the system may be keyed to present a visual display facilitating the measurement of the desired characteristic, e.g., aortic diameter. Within operational limits, the system will insist upon the entry of required data, will limit the entry of certain data to values within statistically anticipated ranges, and will prompt the operator to maximize the accuracy of technique in measuring unknown parameters.

Further along these summary lines of system control for maximized efficiency and reliability, the process of the present invention most preferably includes a self-contained procedure for enhanced data processing, particularly in respect of the frequency spectrum analysis of Doppler-shifted data. This procedure is comprised of the steps of establishing a plurality of signal sampling rates based upon corresponding ranges for statistically anticipated systolic velocities for the patient under examination; selecting high and low threshold values for these separate velocity ranges; monitoring systolic velocity to determine its value within a given one of the ranges as measured with reference to the selected threshold values; and, adjusting the signal sampling rate for data analysis to a predetermined one of the plurality of sampling rates corresponding to the systolic velocity within the threshold values for that range. For example, in the most preferred embodiment of the present invention, three anticipated velocity ranges are established— viz., 0–82 cm/s, 0–165 cm/s, and 0–330 cm/s—with correlative sampling rates for the spectrum analysis. The system initially processes data at the first sampling rate while monitoring the velocity signal. Upon the occurrence of systolic velocities in excess of the high threshold value for the first range, the system automatically adjusts the sampling rate to the second rate for further processing. Monitoring the velocities continues, now with reference to a high and low threshold value within the second range. Systolic velocities lower than the low threshold causes a downward adjustment to the first sampling rate, while velocities in excess of the high threshold for the second range adjusts the sampling rate to the third range. Should the third rate be selected, and subsequent monitoring reveals systolic velocities lower than a low threshold for that range, an adjustment in the sampling rate to the second rate is made. In this manner, processing of data is correlated with the appropriate velocity range, enhancing processing capabilities while simplifying system hardware and firmware.

In those situations where the operator has elected to measure aortic diameter, the visual display presents a graphic image showing returns detected upon reflection of pulsed ultrasonic energy from anatomical structure within the insonification zone (including returns from the anterior and posterior walls thereof), scaled to the propagation distance of the transmitted energy. The graphic display assists in proper positioning and manipulation of the pulse transducer to insure proper placement of the probe to direct the pulsed energy through the patient's cardiac window at an orientation generally transverse with respect to the ascending aorta. This is achieved by employing the highly characteristic returns from the aortic region, and particularly the leaflets of the aortic valve which provide a distinctive echo pattern observable by the operator on the visual display. Manipulation of the probe results in a corresponding alteration in the display to optimize the appearance of the signals and allow improved operator confidence in the proper position of the pulse transducer probe. Once that probe has properly been positioned, the operator may freeze the graphic image and, by way of moveable cursors operated through the touch-sensitive overlay, make a direct, scaled measurement of the aortic diameter. In this mode, the pulse-echo portion of the system serves principally to detect and present echo returns through generally conventional, digital raster scan circuitry for the CRT display while the overlay and coordinated control means serve to develop the aortic diameter signal as the scaled separation between moveable cursors manipulated by the operator.

In a generally like vein, the cardiac output data processed as aforesaid is presented on the visual display during the corresponding continuous wave measurement of systolic velocity. The display thereby provides the operator with direct visual indication of cardiac output and its changing rate from cardiac cycle to cycle; further providing a message to the operator when the signal level is too low, prompting manipulation for more accurate positioning of the transducer probe. In this continuous wave mode, the operator is also supplied with audio information indicative of systolic velocity; developed by mixing the Doppler-shift signal downward, preferably in two mixing stages, to yield an audio signal where frequency is directly proportional to velocity. Thus the operator may rely upon aural and/or visual means of perception during the diagnostic procedure.

The foregoing and other advantages of the present invention will become more apparent, and a fuller appreciation of its construction and methods of operation will be gained, upon an examination of the following detailed description of preferred embodiments, taken in conjunction with the figures of drawing, wherein:

DESCRIPTION OF THE DRAWINGS

FIGS. 4a and 4b, when disposed in adjacent top-to-bottom relation, comprise a block-and-line drawing here illustrating in time sequence the various graphic images that are presented sequentially on the screen of the cathode ray tube used with the present cardiac output monitoring system and, illustrating further, the process that would be employed by the medical practitioner to progressively step through a cardiac output monitoring operation that might vary from patient to patient dependent upon what data is known for each patient and what data must be calculated;

FIG. 5 is a view of the master image, herein referred to as the "Menu", which appears on the screen of the cardiac output monitoring system when the system is first powered up;

FIG. 21 is representative of the graphic image that appears on the face of the CRT screen at that point in time when at least twelve consecutive heartbeats have been detected having data within the acceptable range;

FIG. 22 is a portrayal of the graphic image that appears on the face of the CRT screen when the cardiac output monitoring apparatus of the present invention has detected twenty-four consecutive heartbeats each presenting data within acceptable limits;

FIG. 23 is a view similar to FIG. 22, but here illustrating the image appearing on the face of the CRT screen when the medical practitioner determines that optimum data values are being presented and enters those values by touching the active screen area labelled "Measure C0";

FIG. 24 is a view similar to FIG. 23, but here illustrating the CRT screen image that appears whenever the medical practitioner is not properly aiming the ultrasonic transducer axially along the ascending aorta— for example, after the cardiac output measurement has been completed and the transducer has been removed from the patient's suprasternal notch;

Figure 25A:
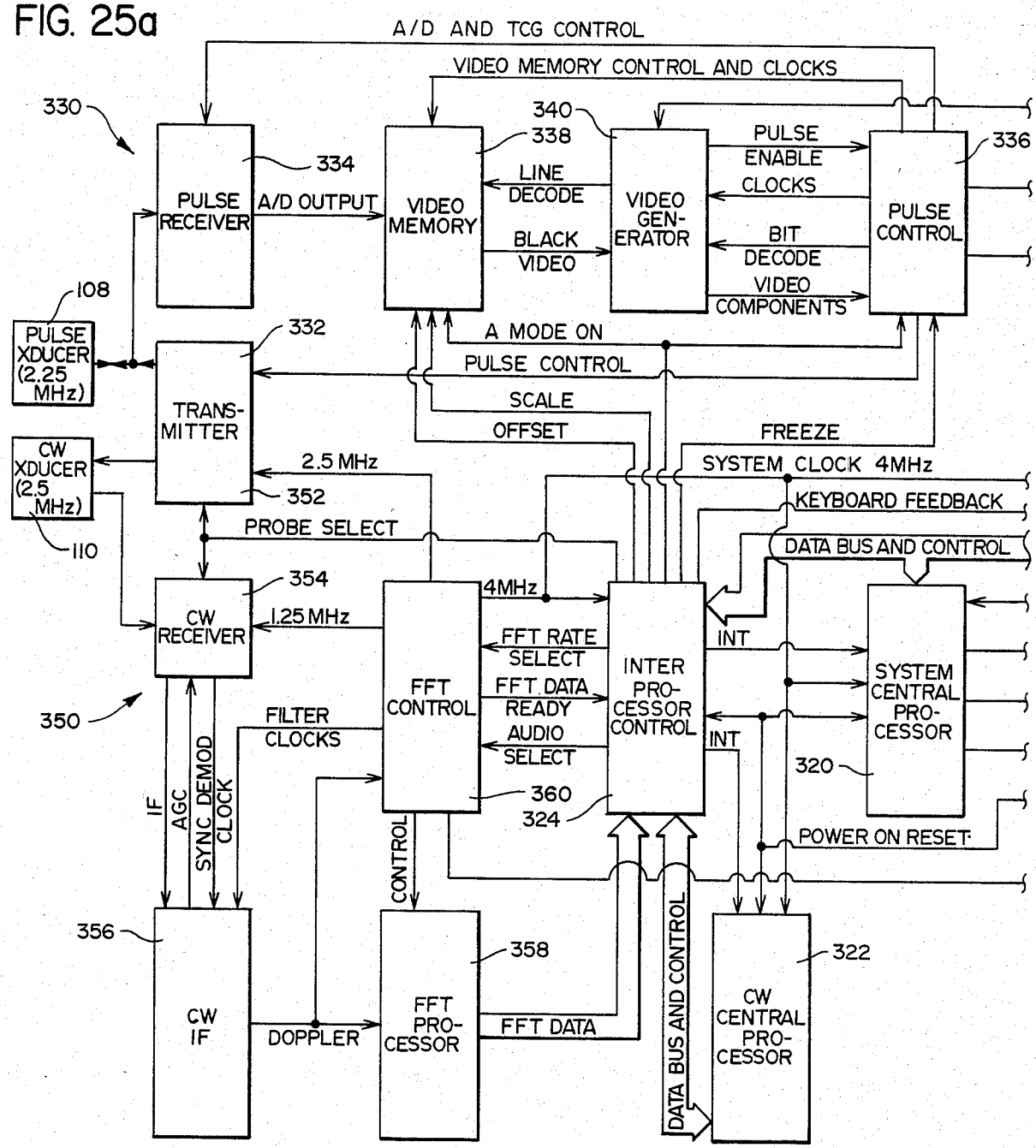
Figure 25B:
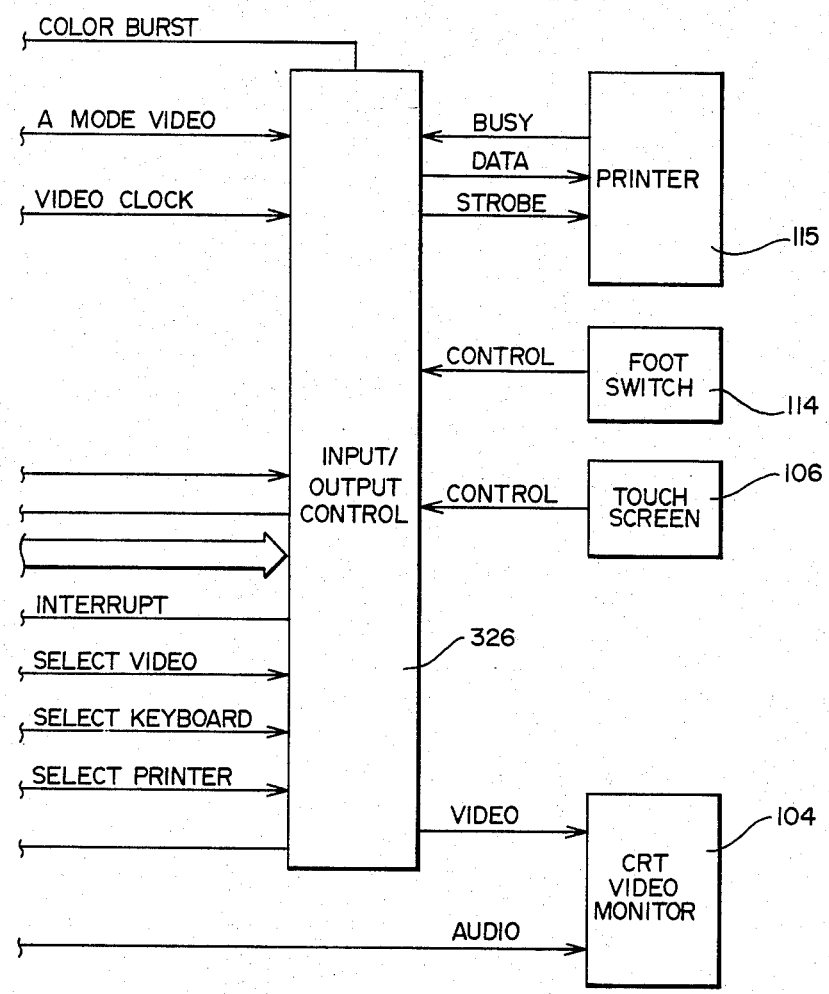
Figure 26:
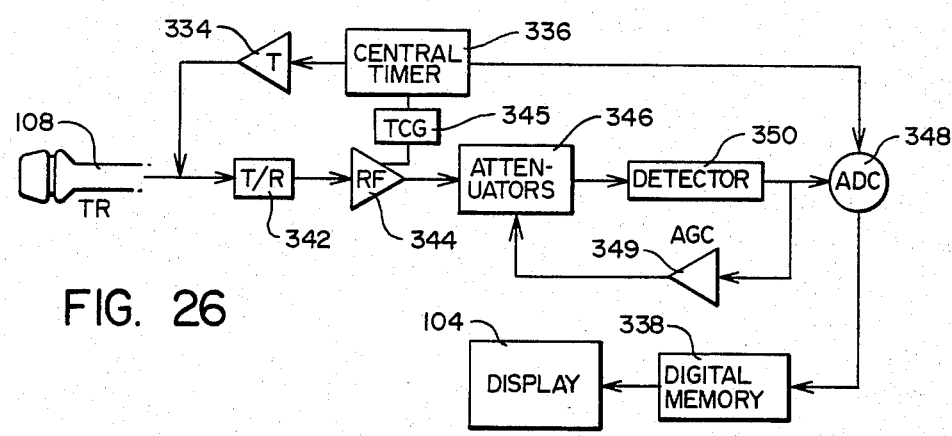
Figure 27:
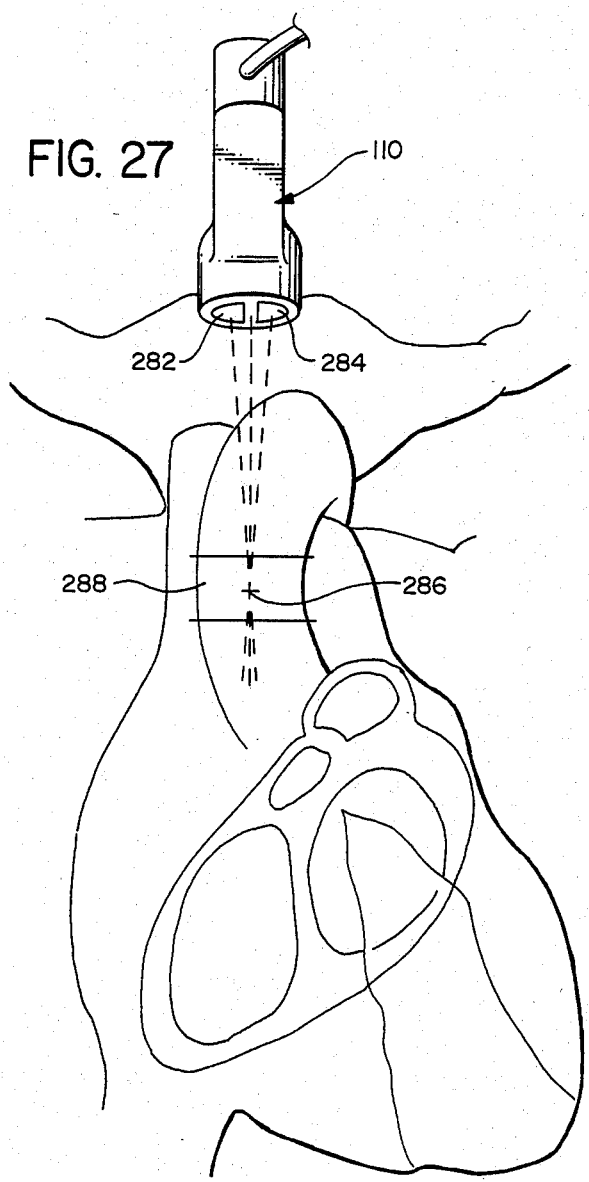
Figure 28:
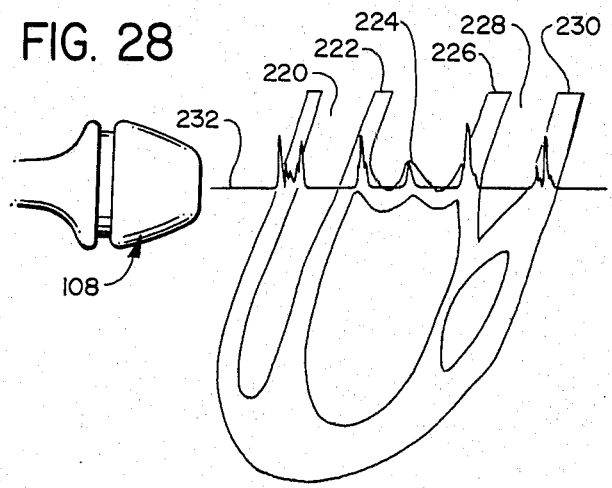
Figure 29:
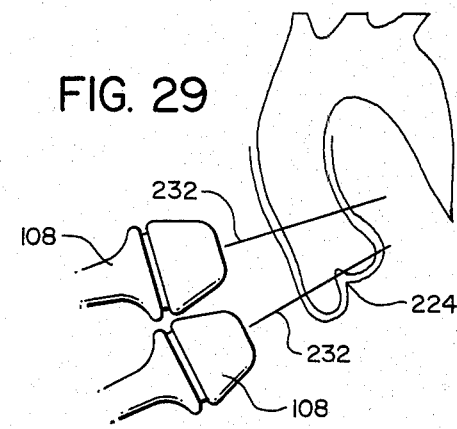
Figure 30A:
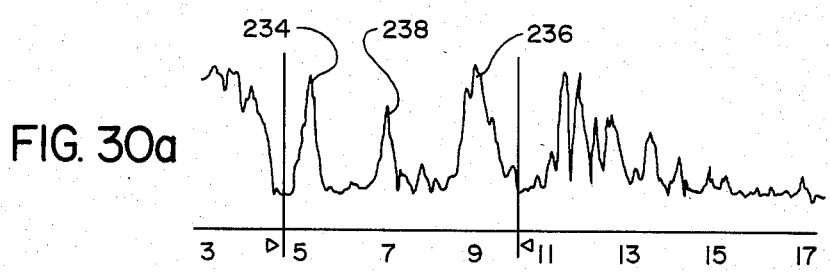
Figure 30B:
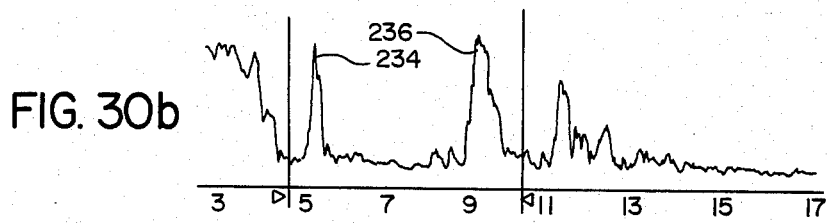
Figure 31:
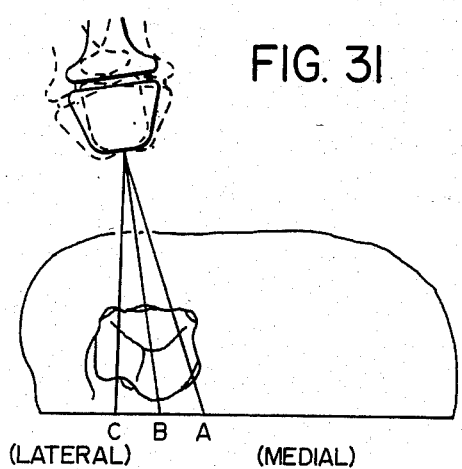
Figure 32A:
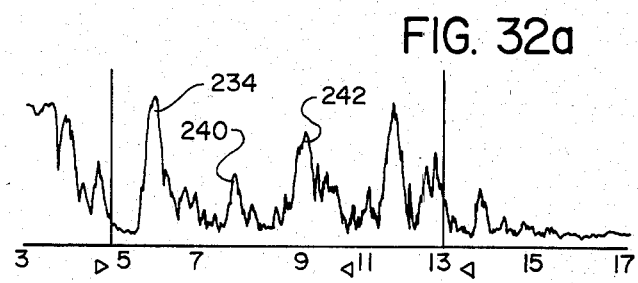
Figure 32B:
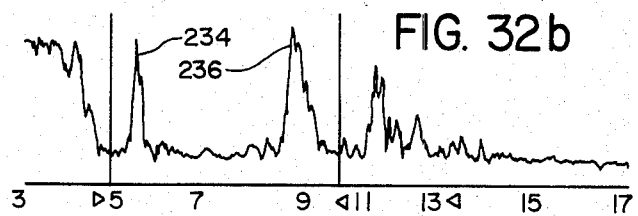
Figure 32C:
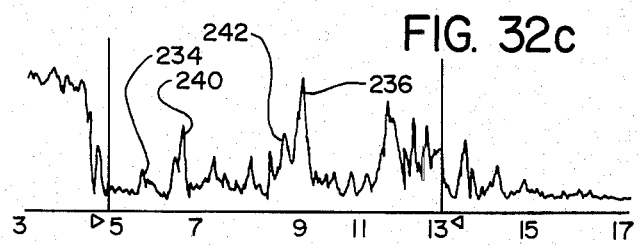
Figure 33:
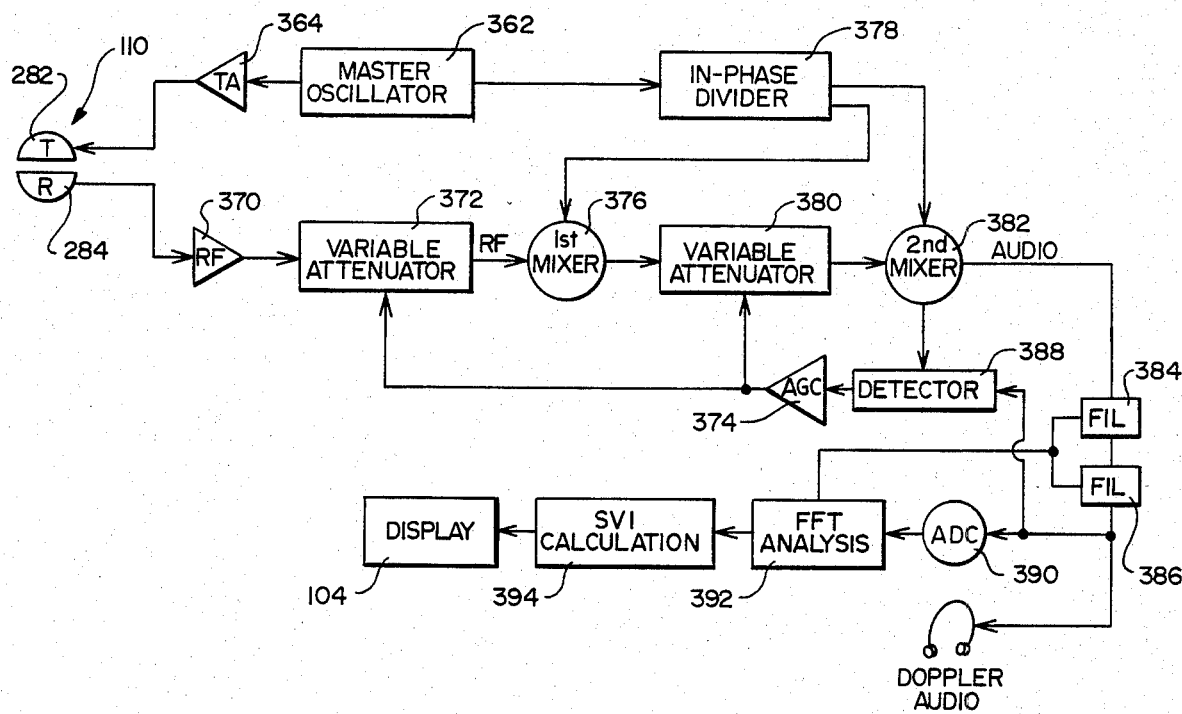
Figure 34:
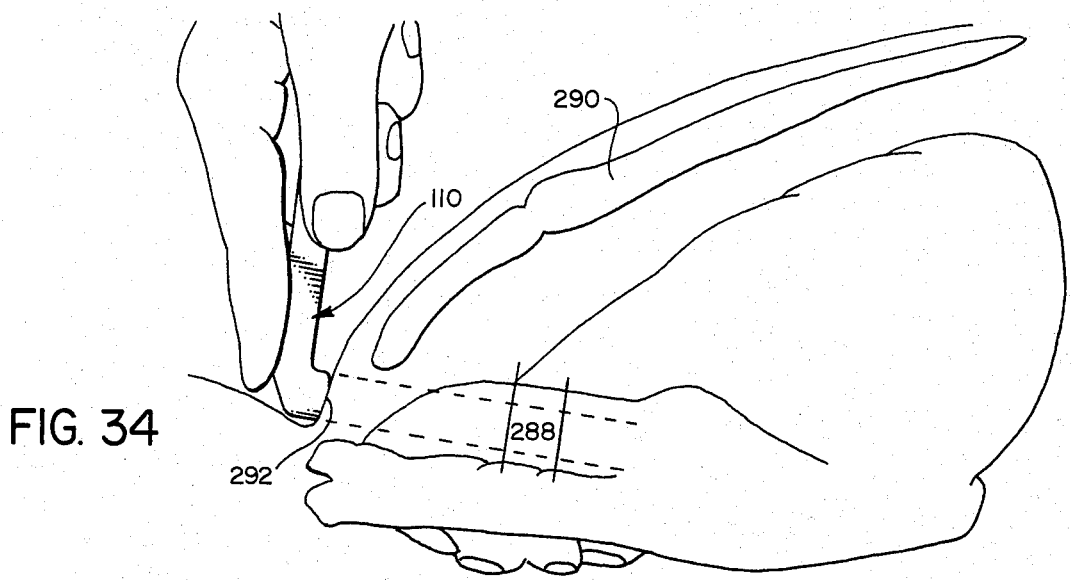

FIGS. 25a and 25b, when disposed in adjacent side-by-side relation, comprise a block diagram illustrating the various electronic components that might be employed in a cardiac output monitoring system made in accordance with the present invention;

FIG. 26 is a simplified block diagram here illustrative of the echo-ranging signal path associated with a pulse-type ultrasonic transducer utilized to measure a patient's aortic diameter;

FIG. 27 is a diagrammatic frontal elevational view illustrating generally a human heart and certain of the major arterial vessels, and particularly illustrating the relative positions of the patient's suprasternal notch and ascending aorta with a continuous wave ultrasonic transducer positioned in the suprasternal notch and directing a focused ultrasonic beam substantially axially along the ascending aorta;

FIG. 28 is a highly diagrammatic illustration of the various heart structures as detected by a pulse-type ultrasonic transducer which is directed through the cardiac window on the patient's chest and looking at the aortic root;

FIG. 29 is a highly diagrammatic side view illustrating both proper and improper positioning of a pulse-type transducer with respect to the patient's aorta;

FIG. 30A is a graphic view of the image which might appear on the face of the CRT screen in those instances where a pulse-type ultrasonic transducer is improperly positioned as shown in FIG. 29 so as to intercept the valve leaflets of the heart in the Sinus of Valsalva;

FIG. 30B is a view similar to that shown in FIG. 30A, but here illustrating the image that appears on the face of the CRT screen when the pulse-type transducer is properly positioned as shown in FIG. 29;

FIG. 31 is a highly diagrammatic top or plan view illustrating a patient's aorta looking axially downwardly along the aorta with a pulse-type transducer positioned properly in the solid line position and improperly in the two phantom line positions;

FIG. 32A is a view illustrating the graphic presentation that might appear on the face of a CRT screen in those instances where the pulse-type transducer is improperly positioned in FIG. 31 and the ultrasonic beam is too medial with respect to the axis of the ascending aorta;

FIG. 32B is a view similar to that shown in FIG. 32A, but here illustrating the image that might appear on the CRT screen when the pulse-type transducer is properly positioned in the solid line position shown in FIG. 31 with the beam cutting substantially diametrically through the ascending aorta;

FIG. 32C is a view similar to those shown in FIG. 32A and 32B, but here illustrating the image that might appear on the face of a CRT screen when the pulse-type transducer is improperly positioned as shown in FIG. 31 with the energy beam being directed too lateral with respect to the diameter of the aorta;

FIG. 33 is a simplified block diagram herein illustrating the continuous wave Doppler signal path resulting from echo signals reflected from the red blood cells moving vertically upward through the patient's ascending aorta; and, FIG. 34 is a highly diagrammatic side elevational view of the upper chest and lower neck portion of a patient in a supine position and illustrating particularly proper placement of the continuous wave ultrasonic transducer within the patient's suprasternal notch with a focused ultrasonic beam being directed substantially axially along the patient's ascending aorta which is here illustrated diagrammatically.

DETAILED DESCRIPTION OF THE INVENTION

The present invention relates, generally, to methods and means for measuring the cardiac output of a mammalian patient, more especially to noninvasive methods and means for measuring the cardiac output of a human patient, and most particularly to a dual modality insonification technique for ascertaining the cross-sectional area of the patient's ascending aorta and the systolic velocity profile of blood flow therethrough allowing for a calculation of cardiac output, cardiac index, stroke volume and stroke index, amongst other physiological parameters, on a real time, beat-by-beat basis. Accordingly, the present invention will now be described with reference to certain preferred embodiments within the aforementioned contexts; albeit, those skilled in the art will appreciate that such a description is meant to be exemplary only and should not be deemed limitative.

The present invention employs two different ultrasonic measurement modes to gather data used for determining stroke volume and cardiac output of the patient. The first is an echo-ranging mode to measure the diameter of the aorta; which involves placing an echo-transducer over the heart, obtaining a so-called "A-mode" image of the aorta on a visual display, and measuring the aortic diameter from the image. That measurement is then employed by an adaptive algorithm to compute aortic cross-sectional area, modeling the aortic structure as a right circular cylinder throughout the procedure for ease of computation with minimal sacrifice in accuracy. The second mode is a continuous wave mode to insonify the ascending aorta and detect Doppler-shift caused by moving red blood cells within it. This measurement is made by placing a Doppler ultrasound transducer in the suprasternal notch of the patient and aiming the transducer toward the ascending aorta. The returning signals are processed into Doppler-shift signals that are analyzed and converted into discrete frequency components by digital fast Fourier transform ("FFT"). Through Doppler computation, the Doppler-shift frequencies are converted to velocities, in turn employed to calculate a systolic velocity integral ("SVI"). Combining the SVI with aortic cross-sectional area yields the cardiac stroke volume on a beat-by-beat basis; summing stroke volumes over a predetermined number of consecutive beats and then dividing by the time duration thereof yields cardiac output. Cardiac output may then be normalized to cardiac index simply by ratioing cardiac output to the patient's body surface area. The foregoing protocol is carried out by and implemented in the system of the present invention as illustrated more particularly in the figures of drawing.

Figure 1:
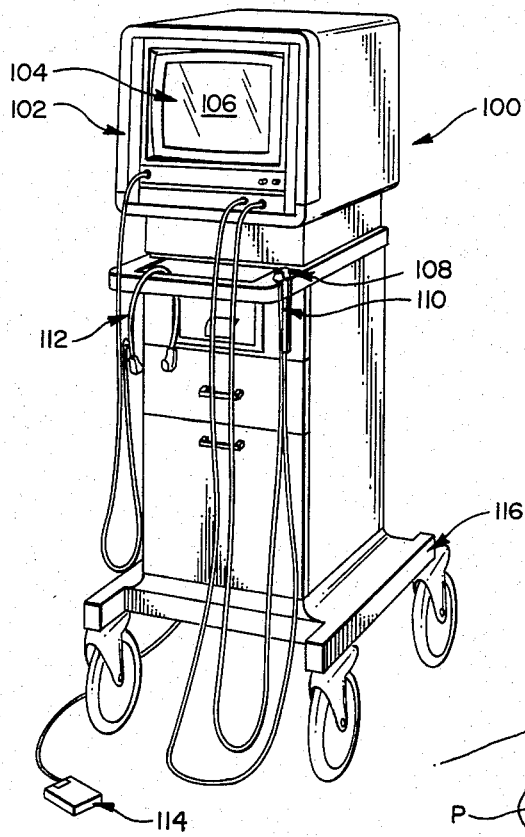
FIG. 1 is a perspective view illustrating an exemplary cardiac output monitoring system embodying features of the present invention, here mounted on casters so as to enhance the mobility of the system.
Figure 2:
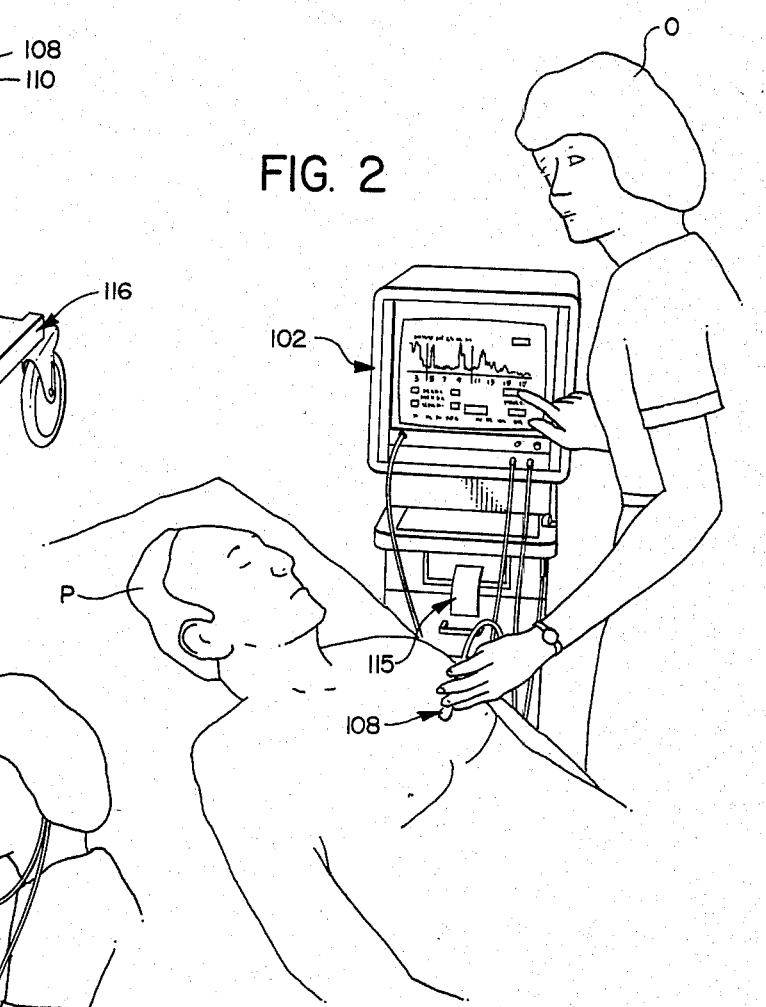
FIG. 2 is a perspective view here illustrating the cardiac output monitoring system shown in FIG. 1 in use, and wherein a suitable medical practitioner (for example, a doctor, nurse, technician or the like) has positioned a pulse-type ultrasonic transducer at the cardiac window between the second and fourth intercostal spaces of a patient's chest and with the medical practitioner's right index finger positioned to "freeze" the graphic image appearing on the screen of the cardiac output monitoring system, which image is here representative of the internal diameter of the patient's ascending aorta.
Figure 3:
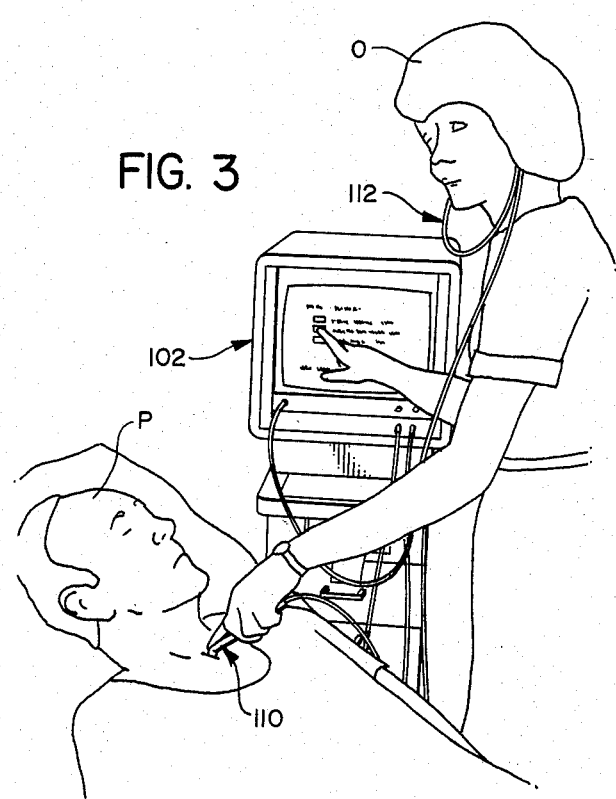
FIG. 3 is a perspective view similar to FIG. 2, but here illustrating the patient, medical practitioner and apparatus at that stage in the process wherein the medical practitioner has positioned a continuous wave ultrasonic transducer within the patient's suprasternal notch with the focused energy beam being directed substantially axially along the patient's ascending aorta, and with the medical practitioner's right index finger being positioned to initiate a cardiac output measuring cycle.

Turning to those figures, in each of which like parts are identified with like reference characters, FIGS. 1–3 diagrammatically illustrate one representation of a system in accordance with the present invention, designated generally as 100, as might be implemented for use in a hospital or like medical facility by an operator "O" in the measurement of the cardiac output of a patient "P". Viewing initially the system as perceived by the operator O, it includes a visual display designated generally as 102, here shown to be a cathode ray tube ("CRT") display having a screen 104 provided with a touch-sensitive overlay 106, greatly facilitating operator interaction with the system as described more fully hereinbelow. From the operator's point of view, the system 100 is further comprised of a pulse-echo transducer designated generally as 108 for A-mode measurement and a continuous wave transducer designated generally as 110 for continuous wave insonification in the examination of systolic velocity. An audio headset designated generally as 112 is included as a part of the system for aural perception of Doppler-shifted signals during that latter, continuous wave examination. A foot switch designated generally as 114 is furnished as an auxiliary means of operator interaction in association with the touch-sensitive overlay 106, allowing the operator to perform certain steps either by touching an active field area on the overlay 106 or depressing the foot switch 114, as may be more convenient depending upon the task at hand. A printer 115, such as a thermal printer, is provided to obtain "hard copy" of the test results for posting in the patient's file. The system 100 is shown to be borne upon a cart 116, for portable mobility about, e.g., a hospital.

A particularly significant advantage of the present invention resides in its use of the operator-interactive display 102 along with the presentation of step-by-step instructional messages thereon to lead the operator through the sequence necessary for determining cardiac output. In this way, operators having no specific background as respects medical instrumentation, or indeed even anatomical structure, may perform the cardiac output measurement in accordance with the instant method without sacrificing either the accuracy of the test or the reliability of its results. This aspect of the present invention is best considered with reference to FIGS. 4-24 which illustrate representative sequences of steps the operator O might perform in conducting the measurement of cardiac output of patient P. FIG. 4 shows the sequence in a flow-chart manner while FIGS. 5-24 show, seriatim, a typical series of graphic images appearing on the display 102 leading operator O through the protocol.

Figure 5:
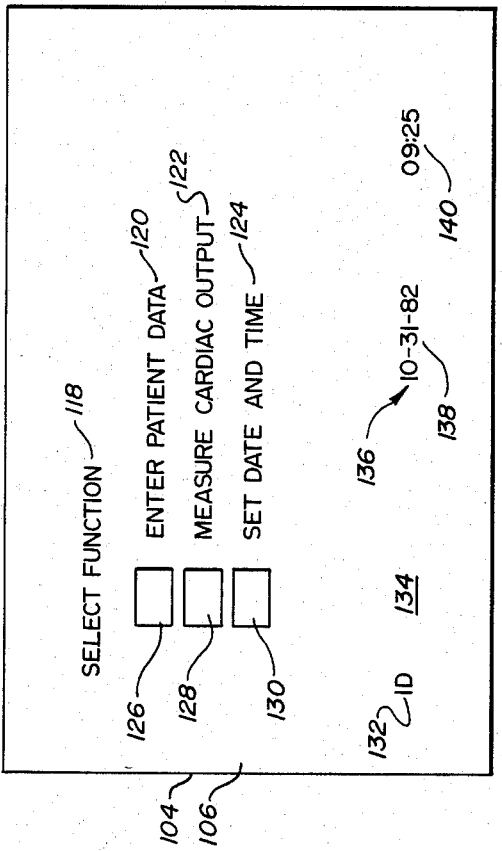
FIGS. 5 through and including 24 are representative illustrations depicting the successive images that might be presented on the face of the cathode ray tube as the medical practitioner progresses through a cardiac output monitoring operation; and, more specifically.

When the system 100 is energized, microprocessor control for the CRT display initially presents a system function menu as shown in FIG. 5. This "MENU" image is one which is displayed periodically throughout the sequence shown in FIG. 4 (as amplified by the individual display illustrations in FIGS. 5-24) or which can be selected at virtually any step throughout that sequence. In this exemplary showing, the menu display appearing on CRT screen 104 includes a first instructional step "SELECT FUNCTION" within a field 118, followed by three options which may be elected by the operator O each bearing an appropriate legend indicative of the choice; viz., "ENTER PATIENT DATA" in a field 120, "MEASURE CARDIAC OUTPUT" in a field 122 and "SET DATA & TIME" in a field 124, prompting the operator to select one or another function. Appearing proximate each legend is a touch-sensitive active area, identified respectively as 126, 128, and 130. As is generally conventional with such touch-sensitive overlays as the overlay 106, a manual touch at one of the sensitive or active areas will be position discriminated and a signal indicative of the area touched will be generated by the overlay and/or its associated interface with the system and raster scan circuitry for the device. As the overlay 106, per se, forms no independent part of the present invention, suffice it to say that the signal may be either an analog or digital signal recognized by, e.g., microprocessor control means for the CRT; in any of which events the important point being the ability for the system to identify the particular option selected by the operator as a function of the position on the screen the operator touches. Irrespective of such considerations, the menu of display of FIG. 5 further includes a fixed field 132 bearing the legend "ID" and a field region 134 for accommodating a patient ID number as described below. Another field 136 shown adjacent the region 134 is provided for the introduction of real time and data information; date information being accommodated within a field region 138 and time information within a field region 140. These provisions for patient identification and real time and date information are preferably included for correlation of the diagnostic measurement to be performed with the patient's chart maintained by the medical facility; as well, in instances where the system provides hard copy output (e.g., printer 115) to give an indication of the timing of each step within the sequence as an aid to diagnostic evaluation by the medical practitioner. Under most circumstances, therefore, the operator O will first enter appropriate patient identification and real time and date data before proceeding further; which option is initiated by the operator's manual touch at touch sensitive area 130.

Figure 6:
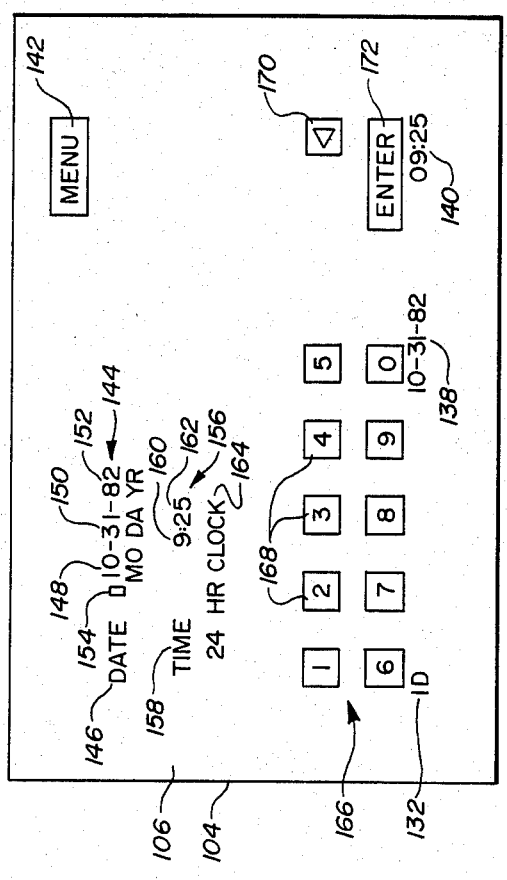
FIG. 6 is a view illustrative of the image that appears on the face of the CRT screen when the operator touches the appropriate active area of the screen shown in FIG. 5 so as to enable resetting of date and/or real time information and, illustrating also, the "keyboard" which appears on the face of the CRT screen for enabling resetting of date and/or time.
Figure 8:
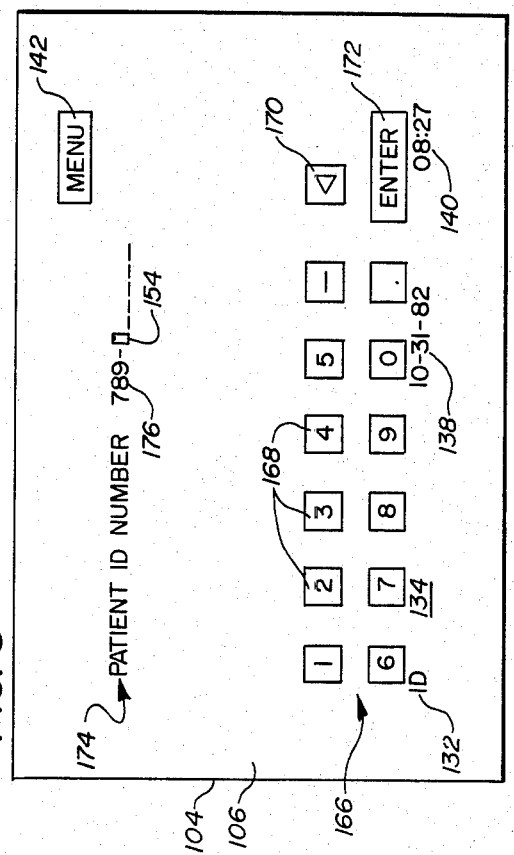
FIG. 8 is a drawing illustrating the graphic image that appears on the face of the CRT screen when the operator activates the Menu shown in FIG. 7 for the purpose of entering patient data with the first item of patient data to be entered being an appropriate identification number (hrein "ID number") and with the drawing here illustrating the CRT screen image following entry of the first four digits of the patient's ID number.

Electing the option to "SET DATA & TIME" presents the visual display shown in FIG. 6. As noted generally above, the system preferably affords the operator O with the ability to gain access to the menu display of FIG. 5 at any intermediate stage of the sequence outlined in FIG. 4. Accordingly, as shown in FIG. 6, the display includes a touch-sensitive area 142 bearing the legend "MENU"; the operator's touch thereat causing the display to resume the form shown in FIG. 5. Having elected the option of setting data and time, the display of FIG. 6 continues with a first field 144 for the data, including a field region 146 bearing the legend "DATE" followed by three field regions 148, 150 and 152 corresponding to two-digit regions for entry of the appropriate month ("MO"), day ("DA") and year ("YR"). A moveable cursor 154 is shown in FIG. 6 to be assuming a position intermediate the data legend in field 146 and the field region 148 for entry of the month, the operation of which is considered below. Beneath the date field is a corresponding time field designated generally 156 which includes a field region 158 bearing the legend "TIME" followed by two two-digit field regions 160 and 162 for entry of the appropriate hour and minute information, respectively. As indicated in a field region 164 subjacent the time region 156, the time to be entered in the fields 160 and 162 is based on a 24 hour clock. As is also evident from FIG. 6, whatever time and date information which initially appears respectively within the fields 138 and 140 also appears in the corresponding field 144 and 156; which information may or may not be accurate when the system is first energized, therefore requiring in most cases the entry of proper date and time information. This is facilitated by a touch-sensitive active region designated generally as 166, shown here to be in a type of "keyboard" form including the digits "1" through "0" in separate touch-sensitive field regions, each identified as 168. The keyboard region further includes a touch-sensitive area 170 bearing an arrow legend for backspacing the cursor 154; and the display might further include a similar touch-sensitive area for advancing the cursor 154 should that be necessary or desirable. The display provides another touch-sensitive region 172 bearing the legend "ENTER" for introduction of appropriate date and time information to the system.

As is now easily envisioned with reference to FIG. 6, the system when first energized has presented within the date region 138 the numerical designation "10-31-82" to indicate Oct. 31, 1982 and in the time region 140 the numerical designation "09:25" to indicate 9:25 a.m. For purposes of the present discussion, let it be assumed that the data entry is correct but that the correct time is 8:26 a.m. vice 9:25 a.m., requiring correction before proceeding further. Where the display includes a cursor moving area for advancement of cursor 154, corresponding to the backspace provision of touch-sensitive area 170, the cursor 154 might simply be cycled through the date field 144 to assume a position for entry of the correct time within time field 156. Otherwise, as shown in FIG. 6, the operator will simply reintroduce the same date information by sequentially depressing the touch-sensitive areas 168 in the sequence 1-0-3-1-8-2 as the cursor 154 sequences automatically among the field regions 148, 150 and 152 corresponding to the month, day and year of the diagnostic test. Once the operator has sequenced through the date, the cursor 154 will then appear in the time field 156 for similar entry of the correct time. In this instance, the operator will touch the active areas 168 in the sequence 0-8-2-6 to enter the correct time of 8:26 a.m. Where the information has been added correctly, touching the active area 172 will enter the data to the system, whereupon the correct date and time will appear in the field regions 138 and 140 respectively. In the event the operator inadvertently touches a wrong one of the active regions 168, the active region 170 may be used to backspace the cursor 154 so the correct information can be entered to the system.

Figure 7:
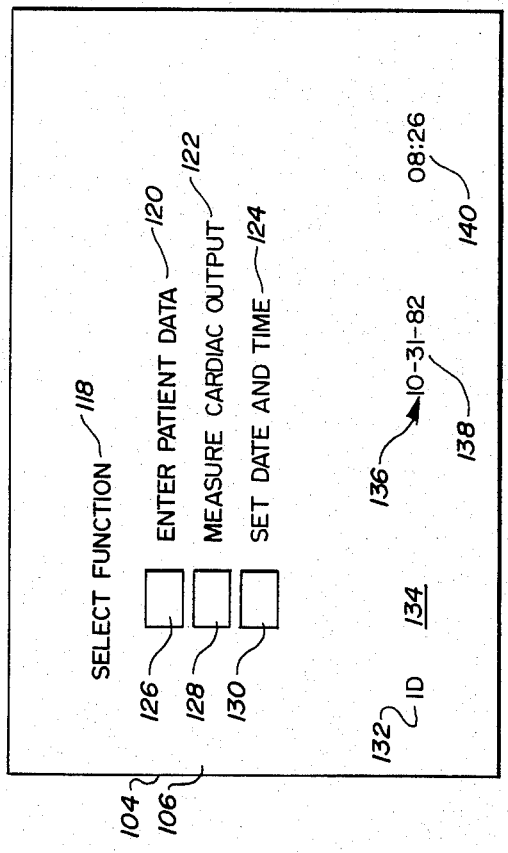
FIG. 7 is a view of the face of the CRT screen illustrating the Menu which reappears with corrected date and/or time information once the medical practitioner has entered corrected date and/or real time data by touching appropriate areas of the CRT screen shown in FIG. 6 and has touched the active screen area in FIG. 6 labelled "Menu"

Once the operator has introduced the correct date and time information, and touches the active enter region 172, the system automatically reverts to the menu display, now shown in FIG. 7. FIG. 7 is identical to the menu display of FIG. 5, save the fact that the correct date and time now appear within the respective regions 138 and 140. At this juncture, the operator will normally enter patient identification data and, for this purpose, apply a touch at sensitive area 126 proximate the legend "ENTER PATIENT DATA" of field 120; whereupon the display of FIG. 8 will appear under control of the microprocessor governing displays on the CRT 104. Again, an active region 142 allowing the operator to revert to the menu display is provided and the real time and date information in fields 138 and 140 appears in this display. The display additionally presents a field 174 bearing the legend "PATIENT ID NUMBER" followed by a field region 176 for introduction of this identification upon sequential movement of the cursor 154 as the operator applies a touch to the active keyboard region 166. In this instance, the keyboard field 166 further includes an active area for a hyphen ("-") and another for a decimal point (".") in addition to the digits "1" through "0". For the sake of illustration, let it be assumed that the appropriate patient identification number is "789-01-2345"; that identification number being entered in the same manner as noted above with reference to the introduction of time and date information; viz., sequentially touching the active field regions 168 in the order 7-8-9---0-1---2-3-4-5, as the cursor 154 advances from place to place within the field region 176. Should the operator inadvertently touch an inappropriate one of the active field areas 168, the cursor may be backspaced by touching the area 170 and correct information then introduced. Once that correct information has been provided within the field region 176, the operator may then touch the active field region 172 to enter the patient identification number within the field region 134. Doing so then causes the display to present the image shown in FIG. 9.

Figure 9:
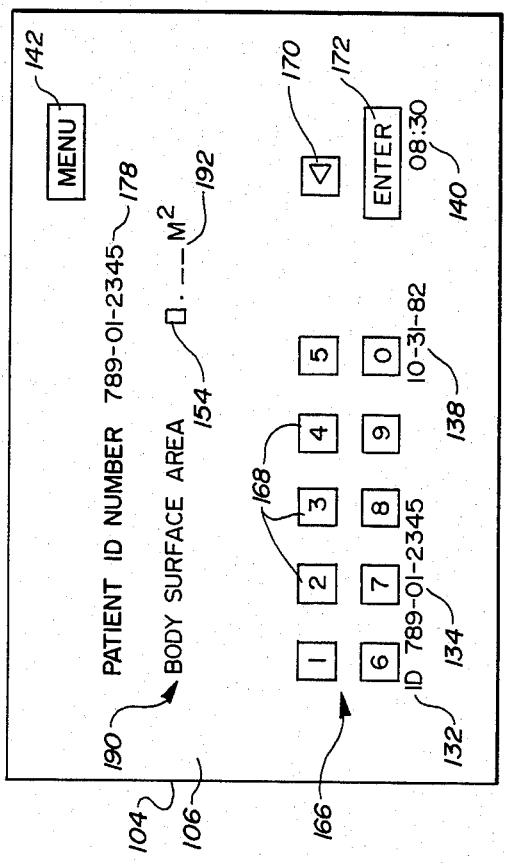
FIG. 9 is a drawing illustrating the next successive graphic image appearing on the face of the CRT screen following entry of the patient's ID number, with such graphic image presenting the medical practitioner with an option to enter either a known value for the patient's body surface area or to calculate such value in the event that it is unknown.
Figure 10:
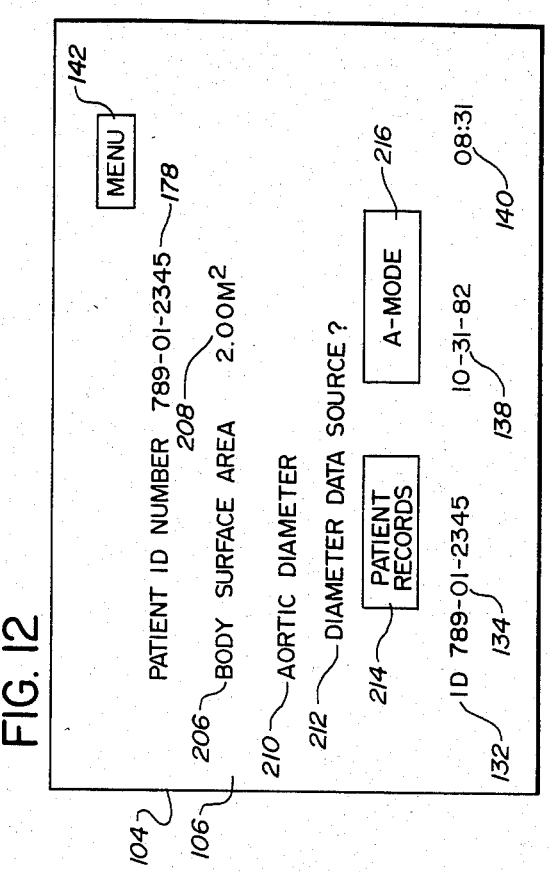
FIG. 10 is a view of the graphic image appearing on the CRT screen when the medical practitioner selects the option presented in FIG. 9 for entry of a known value of body surface area.
Figure 11:
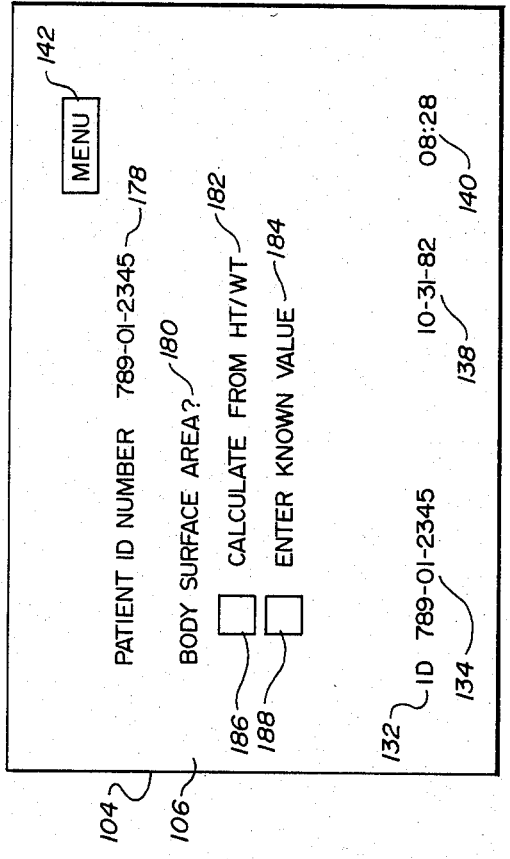
FIG. 11 is a drawing illustrating the graphic image that appears on the face of the CRT screen and which enables the medical practitioner to calculate the patient's body surface area in the event that the value thereof is initially unknown and that the medical practitioner had selected that option by touching the appropriate active area of the CRT screen shown in FIG. 9.

FIG. 9 prompts the operator to the next step in the protocol for conducting the cardiac output measurement in accordance with the present invention. The display, as with the foregoing, includes an active area 142 in order to permit the operator to revert to the menu display. A new region 178 is now included on the display showing the patient's ID number as entered in accordance with the immediately foregoing description. The display likewise includes the ID information within the fields 132 and 134, and also the real time and date data, shown here to be two minutes later than the initiation of the sequence (a relatively realistic time difference). The display of FIG. 9 calls upon the operator to enter the body surface area of the patient, as indicated by the legend "BODY SURFACE AREA?" within a field 180. In this case, the operator is presented with two options for introduction of this surface area data, the first indicated by the legend "CALCULATE FROM HT/WT" appearing in region 182 and the option to "ENTER KNOWN VALUE" appearing as a legend in region 184. Proximate each of the legends within fields 182 and 184 is a touch-sensitive area 186 and 188, respectively, for electing one or the other of these choices. The entry of body surface area at this stage of the protocol is preferred since certain subsequent computations will be made to provide indices based upon the normalizing factor of surface area and, without this information having previously been entered, a "division by zero" will result, obviously yielding inaccurate data.

Where the patient's body surface area is known, for example from previous computations as might appear in the patient's file, the operator will then touch the active area 188 to present the image shown in FIG. 10 on the CRT screen 104. Under these circumstances, in addition to the active and non-active field regions shown in the figure and previously described above, the display includes a legend "BODY SURFACE AREA" in a field designated generally as 190 having a field region 192 for the introduction of the patient's surface area, here shown to be in square meters. The data is introduced within the field region 192 by appropriate touching of the keyboard areas 168 as aforesaid with the moveable cursor 154 indicating the appropriate digit position during the entry procedure. The touch-sensitive overlay 106 further provides a signal to a microprocessor wherein the body surface area is stored for subsequent indexing calculations as described below.

Should the patient's body surface area be unavailable, the operator will apply a touch to the active field region 186 to indicate the need for calculation of that data from the patient's height and weight. In that event, the display to be presented is the one shown in FIG. 11. This display now includes a legend "PATIENT HEIGHT" within a field designated generally as 194 which includes a field region 196 for the introduction of the patient's height in centimeters upon touching the active field regions 168 of the keyboard 166 in the same manner as aforesaid. In this instance, the field 194 further includes a touch-sensitive field area 198 bearing the legend "IN" should the operator desire to introduce the patient's height in inches as opposed to centimeters. If that option is elected, the operator will first touch the active region 198 prior to the keyboard region 166 and the system will recognize the data to be inputted in these English (vice metric) units. The display continues with the legend "PATIENT WEIGHT" within a field designated generally as 200. Like the field 194, the field 200 includes a region 202 within which the operator may enter the patient's weight in kilograms by touching the active areas 168 in the appropriate sequence. And, once again the field 200 includes a touch-sensitive area 204 bearing the legend "LB" to allow the operator a choice for entering the patient's weight in pounds as opposed to the metric units. Accordingly, where the operator desires that ability, the region 204 will be touched prior to introduction of the numerical data via keyboard region 166 and the system will recognize the data to be entered in English as opposed to metric units. Preferably, the system 100 will accept mixed units; e.g., height in metric and weight in English units, or vice versa. The adaptive algorithms required for this conversion are simple and straightforward demanding very little in terms of cost or size while the benefits of providing such an ability are significant in terms of broadening the range of individuals who may operate the system 100 efficiently. Irrespective of that consideration, the height and weight data entered in the fields 196 and 202, respectively, are developed as corresponding signals via the touch-sensitive overlay 106 inputted to, e.g., a microprocessor having stored therein an adaptive algorithm for the surface area computation, a random access memory (RAM) having stored therein appropriate numerical values for generating a signal indicative of body surface area (e.g., via a nomograph), or an equivalent device.

Figure 12:
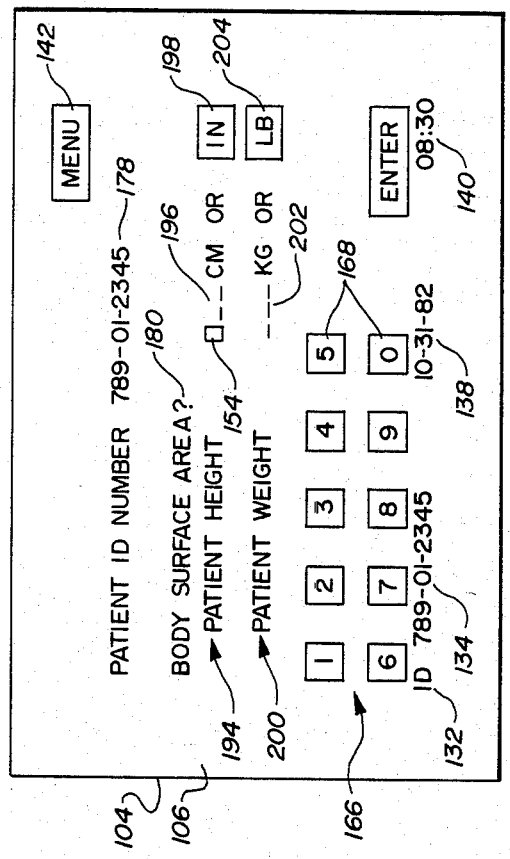
FIG. 12 is a view illustrating the face of the CRT screen and the image presented thereon following entry of the patient's body surface area either from inputting known data (FIG. 10) or from calculating such value by inputting data representative of the patient's height and weight (FIG. 11), and with FIG. 12 showing the two optional paths that can be selected by the medical practitioner for entering the patient's aortic diameter—i.e., either from known data in the patient's records or through an ultrasonic computational mode.
Figure 13:
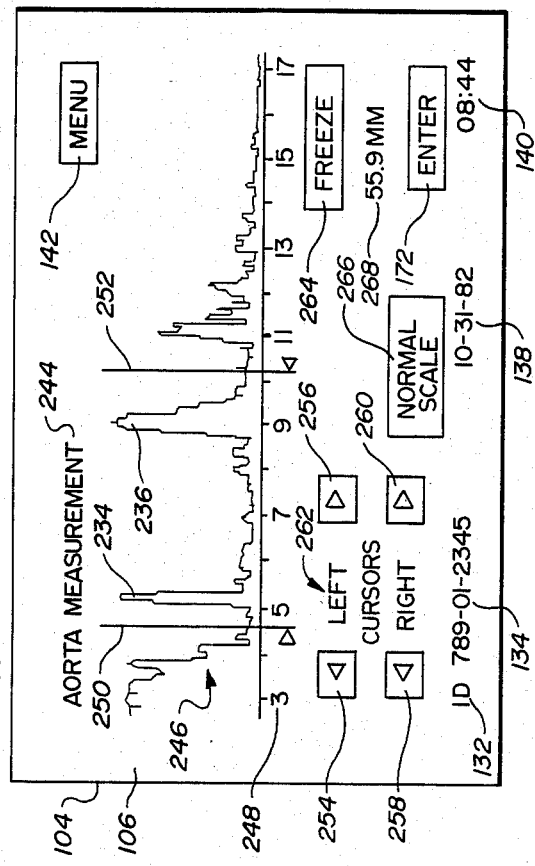
FIG. 13 is the graphic image which is next presented on the face of the CRT screen in those instances where the medical practitioner touches the active screen area in FIG. 12 by which the option is selected for entry of known values of the patient's aortic diameter.

With the entry of body surface area to the system 100, the same is now keyed to begin a sequence for determining the aortic diameter of the patent P. Accordingly, upon the operator's touch at active field 172 in the display shown in FIG. 11, the display of FIG. 12 now appears calling for aortic diameter data. The display of FIG. 12 provides (in addition to the menu field, patient identification fields and real time and date fields as noted above) a first field 206 bearing the legend "BODY SURFACE AREA" followed by a field region 208 wherein the patient's body surface area (either as calculated or as entered from records) appears. The display continues with a legend "AORTIC DIAMETER" in a field 210 indicating to the operator that this is the next stage in the sequence. The display calls upon the operator to elect the mode for entering this aortic diameter data, presenting a general instructional legend "DIAMETER DATA SOURCES?" within a field 212 followed by a first touch-sensitive area 214 bearing the legend "PATIENT RECORDS" and a second touch-sensitive area 216 bearing the legend "A-MODE". In the event the patient's aortic diameter has previously been measured and appears as information within the patient's chart, the operator will touch the active area 214 to present the display of FIG. 13. The image displayed in FIG. 13 includes a region 218 adjacent the field 210 ("AORTIC DIAMETER") for introduction of the appropriate diameter in millimeters via the keyboard array of field 166 in the same manner described above. Should the patient's aortic diameter require measurement, the operator would then touch the active area 216 to convert the system 100 into a measurement mode and present the image shown in FIG. 14. The system 100 also now activates the A-mode circuitry destined for a pulse-echo measurement of the patient's aortic region with an eye toward making the diameter measurement; an operation best envisioned with further reference to FIGS. 2 and 28-32.

The A-mode measurement of aortic diameter is one based on a pulse-echo amplitude study where ultrasonic energy is intermittently applied to the cardiac region and the interfacial, reflected energy from the anatomical structure therein is utilized to determine aortic dimensions. A number of threshold principles warrant some brief discussion at this stage. Ultrasound does not travel well through air or tissue containing any significant quantity of air. Consequently, the lung tissue which almost completely surrounds the heart intermediate it and the chest wall prevents unlimited ultrasonic access to the cardiac region. However, the left lung margin beginning at about the second intercostal space and continuing to about the fourth or fifth intercostal space, follows a lateral course away from the midline placing the heart very close to the chest wall in a region commonly termed the cardiac window. The heart, and specifically the aortic anatomy thereof, may be examined using ultrasonic imaging by transmission and reception of ultrasound through the cardiac window; as envisioned generally with reference to the illustration of FIG. 2.

With the pulse-echo transducer probe 108 positioned as shown in FIG. 2 in order to transmit pulsed ultrasonic energy through the cardiac window, and preferably from about the third or fourth intercostal space, the structure giving rise to echo returns is shown generally in FIG. 28. The aortic wall signals reflected from the root region will appear as a pair of parallel moving signals; the structural sequence being the right ventricle outflow tract 220, the anterior aortic wall 222, the aortic valves 224 (leaflets), the posterior aortic wall 226, the left atrium 228, and the posterior left atrial wall 230. Because the leaflets of the aortic valves are moderately reflective, they provide (along with the characteristic signal returns of the contracting heart) a good reference point for the initiation of aortic diameter measurement across the ascending aortic region. As the heart contracts, blood moving past the aortic valves during ejection forces the leaflets toward the aortic walls, leaving the leaflets generally perpendicular to the beam axis 232 and quite visible on the A-mode trace a good portion of the time. When the aortic valve closes the leaflets touch in the center of the aorta to form a centrally positioned, single echo signal. Consequently, the leaflets may serve as a landmark between the aortic root region and the ascending aorta as best considered with reference to FIGS. 29 and 30.

FIG. 29 shows the pulse-echo transducer probe 108 in two different positions vis-a-vis the aorta; through the root region in the lower position and through the ascending aortic region in the upper position. FIG. 30 shows two pulse-echo signal traces which might appear on the CRT screen 104 corresponding respectively to the lower position of probe 108 in FIG. 29 (FIG. 30A) and the upper position (FIG. 30B). With the objective of obtaining an accurate measurement of the transverse diameter dimension of the ascending aorta, proper positioning of the probe 108 to present the beam axis 232 generally transverse to the ascending aorta is of considerable importance. Initial location of the ascending aorta is facilitated by the characteristic pulse-echo returns from the leaflets 224, allowing the operator O first to locate the probe to find the aorta and thence move it to the region of the ascending aorta. More specifically, the probe is positioned as shown generally in FIG. 2 to present the beam axis 232 through the cardiac window and the probe is manipulated until a signal trace like that of FIG. 30A appears. Focusing simply upon the aortic region, signal returns 234 and 236 will appear corresponding to the reflected returns from the anterior and posterior aortic walls, respectively. With contractions of the heart and concomitant opening and closing of the aortic valve, an intermediate signal trace 238 will likewise appear during ejection periods. Thus, the trace of FIG. 30A is a highly characteristic one, with the parallel moving traces corresponding to the aortic walls and the intermediate trace of varying amplitude corresponding to the leaflets of the aortic valve. Having thus located the aortic root, the operator may simply then move the probe slightly upward to the upper position shown in FIG. 29 until the intermediate echo 238 corresponding to the leaflets no longer appears, indicating a beam axis position now in the ascending aortic region having moved from the root region. With the beam now traversing the ascending aorta, it is next important to take into account proper lateral and/or medial placement of the transducer probe 108 in order to achieve accurate measurement of the aortic diameter. Proper probe positioning will be evident by observation of the geometry of echo returns appearing on the CRT screen 104, as best viewed in FIGS. 31 and 32. FIG. 31 shows the beam axis 232 in three orientations vis-a-vis the ascending aorta, identified A, B and C, where B is the optimal orientation while A is too medial and C is too lateral to obtain an accurate diameter measurement. Each of those three orientations correlates specifically with the signal traces illustrated in FIGS. 32A, 32B and 32C, respectively. With the beam axis 232 shifted toward a medial disposition relative to the aorta, the signal trace on the CRT display will commence with the echo 234 for the anterior wall, followed by an echo 240 corresponding to the right cusp, and a signal 242 corresponding to the echo returned by the posterior cusp. The echo returns shown are low in amplitude and rather broad in extent since the ultrasound beam now includes these additional groups of echo sources. Contrariwise, the signal trace of FIG. 32B shows the echo returns 234 and 236 corresponding respectively to the anterior and posterior aortic walls. The signals are relatively crisp and, when the distance separating the two is minimized on the CRT image, the operator may regard the positioning to be optimized. Proceeding to FIG. 32C, the trace again is underdeveloped, reflecting beam positioning too lateral as respects the aorta. The trace is initiated by a low-level, nearly imperceptible echo 234 for the anterior wall, a signal return 240 from the right cusp and a broadening of the signal return 236 for the posterior wall due to a contribution from the posterior cusp as indicated by signal 242.

With the foregoing as background, it is now evident that proper positioning of the pulse-echo transducer probe 108 is greatly facilitated by the image displayed on CRT 104, whereby operator familiarization with the system occurs easily and rapidly. Once the operator identifies the cardiac window and applies the transducer probe as illustrated diagrammatically in FIG. 2, a brief search will present a signal trace like that shown in FIG. 30A indicative of the aortic root region. The probe is then positioned slightly upwardly to eliminate the signal trace 238 representative of the valve leaflets, whereby the ascending aortic region is properly located. The probe is then manipulated slightly from medial to lateral orientation (or vice versa) and the varying signal patterns shown in FIG. 32 observed with an eye toward obtaining that of FIG. 32B. When the intermediate low level returns from, e.g., the cusp structures have been depressed while the amplitude of the signal returns from the anterior and posterior walls have been maximized with the intervening dimension between returns minimized, the operator is then assured of proper placement for an accurate measurement of the aortic diameter.

Figure 14:
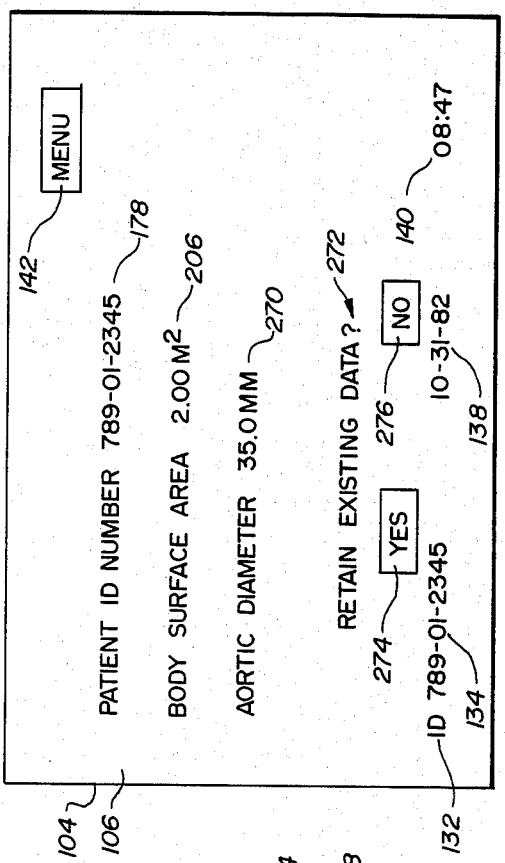
FIG. 14 is illustrative of the graphic image that appears on the face of the CRT screen in those instances where the medical practioner does not know the patient's aortic diameter and, consequently, activitates the ultrasonic computational mode by touching the appropriate area of the screen depicted in FIG. 12.

Returning to a specific consideration of the precise visual display presented for the operator O, touching the active area 216 of the display image shown in FIG. 12 creates the image display shown in FIG. 14. In addition to the active area 142 allowing a return to the menu display, the patient identification and real time and date data appear as indicated above. The display now further includes a legend "AORTA MEASUREMENT" in a field 244 to indicate to the operator that this is the next step in the protocol. Beneath that legend is a graph field region designated generally 246 which includes a signal trace like those discussed above with reference, e.g., to FIG. 32, including therefore pulse echo returns 234 and 236 created by the anterior and posterior walls of the aorta when the probe 108 is properly positioned. The trace 246 further includes a distance scale 248 placed on the screen 104 by the control circuitry driving the CRT raster scan. The scale bears numerical designations, in this case corresponding to the distance from the head of the transducer probe 108 scaled in centimeters. First and second moveable cursors 250 and 252 are also created on the image display of FIG. 14 to assist in the diameter measurement. The first or left cursor 250 is controlled by active field regions 254 and 256 bearing arrow legends indicating the direction of movement upon a manual touch by the operator, while the second or right cursor 252 is positioned via touch-sensitive areas 258 and 260 in like manner. These active areas on the touch-sensitive overlay are indicated by the legends "LEFT" and "RIGHT" "CURSORS" appearing in a field 262 in order to provide convenient operator interaction with the system.

The objective at this stage of the protocol is to obtain the optimized signal trace 246 noted in detail above and thence position the left and right cursors over the signal traces 234 and 236 corresponding to the anterior and posterior aortic walls. With the cursors thus positioned, the measurement of aortic diameter may be made directly from the visual display. However, as also noted above, the signal trace is a changing one as the heart goes through its rhythmic cycling. The measurement of diameter is, therefore, facilitated by freezing the image appearing on CRT screen 104 when the same has been optimized and the operator is confident of its accuracy. The image may be frozen by the operator's manual touch at an active area 264 bearing the legend "FREEZE" or by depressing the foot switch 114 should that be more convenient. In either event, that will stabilize the image allowing accurate positioning of the cursors 250 and 254. The ease of that measurement is further improved by an upward scaling capability, elected by the operator's manual touch at active field region 266 bearing the legend "NORMAL SCALE" which will convert the display from that shown in FIG.

Figure 15:
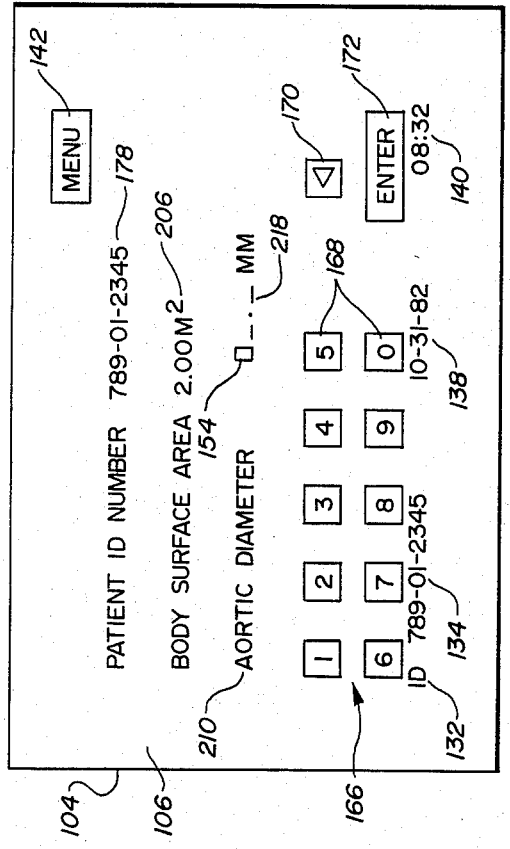
FIG. 15 is a graphic image that might appear on the face of the CRT screen had the medical practitioner elected to shift from the "Normal Scale" shown in FIG. 14 to the "Twice Scale" shown in FIG. 15 by touching the face of the screen in FIG. 14 in the rectangular area labeled "Normal Scale" and, with the image shown in FIG. 15 having been frozen by the medical practitioner and with the left and right cursors having been moved so as to provide an accurate measurement of the inside diameter of the patient's aorta.

14 to the one illustrated in FIG. 15. In the latter figure, the scale is now doubled in size allowing greater discrimination in the placement of the cursors. As best viewed in FIG. 15, the left cursor 250 is positioned toward the trailing edge of the signal trace 234 while the right cursor 252 is positioned near the leading edge of the trace 236 in order to obtain a measurement of the internal dimension of the aorta. Empirically, it has been determined that the system 100 provides the most accurate results where the left cursor is positioned near the peak of the echo return 234, but on the trailing edge side thereof while the right cursor 252 is positioned midway along the leading edge of the echo 236; albeit this precise positioning of cursors to achieve accurate aortic diameter measurement may vary with variations in system design. In any event, the display includes a field 268 which shows the scaled, dimensional separation between left and right cursors in millimeters and, accordingly, aortic diameter when the cursors are properly located. As shown in FIG. 14, the cursors 250 and 252 are outside the echo returns corresponding to the aorta, the field region 268 indicating a scaled distance of 55.9 millimeters. However, with the cursors then properly positioned as shown in FIG. 15, the aortic diameter may be read directly, indicated there to be 35.0 millimeters. With the display in that configuration, the operator then touches the active area 172 bearing the legend "ENTER" to introduce the measured diameter to a storage register in the system.

The system 100 preferably calculates cardiac output as a function of the cross-sectional area of the ascending aorta, thus requiring an area determination from either entered, known data or the measured diameter; although it is equally possible to employ the diameter data directly (e.g., by appropriate scaling in subsequent computation of certain output parameters) should that approach prove more desirable. Following the more preferred approach of computing area, the same is greatly facilitated by modeling the region of the ascending aorta as circular, an assumption which introduces only very slight deviation and one which is tolerable at the savings realized thereby. With that assumption, area can simply be computed by a microprocessor algorithm using standard mensuration formula or, optionally, a read only memory ("ROM") having pre-calculated area measurements corresponding to statistically anticipated diameters might be employed. Regardless, the area data is then stored in a register for subsequent use in the computation of cardiac output.

Figure 16:
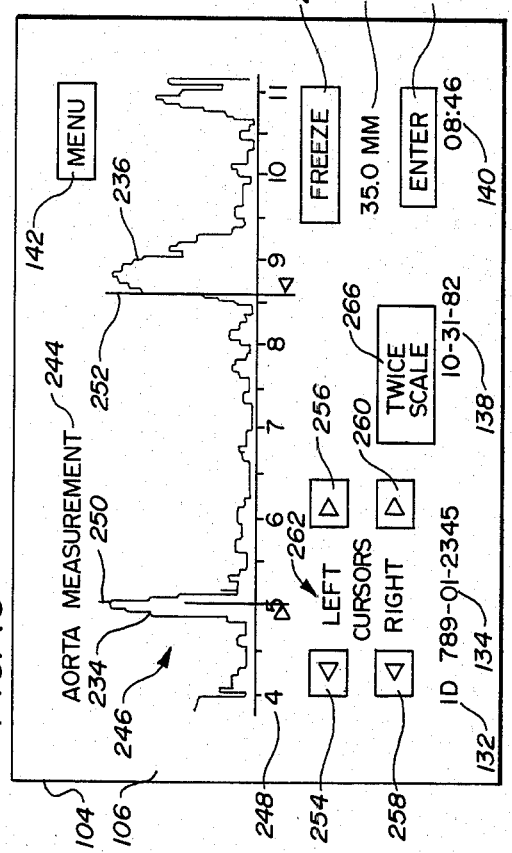
FIG. 16 is a view of the graphic image next appearing on the face of the CRT screen following entry of either known data (FIG. 13) or computed data as measured in FIG. 15 (or in FIG. 14 had the cursors been readjusted and the "Enter" data area touched), and illustrating particularly the option granted to the medical practitioner either to retain the existing data or to correct such data.

Once the aortic diameter measurement has been completed, indicated to the system upon the operator's touch at region 172, the system then presents the display shown in FIG. 16. That display recapitulates the extant data respecting the patient P, including the patient's ID number in the field 178, the patient's body surface area in the field 206 and now the patient's aortic diameter in a field 270. The image then continues with the instructional question to the operator "RETAIN EXISTING DATA?" in a field 272 prompting the operator to reconsider the potential validity of the information previously entered. Touch-sensitive areas 274 and 276 bearing, respectively, the legends "YES" and "NO" allow the operator to elect the retention of existing data or reject it upon a touch at the appropriate field. Should the operator decline to retain the entered data, touching the sensitive area 276 will present the image shown in FIG. 17.

Figure 17:
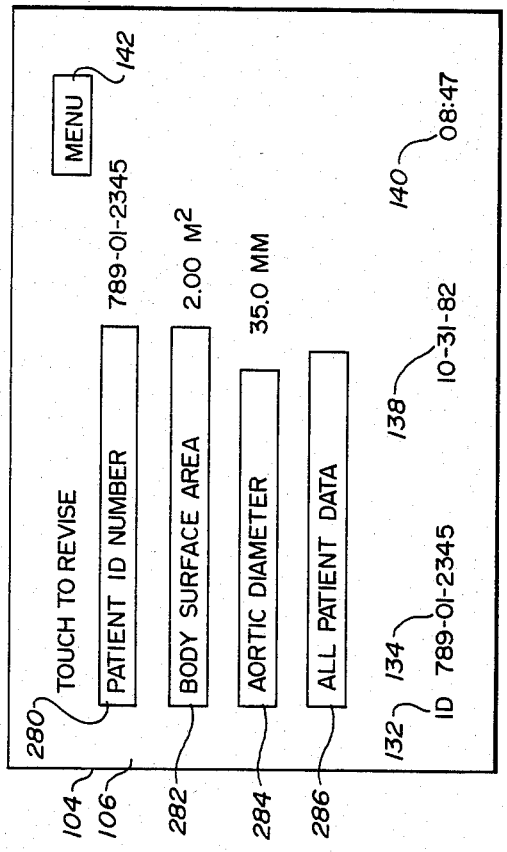
FIG. 17 is a view of the graphic image which would next appear on the face of the CRT screen in those cases where the medical practitioner wished to change all or certain of the data previously entered for a given patient and which would result by touching the area labelled "No" on the screen depicted in FIG. 16.

The image of FIG. 17 begins with the instructional legend "TOUCH TO REVISE" in a field 278. The display then presents four touch-sensitive areas, an area 280 bearing the legend "PATIENT ID NUMBER" followed by the number previously entered, an area 282 bearing the legend "BODY SURFACE AREA" followed by the surface area either formerly entered or calculated, a touch-sensitive area 284 bearing the legend "AORTIC DIAMETER" followed by the diameter previously entered or measured, and a last touch-sensitive area 286 bearing the legend "ALL PATIENT DATA". Thus, the operator is presented with the option to make a selective choice in deleting certain patient data and either re-entering or re-computing it as might be required or, indeed, revising all patient data upon the application of a manual touch to area 286 returning the system to the configuration described above beginning with FIG. 8.

Figure 18:
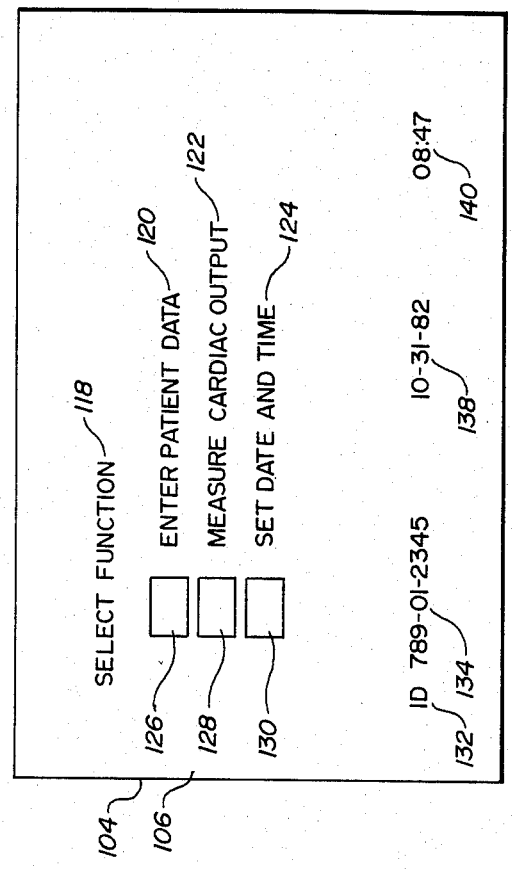
FIG. 18 is a view of the real time Menu that reappears on the face of the CRT screen in those cases where the medical practitioner touches the area labelled "Yes" on the screen shown in FIG. 16.

On the other hand, the operator may have complete confidence in the data theretofore entered within the system and, accordingly, touch the active area 274 in the display appearing in FIG. 16. That will return the system to a mode presenting the menu, as shown in FIG. 18. That display is generally similar to the menu displays described above with reference to FIGS. 5 and 7 and warrants no further detailed discussion; save to say that the next procedure at this stage of the sequence is the measurement of cardiac output prompted by the operator's manual touch at active area 128. The signal developed through the touch-sensitive overlay causes the image of FIG. 19 to appear on the CRT 104 and now keys the system to the continuous wave mode for the measurement of blood flow parameters through the patient's ascending aorta. This aspect of the invention is best understood with initial, brief digression to FIGS. 3, 27 and 34.

While aortic diameter is measured via the A-mode or pulse-echo insonification technique, blood flow through the aorta is measured in accordance with the instant invention by continuous wave insonification. The approach transmits an uninterrupted wave of ultrasound to insonify the region of the ascending aorta along a line generally axial with respect thereto from a position within the patient's suprasternal notch. Reflections from static structure will be returned and detected at the same frequency as the transmitted wave, while moving structure will return energy shifted away from the transmitter frequency by a Doppler-shift frequency proportional to velocity and its directional sense. Accordingly, during each ejection period from the heart, pulsatile blood flow will cause echoes returning therefrom to be frequency-shifted as an indication of velocity; the red blood cells being principally responsible for the reflected return. Detecting the frequency shift and normalizing same yields a velocity signal following the systolic velocity of blood through the ascending aorta during active ejection periods. Subjecting that frequency signal to a spectrum analysis to account for the various frequency contributions and thence integrating the signal over time for the systolic contraction period yields a systolic velocity integral. The product of the systolic velocity integral and the cross-sectional area of the ascending aorta then gives a measure of stroke volume per cycle which, when summed over a predetermined number of cardiac cycles and time averaged with respect thereto, yields cardiac output. While both stroke volume and cardiac output are important individual physiological parameters for the patent under examination, the same are usually normalized based on the patient's body surface to yield, respectively, cardiac index and stroke index. The system 100 leads the operator through these various steps and provides a visual display during the sequence assisting in the efficiency of the measurement technique.

The first step in the measurement of cardiac output is the proper positioning of the continuous wave transducer probe 110 within the patient's suprasternal notch as shown diagrammatically in FIG. 3. The transducer probe 110 includes discrete transmitting and receiving crystals 282 and 284, respectively, positioned within the probe in a manner providing a focal point 286 within a focal zone 288. The configuration is made with an eye toward providing a focal point within the statistically anticipated distance of the ascending aorta from the patient's suprasternal notch, with a focal zone accounting for the physical vagaries among patients to be examined by the system. The ascending aorta lies almost completely behind the sternum, identified generally as 290 in FIG. 34, with a portion of the ascending aorta pointed toward the suprasternal notch identified generally as 292. Placing the transducer probe 110 within the suprasternal notch and aiming slightly anterior within the saggital plane, will generally place the beam in the ascending aorta as shown in FIG. 34. The probe is then manipulated in order to maximize the signal returns appearing on the CRT display, to which attention is now directed, beginning with FIG. 19.

Figure 19:
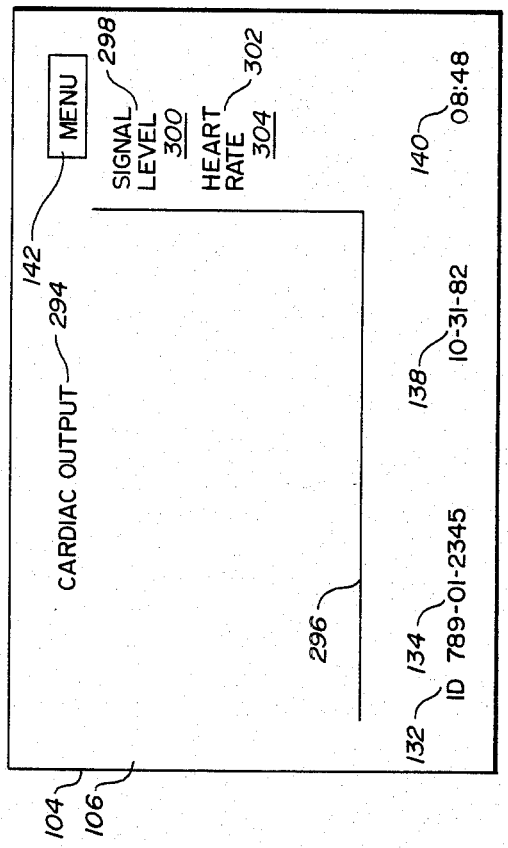
FIG. 19 is a view of the graphic image that first appears on the face of the CRT screen following selection of the "Measure CO (cardiac output)" function by touching the appropriate area of the screen depicted in FIG. 18.

The display image of FIG. 19 provides a legend "CARDIAC OUTPUT" within a field 294 to provide an indication to the operator that this is the stage within the protocol next to be performed. A grid 296 appears in the form of an X-Y coordinate system where the X axis represents time from right to left and the Y axis signal amplitude. A field 298 bears the legend "SIGNAL LEVEL" and includes a field region 300 immediately below wherein a numerical value for the signal level will appear during later stages of the sequence. Likewise, a field 302 bearing the legend "HEART RATE" appears on the display shown in FIG. 19 and includes a field region 304 immediately below where a numerical indication of heart rate will later appear as the sequence progresses. With the probe 110 positioned in the suprasternal notch 292 as aforesaid, the display will begin to present a series of discrete signals 306 (in bar graph form) corresponding to discrete cardiac cycles, the amplitude of which is an indication of stroke volume. Following a predetermined number of cardiac cycles allowing time for positioning of the probe 110, a numerical value appears within the field 300 providing the operator with a direct indication of the existing signal level detected upon systolic ejection of blood. In the preferred embodiment shown, the graphical representation shown in FIG. 20 corresponds to the magnitude of the systolic velocity integral calculations noted briefly above while the signal strength is shown as a simple numeral. Optionally, but preferably, the signals applied to the display are converted first to signals within the audio frequency range, thereby allowing the operator to use either the headset 112 or a speaker to provide both aural and visual observation of the results as the sequence progresses. By combining the use of these Doppler sounds, the SVI values, and visual transducer positioning, the Doppler ultrasound beam can be consistently and correctly located for the cardiac output calculation.

Figure 20:
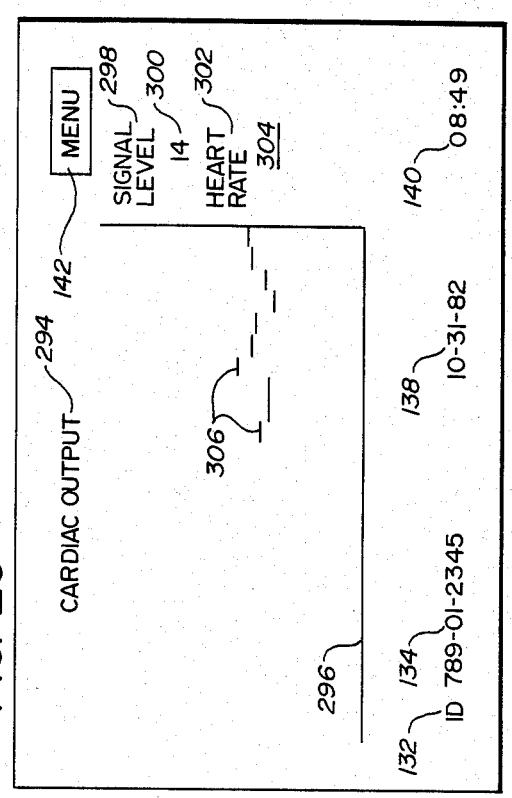
FIG. 20 is a view similar to FIG. 19, but here illustrating the image that appears on the face of the CRT screen when the ultrasonic transducer is properly aimed but before accumulation of data representative of at least twelve consecutive beats containing acceptable data values, it being understood that the horizontal lines representative of successive heartbeats are here moving across the face of the screen from right to left with the latest heartbeat detected being at the right hand side of the image.

After the initial period of positioning, during which the operator maximizes the signal returns shown on the display of FIG. 20, the system will recognize the rhythmic contraction of the heart and thereby monitor heart rate as well as signal level. In the preferred embodiment shown, the system requires at least twelve contraction periods as indicated generally by the vertical phantom line appearing in FIG. 21. After whatever number of cycles required by the system for statistical significance has been reached (here twelve) a legend "MEASURE CO" appears in an active field region 308 indicating to the operator that a cardiac measurement may be taken. In this exemplary embodiment, the cardiac output is calculated on the basis of the twelve most recent contraction periods and, accordingly, those signals appearing to the right of the phantom line in these figures of drawing. Thus, while the operator may initiate a measurement calculation with the display in the configuration shown in FIG. 21, a greater number of cycles may be allowed to accumulate in order for the operator to observe any erratic data either visually by observing the display or aurally through the headset or speaker. Thus, let it be assumed that the operator allows the display to achieve the configuration of FIG. 22 before applying a touch at the sensitive area 308. Once that is done, the computation of cardiac parameters is made by the system firmware and the values displayed as shown in FIG. 23 within a field designated generally as 310. The field includes the legends "CO" for cardiac output, "CI" for cardiac index, "SV" for stroke volume, "SI" for stroke index, and "HR" for heart rate, beneath each of which specific fields appears the calculated or measured parameter. Optionally, but preferably, this image is transferred to hard copy via, e.g., the printer 115 associated with the system in order to provide a permanent record for the patient's chart.

In the event the operator moves the transducer probe 110 out of proper position with respect to the region of the ascending aorta, and thereby loses signal returns from systolic flow, the image of FIG. 24 is one which will appear. As can be seen with reference thereto, approximately eight cardiac cycles have passed without a return, whereupon the system presents the legend "LOW SIGNAL . . . IMPROVE AIM" in a field 312; prompting the operator to reposition the probe in order to obtain valid, maximized data.

As is now evident from the foregoing description of the methodological sequence comprising the process of the present invention, the same offers simple yet highly efficient and reliable cardiac output measurement. The system is operable by a wide range of operators having perhaps widely varying technical and/or medical skills; but, due to the step-wise instructions provided on the visual display in association with the operator-interactive touch-sensitive overlay therefor, the operator is instructed explicitly at each separate step in the process and offered the ability to make elections of various options presented simply upon a manual touch of the overlay or, depending upon the stage, depression of a foot switch. The display, furthermore, assists the operator in proper, accurate positioning of the transducer probes employed, enhancing ease of operation and reliability of result. The system circuitry responsible for the implementation of this process is likewise designed with the same objectives in mind.

Turning to FIG. 25, a schematic block diagram of the principal components of the system is shown. Briefly summarizing the circuitry, the same is constituted of an A-mode section for generating and processing the pulsed ultrasonic energy used in an aortic measurement, a continuous wave section responsible for generating and processing the uninterrupted insonification of the ascending aorta for the measurement of systolic blood flow therethrough, an interface section for associating the various peripheral devices such as the CRT display, touch screen, switch and thermal printer, and processors both for controlling the operative interaction among or between the various sections and for managing the calculations required to obtain the ultimate cardiac output parameters.

Looking first to the central, digital section of the system circuitry, the same is comprised of a system or first central processor unit ("CPU") 320, a continuous wave or second central processor unit ("CW-CPU") 322, an interprocessor bus control circuit 324 and an input/output control circuit ("I/O") 326. The digital section of the system provides the necessary timing and control functions associated with its operation, including data management and transfer, along with necessary interface functions allowing for operator interaction therewith. The two central processor units are essentially identical in structure, with the CW-CPU 322 dedicated to processing the data in respect of the continuous wave measurement of systolic velocity in order to compute the systolic velocity integral for each heart beat; the system CPU 320 being employed for all remaining timing and control functions along with control and display interface with the operator. Each of these functions is under control of firmware program within the CPU devices with EPROMS. Briefly stated, the central processors are conventional devices including a microprocessor, 32K of dynamic random access memory ("RAM") a dynamic RAM control element, read only memories ("ROM") with programming capacity to 64K, and standard miscellaneous timing and control logic. Suitable devices are available in the marketplace meeting these criteria and may be selected by the system designer to meet the demands of the system; the most preferred being a microprocessor known in the trade as a "Z8000" marketed by, e.g., Zilog or Advanced Micro Devices, or its equivalent. The interprocessor bus control 324 provides means for interfacing between the CPU's themselves and the other principal sections of the system.

The interprocessor bus control 324 is likewise of standard commercial design, having timing and control logic, address latches, latches for control discretes and a clock circuit used as a real time clock reference. Although data transfer may be intiated by external interrupts to the central processing units directly, all data transfer activities are more preferably managed through the interprocessor bus control under appropriate firmware control. The timing and control central logic of the interprocessor bus control provides means for converting the data transfer protocol requirements of the, e.g., microprocessors to the protocol requirements of each of the data processing sections within the system.

The input/output control circuitry 326, as is conventional, provides interfacing for the peripheral elements of the system, mainly the printer, foot switch, touch-sensitive overlay, and the video monitor. Again a conventional device, the I/O assembly contains an array of circuitry to provide for address decoding, dynamic RAM data storage, video display drivers, data latches, signal conditioners, analog to digital converters ("ADC") and interrupt logic for the keyboard and video interfaces. A monolithic display chip is preferably included to develop and present the CRT display under firmware control. Through the means of video address decoding and video interrupt logic, the dynamic RAM of the I/O control circuitry can be filled under control from the central processing unit as necessary to present each of the various display images discussed in detail above. Operator interaction with these images is thereby implemented through the touch-sensitive overlay which, in the preferred embodiment shown herein, provides analog signals from a transparent switch memory multiplexed in the ADC for conversion and transfer to the system CPU for data processing. A local microprocessor is included, programmed to convert the keyboard actuation into appropriate X-Y coordinates for the CPU. The line printer interfacing incorporates latches and receivers in order to convert the data transfer rate requirements of the line printer into a compatible interface with the system CPU as well.

Under the control of the digital section, the A-mode section, designated generally as 330, provides the means for implementing aortic diameter measurement. The A-mode circuitry is comprised of a transmitter 332, a receiver 334, pulse control circuitry 336, a video memory 338 and a video generator 340.

The transmitter 332, shown in this embodiment to be shared for joint use in the continuous wave mode as described below, serves to power the pulse transducer 108. In this pulse-echo mode of operation, the transmitter delivers a series of timed pulses to the transducer crystal, exciting the same into bursts of repetitive, intermittent ultrasound applied to the patient's ascending aorta, following which the transmitter is silent allowing returns to be processed in the remaining circuitry. The transmitter 332 is preferably comprised of a power transformer, power rectifiers and filters, FET power switches, an output coupling transformer and appropriate control logic to provide the necessary ringing pulses to the transducer. An enable signal provided by the pulse control circuitry 336 establishes the proper timing and pulse repetition rate for the transmitter. For example, in the embodiment shown in FIG. 25, the application of an enable signal from the pulse control circuit 336 gates the FET's to provide a pulse of, for example, 200 nanoseconds at an amplitude of about 150 volts. This pulse, in turn, causes the transducer crystal to ring at a frequency of about 2.25 MHz. A preferred pulse repetition rate for implementing the instant system is about 60 Hz, allowing a 260 microsecond period following pulse excitation within which to receive echoes returning from the anatomical structure within the insonification zone of the ascending aorta.

The reflected energy incident upon the transducer probe 108 is converted into oscillating electric signals delivered to the pulse receiver 334. The receiver 334 provides means for amplifying the return signals from the transducer 108 and converting the same into a digital format for display processing on the CRT screen 104. Pulse receiver 334 is most preferably comprised of a transmit/receive switch to protect its circuitry against the relatively high power ringing pulse from the transmitter, band pass filters for signal conditioning, video gain amplifiers, a full wave peak detector, ADC means, time compensated gain control circuitry and an automatic gain control loop along with appropriate timing and control logic. These elements of the invention are best considered with reference to FIG. 26.

The input to receiver 334 is made via a transmit receive switch 342 which isolates the transmitter circuitry 332 during times when it applies the excitation pulse to the transducer 108. Echoes received by the transducer are converted to oscillating electrical signals passing through the transmit/receive switch to an RF amplifier 344. The ultrasonic echoes reaching the transducer are very close to the operating frequency of 2.25 MHz, transduced to an oscillating electrical signal with the same frequency as the echo, but one of fairly low amplitude. The amplifier 344 serves to increase the level to one permitting signal processing. Due to tissue attenuation, echo signals from interfaces close to the transducer are larger than those from more distant anatomical structures. For ease of operator interaction with the system, it is preferable to bring these signal amplitudes into conformity by attenuating signal amplitudes from structure closer to the transducer and amplifying signals more distant to achieve a type of spatial normalization in the nature of time compensated gain ("TCG"). In the exemplified embodiment, this time compensated gain is provided by a TCG circuit 345 interposed between the central timer 336 and RF amplifier 344, controlling the signal conditioning achieved in the amplifier in coordination with the timing of insonification pulses to realize spatial normalization and enhance echoes representative of the aortic structure of the patient. The thus-conditioned signals are thence applied to a controlled attenuator stage 346, cooperating with an automatic gain control element 348 for signal amplitude conditioning and a detector 350 for signal processing. The detector is designed to remove the radio frequency components from the received echo signals, leaving but the signal envelope for display. Accordingly, the detector includes rectifiers and filters for converting the oscillating radio frequency signal to pulsating direct current, pulsating at a radio frequency rate. Subsequently, the RF variations are removed to leave merely the envelope representing each echo, the shape of which follows the shape of the echoes received at the transducer 108.

In a highly preferred embodiment, the received echo signals are routed to a 2.25 MHz band-pass filter and then to two video amplifier stages with variable gain control. The gain levels of these two amplifiers are controlled as a function of time in order to increase gain as a function of distance or depth, as indicated above. The output of these amplifiers is routed through another 2.25 MHz band-pass filter and a third variable gain amplifier which provides the automatic gain control. The output of that amplifier is full wave peak detected to provide the video and automatic gain control signals. The video portion is subjected to further processing in a low pass filter.

The video signal being developed through the receiver circuitry is an analog one following the RF envelope as aforesaid. The analog signals are then converted to digital form in an analog-to-digital converter 349 ("ADC"). Preferably, the video signal processed through the low pass filter as noted above is scaled to drive the ADC. The digital video signals are stored in the digital memory of video memory circuit 338 and are read out of that memory under the influence of the video generator 340 in a standard video (CRT) format controlling the raster scan.

The video memory circuit 338 preferably includes a memory address counter and line generation circuit. When enabled with an A-mode command, the video memory alternately reads digitized data from the pulse receiver and stores same in memory, which is thence read out of memory and applied to the video generator 340 for display purposes. The data update rate for the memory is preferably 60 Hz. in concert with the pulse rate of the A-mode transducer. The output of the video memory is routed to the vertical line generator circuitry where digital comparators and a RAM are used to define and format the data suitable for a raster scan display. Offset and scan inputs are also provided from the interprocessor bus control 324 to provide for the display magnification noted above with reference to FIGS. 14 and 15 and truncation of the data when desired by the operator.

The video generator 340 provides the necessary means of converting the video data stored in memory into the appropriate raster display. Within the context of the most preferred embodiment of the present invention, the video generator includes a 3.5 MHz counter and suitable decoding logic and latches for defining bit times, CRT lines and CRT frames to implement a 30 frame per second interlaced display. Video output components include pedestal, blanking, black and white video levels, color burst, enable and synchronization pulses. Suitable clock signals are also provided by the pulse control circuit 336 to correlate these operations.

That control circuit provides the necessary timing and control signals for coordinating the A-mode operational sequence. Included in the most preferred design for the pulse control circuit 336 is a multiphased clock providing 21.48, 10.74, 7.16, 5.37, and 3.57 MHz clocking frequencies, additional counting and bit controlling functions for the video generator circuit, memory clocking and control functions for the video memory circuit, A to D and TGC control functions for the pulse receiver circuit and a composite video summing amplifier for the CRT video display. All functions, including transmitter pulsing, pulse receiver A to D conversion, video memory writing and reading, and video generator component generation, are synchronized to the multiphased clock of the pulse control circuit to minimize display interference which might occur as a result of asynchronous operation. The display may be frozen at any time by disabling the write function in the video memory control in order to facilitate the aortic diameter measurement. All control functions are disabled when the A-mode section is not in use.

Correlating the system circuitry design for the A-mode section 330 with the system operation described above, the operator's manual touch at active area 216 (FIG. 12) is sensed by the overlay 106 which, in turn, provides an input to the input/output control circuit 326 indicative of the operator's need to measure aortic diameter via the A-mode insonification technique. The command is relayed through the system CPU 320 and interprocessor bus control 324, activating the A-mode circuitry 330.

Pulse control circuit 336 provides the enabling pulse train to transmitter 332 which, in turn, develops the excitation voltage pulses causing intermittent, repetitive insonification of the ascending aorta via the transducer crystal. Following a burst of insonification energy, the interpulse period is dedicated to the detection of returns from the anatomical structure within that insonification zone. Pulse echoes are received at the transducer, converted to oscillating, RF signals routed to the pulse receiver 334. Those RF signals are conditioned, processed to yield the envelope replicating the echo patterns, and digitized to yield binary data supplied to video memory 338. In concert with the video generator 340 and pulse control circuit 336, the data is displayed as the trace 246 of, e.g., FIG. 14.

Once the operator has achieved a level of confidence that the image appearing on the display of, e.g., FIG. 14 is an accurate representation of the patient's aortic structure, a manual touch at active area 264 of the display or depression of the foot switch 114 interrupts the write capability of the video circuitry and thereby freezes the image pattern. Manipulation of the left and right cursors 250 and 252, respectively, via the overlay 106, thereby yields a direct, scaled measurement of aortic diameter. Touching the active area 172 on the display at that time enters the measured value (as determined by the scaled distance between cursors), and a signal developed through the overlay 106 is applied to the data bus for ultimate determination of cross-sectional aortic area.

Once the A-mode aortic measurement is concluded, measurement of the systolic blood flow through the aorta is next in order. That aspect of the procedure is governed by the continuous wave ("CW") section of the system circuitry, designated generally as 350. In capsule summary, the CW circuitry is comprised of a CW transmitter 352 (shown to be in physicaly sharing relationship with the pulse transmitter 332), a CW receiver 354, a CW intermediate frequency circuit 356 ("CW-IF"), a fast Fourier transform ("FFT") processor 358 and an FFT control circuit 360; all in concert with and under the guiding control of the digital circuitry described above.

The CW transmitter 352 provides output power to the continuous wave transducer 110, and specifically the transmitting crystal thereof. It is preferably comprised of a line receiver, shaping filter, step-up transformer and an output current buffer. When the CW mode is enabled, a clock signal (here shown to be a 2.5 MHz signal) is applied differentially to the line receiver; the signal is then shaped and filtered to eliminate harmonics greater than 2.5 MHz, and thence amplified through the step-up transformer to, e.g., 10 volt peak to peak. The signal is next preferably routed through the output buffer, for high current output capability, to the transmitter transducing crystal.

The CW receiver 354 serves to amplify incoming reflected CW signals and condition the same to an acceptable level for further signal processing. In the most preferred embodiment of the invention, the CW receiver circuitry includes a band stop crystal filter, several video amplifier gain stages, plural automatic gain control stages, mixers and a frequency locked loop ("FLL") oscillator. Collectively, the components of the CW receiver 354 serve to amplify and condition the signal representative of detected energy within the continuously insonified zone within the ascending aorta and, most preferably, convert the radio frequency signal to an audio one. This aspect of the invention is best considered with reference to FIG. 33.

A master oscillator circuit 362 within the FFT control element 360 provides clocked pulses to a transmitting amplifier 364 of the transmitter circuitry 352. As noted above, the transmitter then creates and delivers a 2.5 MHz signal to the transmitting crystal 282 of the transducer probe 110. The continuous wave of ultrasonic energy is applied to the region of the ascending aorta as described above with reference to FIGS. 27 and 34. Red blood cells comprising the systolic flow of blood through the aorta reflect a portion of that transmitted energy, shifted in frequency from the transmitter frequency by a value proportional to and indicative of the velocity of blood flow in accordance with the Doppler principle. Doppler-shifted, reflected energy is detected at the receiving crystal 284 of the transducer probe, which serves to convert the mechanical oscillations to electrical ones preserving the same frequency excursions and hence Doppler deviation. In the most preferred embodiment, the transmitter frequency is about 2.5 MHz and, accordingly, the signal emanating from receiver crystal 284 will vary above and below that value; the overall signal being a radio frequency signal. It is that radio frequency signal which is applied to the continuous wave receiver 354. The signal is first amplified in an RF amplifier 370 and is next applied to a first stage variable attenuator 372 under the influence of automatic gain control provided by AGC circuit 374. The thus-conditioned, RF Doppler signal is applied as a first input to a mixer 376 receiving as its second input a reference frequency signal from an in-phase divider 378. The two signals (RF Doppler and reference) are beat in the mixer 376 to yield an intermediate frequency Doppler signal. The intermediate frequency Doppler signal is then applied as an input to a second conditioning stage comprised of a variable attenuator 380 likewise controlled by AGC circuit 374 to improve or condition the Doppler signal, accounting for variations in signal amplitude due to differences in tissue characteristics in the insonofied region. The conditioned IF Doppler signal is then applied as a first input to a mixer 382 receiving a second reference frequency signal from the in-phase divider 378 to achieve frequency translation while preserving frequency variations indicative of systolic velocity. Preferably, the in-phase divider 378 provides reference frequencies suitable for translating the initial RF signal to an audio one whereby the operator may "listen" to variations in velocity flow during each cardiac cycle and over successive cycles as related above. Most preferably, the audio signal created is one where the frequency is a direct indication of velocity— for example 0 Hz corresponding to no flow, 2 KHz corresponding to 60 cm/s, etc. in a linear relationship. This is achieved by providing the in-phase divider 378 with the same clock signals from master oscillator 362 controlling the transmitter frequency. The in-phase divider then yields two reference signals, a first having a frequency f and a second having a frequency equal to the difference between the transmitter frequency and f. The higher frequency signal is employed in the first mixer stage 376 and the lower frequency signal in the second mixer stage 382. As a specific exemplification, for the most preferred transmitter frequency of 2.5 MHz, the in-phase divider 378 will provide a 12.5 KHz intermediate frequency signal and a 2.4875 MHz reference frequency signal as the difference between the transmitter frequency and the intermediate frequency. RF signals applied to the first mixer stage will vary about the 2.5 MHz transmitter frequency by values indicative of the velocity of systolic flow in accordance with Doppler-shift principles, the deviation representing velocity. Beating that signal against the 2.4875 reference signal will yield an IF Doppler signal with frequency variations about the 12.5 KHz beat frequency difference. The subsequent mixing with the 12.5 KHz signal from the in-phase divider in the second mixer 382 will effectively strip the signal of all frequency contributions save those directly related to velocity, leaving the desired audio frequency Doppler signal for further processing as well as for aural perception by the system operator. In some instances, the reference signal frequency f may be added to the base transmitter frequency and in that way achieve an indication of direction as well as the magnitude of systolic velocity.

The CW-IF circuit 356, operating cooperatively with the CW receiver 354, preferably also includes clocked filter means for eliminating spurious or otherwise undesirable frequency contributions; i.e., those other than frequencies directly correlated to systolic flow. A high pass clocked filter ("clocked wall filter") 384 provides variable corner frequencies to insure that Doppler frequencies associated with tissue movement or wall motion is effectively rejected during subsequent signal processing, as described below. That signal is then further processed through a clocked low pass filter 386 which also provides selectible corner frequencies to guard against "aliasing" of the higher frequencies into the signal ("clocked anti-aliasing filter"), also considered in somewhat greater detail below.

The audio Doppler signal is applied as an input to a detector 388 which develops the AGC control voltages for circuitry 374. That signal is also applied to the headset 112 for aural perception by the operator and/or audio speaker associated with the system 100. The audio signal is further directed to a spectrum analyzer in order to process the frequency excursions into signals indicative of cardiac output. In the preferred embodiment illustrated herein, that spectrum analysis is provided by the FFT processor 358 in combination with its FFT control circuit 360 in order to perform fast Fourier transform processing.

The FFT processor 358 provides a means for converting the analog Doppler signal, based upon a time domain function, into its corresponding frequency spectrum through fast Fourier transform processing. The processor circuitry, per se, is generally conventional for this purpose, being comprised of a four quadrant multiplier, a track and hold circuit, an A to D converter, an eight-bit digital multiplexer, a 256×12 bit static RAM, a multiplying/accumulator and sequence controller. The four quadrant multiplier allows the FFT processor to multiply the input Doppler signal by a weighting function depending upon the phase of the FFT sequence. This result is then processed through a track and hold element, converted by an A to D converter into eight bits of binary data, and the digital signal is then multiplexed with its Q component. That multiplexed signal is stored in an FFT data memory for subsequent processing in the ALU in accordance with the FFT program sequence stored in the FFT sequence control PROMS producing a 32 point fast Fourier transformation of the frequency spectrum of the Doppler signal.

The processing function is performed under the guidance of the FFT control circuit 360, which provides the necessary timing and control functions for performing the CW data processing function. In the most preferred embodiment of the present invention, the FFT control assembly contains suitable clocks, latches and decoding functions to implement a mulitphased clocking capability and the controls for the filter clocks of the CW-IF circuit, the control functions for the FFT processor, protocol signals for data transfer to the interprocessor bus control 324, clocking signals for the transmitter, CW receiver, CW-IF circuit and FFT processor, and also the multiplexing capability for switching the various audio signals to the CRT monitor. The analog signals multiplexed to the audio monitor include the Doppler signal itself for audio queues for probe positioning as well as a feedback queue indicating keyboard actuation.

Insofar as the FFT circuitry is conventional, the foregoing description is provided merely to exemplify the most preferred functional characteristics to be exhibited, thereby allowing those skilled in the art to select appropriate discrete devices. It will be appreciated, however, that devices meeting the overall functional capability of spectrum analysis of the audio Doppler signal might be employed to equal advantage and, accordingly, could well be implemented within the broader ambit of the present invention by those skilled in this art.

Irrespective of the precise design employed in respect of the FFT processor, per se, the same functions in combination with an analog-to-digital converter used to digitize analog Doppler signals. The FFT circuitry proceeds with the transformation of data at a data sampling rate varying with the systolic velocity of blood flow in order to minimize the hardware and firmware requirements of the system while providing correlation between data frequency and data processing. In brief, the FFT processor receives data at one of a plurality of predetermined data sampling rates for the signal under transformation, the data sampling rate being adjusted to take into account the velocities encountered. The velocity ranges on which sampling rates are based are themselves selected on the basis of those velocities statistically anticipated.

More specifically, and simply by way of exemplification, the present system most preferably provides three data sampling rates for fast Fourier transformation of the analog Doppler signal, correlated with three ranges for anticipated systolic velocities (responsible for the analog Doppler signals). In the most preferred implementation, the three anticipated velocity ranges are overlapping ranges of from 0 to 82 cm/s, 0 to 165 cm/s, and 0 to 330 cm/s. Threshold values within each range determine the need for adjustment or shifting of the correlative data sampling rate. The criteria employed in this highly preferred embodiment causes shifting upon the reception of substantial signals in excess of 78% of the maximum in the specific range, while a lower range will be elected upon reception of substantial signals less than about 26% of the maximum of that range. Thus, for example, shifting from the first data rate to the second data rate will occur upon the reception of substantial signals in excess of 64 cm/s while the data samplaing rate will shift from the second to third upon reception of substantial signals in excess of about 129 cm/s. Down shifting will occur from the third to the second rate where substantial signals less than about 86 cm/s are received, while the same will occur between the second and first rate where substantial signals less than about 43 cm/s are encountered. These shifting points (high and low thresholds) for rate adjustment have been selected to optimize signal processing within the context of the preferred implementation of the system of the present invention; others perhaps being more appropriate depending upon the specific design elected for implementation. Irrespective, and again viewing the most preferred embodiment, a complete FFT spectrum is processed every 2.5, 5 or 10 milliseconds depending upon the sample rate of the FFT processor as dictated by the velocity of blood flow detected. The velocity is monitored and, depending upon the design requirements, the occurrence of one velocity signal above or below a given threshold may cause shifting, a statistical average over several cardiac cycles may determine the substantiality of the signal levels governing shifting, or values determined over plural sequential caridac cycles may dictate this shifting.

Merging the foregoing features within the overall system of the present invention, the audio Doppler signal emanating from mixer 382 (suitably filtered) is applied to an analog-to-digital converter 390 which serves to provide digitized data to an FFT analysis circuit 392 within FFT processor 368 at a predetermined signal sampling rate. The FFT analyzer 392 performs the Fourier transformation in accordance with an algorithm stored therein. The peak component frequency in each sampling period is employed collectively with others in the same cardiac cycle to calculate cardiac output and stroke volume. As the detected velocity of the systolic flow (represented by the processed signal) varies, so too does the sampling rate of the analog-to-digital converter and the processing rate of the FFT analyzer. Also, the clocked wall and anti-aliasing filters of the CW-IF circuitry are adjusted to conform the high and low frequency rejection functions to the frequency of the signal being processed, it being remembered that the audio frequency of the Doppler signal is directly indicative of velocity. The velocity profile signals produced upon Fourier transformation are directly correlated to the actual velocity profile of systolic flow. These velocity profiles are thence integrated over the time of the corresponding cardiac cycle to yield a systolic velocity integral (the area under the curve described by the velocity profile signal) in a microprocessor 394 to yield that value. That value is further used, as described below, the calculate stroke volume from which cardiac output, cardiac index and stroke index may be obtained. It also is responsible for generating the signals appearing on CRT display 104, as described above with reference to FIGS. 19-24.

Microprocessors of conventional design are employed to calculate caridac parameters, based upon the calculated systolic velocity integral and aortic cross-sectional area as aforesaid. Stroke volume on a per cycle basis is achieved as the product of the patient's systolic velocity integral and aortic cross-sectional area. Cardiac output is simply achieved by taking the time-averaged sum of stroke volumes over the collective time period represented by the selected number of cycles. Each of stroke index and cardiac index is achieved as the simple ratio of the respective parameter to the patient's body surface area, a parameter previously computed or otherwise introduced to the system as noted above.

Correlating the system operation from the operator's point of view with the circuitry 350 comprising the CW mode of cardiac measurement, the same is keyed upon the operator's manual touch at active area 128 when the display is in the configuration of FIG. 18. The touch-sensitive overlay provides a signal through the input-/output control circuitry 326 prompting the system to the CW mode via the central processors 320 and 322 and the interprocessor bus control 324. The CW transmitter section 352 receives clocked pulses, its output in turn causing the transmitting transducer crystal 282 to generate a 2.5 MHz, uninterrupted ultrasonic wave directed to the patient's ascending aorta along a propagation line generally axial with respect thereto from a point within the patient's suprasternal notch as viewed in FIGS. 3, 27 and 34. During each active ejection period, systolic flow through the ascending aorta begins from a static no-flow condition, with velocity rising to a maximum followed by a period of decreasing velocity and thence reversed diastolic flow. Transmitted ultrasonic energy is refelected during this period of active ejection, and principally by the red blood cells. Reflected energy is detected by receiving crystal 284; energy reflected from blood cells moving toward the transducer having an increased frequency, Doppler-shifted by a value proportional to velocity while stationary structure returns signals equal to the transmitter frequency. Diastolic flow likewise will return Doppler-shifted signals, but here shifted below the transmitter frequency; thereby providing a benchmark for ascertaining the initiation and termination of systole.

The receiving transducer crystal converts mechanical vibrations from reflected ultrasound into oscillating electrical signal having a radio frequency equal to the mechanical vibration frequency. These electrical signals are amplified, conditioned, and beat with the reference signals from the in-phase divider to yield an analog, audio signal having a frequency directly correlated with blood velocity. That audio may be perceived by the operator via either the headset 112 or an audio speaker associated with the apparatus. It is further applied to spectrum analysis in the FFT processor 358, the data sampling rate thereof being governed by the detected velocity itself. The FFT processor performs the transformation at a rate consistent with the sampling rate, dictated by observed velocity, while pre-processing signal filtration (i.e., frequency contributions from tissues in the clocked wall filter and carrier frequencies in the clocked anti-aliasing filter) is likewise keyed to the velocity (hence frequency) experienced. FFT-processed data in the form of a velocity profile signal, replicating the advancing and then declining velocity of blood flow, is integrated over time to yield the systolic velocity integral in microprocessor circuitry, further employed to determine stroke volume, cardiac output, stroke index and cardiac index. The ability to discriminate systole from diastole as aforesaid provides the further capability to recognize heart rate and the temporal excursion of each such cardiac cycle contributing thereto.

The signal value of the SVI calculation is displayed for each heart beat, as is the heart rate itself, on the video display. The operator will manipulate the transducer probe in response to the displayed signal on the CRT (either the graphical representation or the numerical indication) and/or through aural perception via the headset/speaker arrangement.

Once the predetermined number of consecutive cycles has occurred, (e.g., twelve) the operator's manual touch at sensitive area 308 keys the system, through the touch-sensitive overlay and interfacing circuitry, to make the calculations of cardiac output, stroke volume, cardiac index, and stroke index. The computed values are likewise routed to the display as shown, for example, in FIG. 23; the signals being routed along the data bus, through the interprocessor bus control and applied via the input/output control.

The microprocessor/firmware control implemented in the system described above is all quite straightforward and relatively uncomplicated. Those of ordinary skill in the art will have little difficulty in adapting the method and/or system of the present invention to a particular design given the principles set forth herein and the knowledge possessed by such designers. However, merely for the sake of illustrating a most preferred approach to this end, representative binary programs for the CPUs 320 and 322 are annexed hereto as Appendix I for particular use in association with the most preferred embodiment set forth in detail above.

While the invention has not been described with referenced to certain preferred embodiments, those skilled in the art will further appreciate that various substitutions, modifications, changes and omissions may be made without departing from the spirit thereof. Accordingly, it is intended that the foregoing description be viewed as exemplary only and not work a limitation on the scope of the claims granted herein.

CPU 320

```
0000  01 05 AC 02 07 2E 03 10 4D 05 80 66 00 02 5F 00
0010  2C 18 21 00 08 00 21 01 02 07 3E 03 10 02 E0 21
0020  02 0B 84 8D 48 5F 00 2F FC 21 00 0B 84 02 07 4E
0030  03 10 21 01 00 64 21 02 00 0A 5F 00 30 64 21 08
0040  09 EE 02 07 5E 03 10 21 09 09 7C 21 0A 09 9C 5F
0050  00 04 B2 21 00 04 B0 02 07 6E 03 10 21 01 00 48
0060  21 02 03 5E 5F 00 30 64 21 00 09 80 02 07 7E 03
0070  10 21 01 00 20 21 02 03 A6 5F 00 30 64 4D 05 80
0080  7A 02 07 8E 03 10 00 40 4D 05 80 7C 00 C0 4D 05
0090  80 7E 00 18 8D 08 02 07 9E 03 10 8D 18 5F 00 0D
00A0  7C 21 00 0B 8B BD 12 21 02 00 18 02 07 AE 03 10
00B0  5F 00 0D E2 61 00 80 64 05 00 00 03 07 00 F0 FF
00C0  02 07 BE 03 10 6F 00 80 64 21 00 00 03 5F 00 09
00D0  FA 4D 05 74 02 02 07 CE 03 10 00 10 4D 05 80 8F
00E0  00 10 5F 00 0D F0 5F 00 2C 32 02 07 DE 03 10 5F
00F0  00 0D 7C 7C 01 4D 05 64 02 80 09 4D 05 64 04 02
0100  07 EE 03 10 00 01 4D 05 64 04 00 80 4D 05 64 02
0110  00 00 7C 05 02 07 FE 03 10 5F 00 2D 48 21 00 00
0120  00 21 01 00 30 21 02 00 2D 02 08 0E 03 10 21 03
0130  00 50 5F 00 2D C6 EE 07 65 0B 80 64 63 0A 02 08
0140  1E 03 10 80 64 5F 00 0A D0 E8 EC 21 01 00 68 21
0150  02 00 20 02 08 2E 03 10 21 03 00 50 5F 00 2D C6
0160  EE 07 65 0B 80 64 63 0A 02 08 3E 03 10 80 64 5F
0170  00 0B 32 E8 DC 21 00 00 00 21 01 00 30 02 08 4E
0180  03 10 21 02 00 00 21 03 00 7C 5F 00 2D C6 EE 07
0190  65 0A 02 08 5E 03 10 80 64 63 0B 80 64 5F 00 0A
01A0  D0 E8 CA 21 00 00 38 02 08 6E 03 10 21 01 00 68
01B0  21 02 00 00 21 03 00 2C 5F 00 2D C6 02 08 7E 03
01C0  10 EE 07 65 0A 80 64 63 0B 80 64 5F 00 0B 32 E8
01D0  B8 02 08 8E 03 10 21 00 00 68 21 01 00 B0 21 02
01E0  00 00 21 03 00 2C 02 08 9E 03 10 5F 00 2D C6 EE
01F0  03 5F 00 0C 0C E8 AA 21 00 00 B8 02 08 AE 03 10
0200  21 01 00 FF 21 02 00 28 21 03 00 58 5F 00 2D C6
0210  02 08 BE 03 10 EE 04 5F 00 0B 94 5E 08 07 FE 21
0220  00 00 B8 21 01 02 08 CE 03 10 00 FF 21 02 00 00
0230  21 03 00 23 5F 00 2D C6 EE 27 02 08 DE 03 10 21
0240  00 0B 8B 8D 18 21 02 00 18 5F 00 0D E2 5F 00 02
0250  03 EE 03 10 0B BE 4D 05 80 66 00 01 61 00 80 64
0260  05 00 00 03 02 08 FE 03 10 6F 00 80 64 7C 01 4D
0270  05 64 02 80 00 4D 05 64 04 02 09 0E 03 10 00 00
0280  4D 05 64 04 00 F  4D 05 64 02 00 00 7C 05 02 09
0290  1E 03 10 4D 05 7  02 00 00 4D 05 80 8E 00  3 7F
02A0  0B 5F 00 02 09 7C 03 10 2D 20 5E 0E 07 FE 21 00
02B0  0B 8B 8D 18 21 02 00 18 02 09 3E 03 10 5F 00 0D
02C0  E2 21 00 0B 90 BD 14 21 02 00 0A 5F 00 02 09 4E
02D0  03 10 30 64 97 F0 97 F0 4D 05 64 02 80 00 4D 05
```

```
02E0  64 04 02 09 5E 03 10 00 00 4D 05 64 04 00 80 4D
02F0  05 64 02 00 00 4D 05 02 09 6E 03 10 74 02 00 00
0300  4D 05 80 8E 00 00 5E 08 15 A6 00 1A 02 09 7E 03
0310  10 04 01 01 E1 01 01 01 E9 01 01 02 61 01 01 02
0320  69 02 09 8E 03 10 01 01 02 6D 06 02 01 D8 06 01
0330  02 99 05 01 08 21 02 09 9E 03 10 00 11 04 FC 08
0340  3B 00 04 04 E2 0A 02 00 01 09 F1 02 09 AE 03 10
0350  0A 82 00 01 09 F1 0A 0A 00 01 09 F0 0A 8A 00 01
0360  02 09 BE 03 10 09 F0 0A 04 00 04 05 0D 0A 43 00
0370  07 09 F2 0A 84 02 09 CE 03 10 00 05 05 11 0A 8E
0380  00 06 04 E6 0A AE 00 05 04 EC 02 09 DE 03 10 09
0390  F9 00 06 04 F1 0A 5D 00 02 04 26 0A BA 00 05 02
03A0  09 EE 03 10 04 F7 62 61 03 15 12 13 0F 12 13 00
03B0  63 03 80 64 02 09 FE 03 10 21 01 09 A0 21 08 00
03C0  E0 21 02 07 00 21 03 00 12 02 0A 0E 03 10 14 04
03D0  00 00 00 00 A1 06 5F 00 0E C0 A9 10 A9 80 02 0A
03E0  1E 03 10 5F 00 0E C0 A9 10 A9 80 5F 00 0E C0 A9
03F0  10 A9 80 02 0A 2E 03 10 5F 00 0E C0 A9 10 0B 06
0400  00 09 E3 0F 0B 06 00 0A 02 0A 3E 03 10 E6 06 67
0410  08 80 64 EE 05 0B 06 00 0B EE 02 03 03 02 0A 4E
0420  03 10 00 04 03 06 00 0A 65 03 80 64 8D 78 67 03
0430  80 64 02 0A 5E 03 10 E6 02 60 75 02 06 A1 69 B3
0440  99 00 03 01 09 01 FE 02 0A 6E 03 10 81 79 20 9D
0450  B3 4F 03 00 93 F3 A1 2A 81 7A AD A0 02 0A 7E 03
0460  10 8D 38 A0 4B 5F 00 30 7C A9 07 A0 CB 5F 00 30
0470  7C 02 0A 8E 03 10 A9 07 A0 5B 5F 00 30 7C A9 07
0480  A0 DB 5F 00 30 7C 02 0A 9E 03 10 AD A0 97 F3 14
0490  04 00 00 00 00 A9 70 0B 07 00 08 02 0A AE 03 10
04A0  E7 D5 67 08 80 64 EE 01 A9 00 A9 00 A9 80 01 02
04B0  02 0A BE 03 10 00 20 63 03 80 64 AB 31 0B 08 00
04C0  FF 5E 03 0A 14 02 0A CE 03 10 9E 08 8D C8 0B 0C
04D0  FF FF E6 01 A9 C0 67 0B 80 64 02 0A DE 03 10 E6
04E0  03 21 08 80 7A E8 0A 67 0A 80 64 E6 19 21 08 02
04F0  0A EE 03 10 80 7C 61 09 80 7A A9 96 0B 89 EF 12
0500  0D 01 00 00 02 0A FE 03 10 E6 0F 0B 0C 00 01 E6
0510  03 0B 0C 00 0A E7 05 2B 80 02 0B 0E 03 10 5F 00
0520  0D 7C 5F 00 0D F0 21 00 10 00 5F 00 0E 44 02 0B
0530  1E 03 10 67 0B 80 64 E6 03 5F 00 0E 4E E8 02 5F
0540  00 0E 72 02 0B 2E 03 10 E6 D1 9E 08 8D C8 0B 0C
0550  FF FF E6 01 A9 C0 67 0A 02 0B 3E 03 10 80 64 E6
0560  03 21 08 80 7C E8 0A 67 0B 80 64 E6 19 02 0B 4E
0570  03 10 21 08 80 7A 61 09 80 7C AB 96 0B 89 E3 12
0580  0D 81 02 0B 5E 03 10 00 FF EF 0F 0B 0C 00 01 E6
0590  03 0B 0C 00 0A E7 05 02 0B 6E 03 10 29 80 5F 00
05A0  0D 7C 5F 00 0D F0 21 00 10 00 5F 00 02 0B 7E 03
05B0  10 0E 44 67 0B 80 64 E6 03 5F 00 0E 60 E8 02 5F
05C0  00 02 0B 8E 03 10 0E 84 E6 D1 9E 08 67 09 80 64
05D0  EE 09 65 09 80 64 02 0B 9E 03 10 65 02 80 8E 61
05E0  00 80 8E 6F 00 74 02 9E 08 63 09 02 0B AE 03 10
05F0  80 64 63 02 80 8E 61 00 80 8E 6F 00 74 02 9E 08
0600  02 0B BE 03 10 61 01 80 8C 19 00 00 0A 8D 04 EE
0610  03 0B 01 27 0F 02 0B CE 03 10 E3 02 21 01 27 0F
0620  6F 01 80 20 5F 00 2D 38 5F 00 02 0B DE 03 10 2C
0630  18 21 00 08 00 21 01 02 DF 21 02 0B 88 8D 48 02
0640  0B EE 03 10 5F 00 2F FC 21 00 0B 90 BD 14 21 02
```

```
0650  00 0A 5F 00 02 0B FE 03 10 30 64 4D 05 74 02 00
0660  00 5F 00 20 FC 9E 08 69 06 02 0C 0E 03 10 80 7A
0670  67 08 80 64 EE 78 65 08 80 64 21 00 0A 8E 02 0C
0680  1E 03 10 21 01 00 06 21 02 0D 76 5F 00 30 64 61
0690  03 80 7A 02 0C 2E 03 10 8D 28 0B 03 00 0B E7 0F
06A0  0B 03 00 82 E3 10 4C 05 02 0C 3E 03 10 80 8E F9
06B0  F9 21 03 00 07 61 04 80 7A B3 49 00 01 02 0C 4E
06C0  03 10 03 04 00 F9 E8 28 BD 2B 8D 38 8D 48 E8 0C
06D0  03 03 02 0C 5E 03 10 00 0B 1B 02 00 11 A1 24 61
06E0  02 80 7A 83 42 B3 29 02 0C 6E 03 10 00 01 03 02
06F0  00 0B 6E 0A 80 8E 4D 01 80 7A 00 0B 02 0C 7E 03
0700  10 EF 0E 4D 01 80 7A 00 08 EB 03 4D 05 80 7A 00
0710  09 02 0C 8E 03 10 61 04 80 7A B3 49 00 01 03 04
0720  00 0B E8 04 B3 49 02 0C 9E 03 10 00 01 01 04 00
0730  0B 61 05 80 7C 43 05 80 7A B3 59 02 0C AE 03 10
0740  00 01 4D 01 80 7A 00 05 E3 02 81 45 E8 07 81 45
0750  02 0C BE 03 10 03 05 00 0B 41 05 80 7A 41 05 80
0760  7A 0B 05 00 F8 02 0C CE 03 10 E3 02 21 05 00 F8
0770  6F 04 80 7A 6F 05 80 7C 01 03 02 0C DE 03 10 00
0780  03 6F 03 80 84 6B 06 80 7A 5F 00 0D 7C 65 03 02
0790  0C EE 03 10 80 8E 61 00 80 8E 6F 00 74 02 61 00
07A0  80 84 5F 00 02 0C FE 03 10 09 FA 5F 00 0D F0 9E
07B0  08 63 08 80 64 21 00 0A 8E 02 0D 0E 03 10 21 01
07C0  00 06 21 02 04 E6 5F 00 30 64 4C 05 80 8E 02 0D
07D0  1E 03 10 00 00 63 03 80 8E 61 00 80 8E 6F 00 74
07E0  02 21 00 02 0D 2E 03 10 00 03 5F 00 09 FA 61 03
07F0  80 84 03 03 00 03 8D 28 02 0D 3E 03 10 19 02 00
0800  11 A1 34 61 02 80 7A A1 21 01 02 00 0B 02 0D 4E
0810  03 10 B3 29 FF FF 81 24 6F 04 80 7A 61 03 80 7C
0820  83 13 02 0D 5E 03 10 B3 39 FF FF 81 34 6F 04 80
0830  7C 6B 06 80 7A 5F 00 02 0D 6E 03 10 0D 7C 5F 00
0840  0D F0 9E 08 4C 4F 41 3B 3D 38 93 F4 02 0D 7E 03
0850  10 21 03 00 0B 21 04 0B B8 A1 40 BD 11 21 02 80
0860  7F 02 0D 8E 03 10 5F 00 30 64 A1 40 BD 11 A9 00
0870  21 02 80 7B 5F 00 02 0D 9E 03 10 30 64 A9 43 69
0880  07 80 7E F3 91 4D 05 80 7E 00 18 02 0D AE 03 10
0890  21 03 00 0B 21 04 0B 88 A1 40 BD 11 21 02 80 7F
08A0  02 0D BE 03 10 5F 00 30 64 A1 40 BD 11 A9 00 21
08B0  02 80 7D 5F 00 02 0D CE 03 10 30 64 A9 43 69 07
08C0  80 7E F3 91 4D 05 80 7E 00 18 02 0D DE 03 10 97
08D0  F4 9E 08 AD 31 5F 00 30 7C A9 03 F2 84 AD 31 02
08E0  0D EE 03 10 9E 08 61 0B 80 7C 43 0B 80 7A AB B6
08F0  8D A8 19 0A 02 0D FE 03 10 00 64 67 08 80 64 E6
0900  07 1B 0A 00 22 0B 0A 00 11 02 0E 0E 03 10 E7 08
0910  A9 B0 E8 06 1B 0A 00 11 0B 0A 00 09 E7 01 02 0E
0920  1E 03 10 A9 B0 6F 0B 80 8C 21 00 80 8C BD 15 21
0930  02 80 6E 02 0E 2E 03 10 BD 31 5F 00 2E 3A 21 00
0940  0A 58 BD 15 21 02 80 6E 02 0E 3E 03 10 5F 00 30
0950  64 9E 08 8D 07 B3 19 00 03 F0 84 9E 08 02 0E 4E
0960  03 10 21 00 00 00 21 01 00 30 21 02 00 2D 21 03
0970  00 50 02 0E 5E 03 10 E8 1A 21 00 00 38 21 01 00
0980  68 21 02 00 2D 21 03 02 0E 6E 03 10 00 50 E8 11
0990  21 00 00 00 21 01 00 30 21 02 00 00 02 0E 7E 03
09A0  10 21 03 00 2C E8 08 21 00 00 38 21 01 00 68 21
09B0  02 02 0E 8E 03 10 00 00 21 03 00 2C 61 0A 68 00
```

```
09C0  07 0A 00 FF 61 0B 02 0E 9E 03 10 68 02 07 0B 00
09D0  FF 65 07 92 8C 5F 00 2D C6 63 07 02 0E AE 03 10
09E0  92 8C EE 05 67 0F 68 04 E6 02 8D 41 9E 08 8D 43
09F0  02 0E BE 03 10 9E 08 93 F0 93 F3 A1 10 A1 83 5F
0A00  00 30 7C 97 F3 02 0E CE 03 04 97 F0 9E 08 02 80
0A10  1B 03 01 00 02 0E D2 03 10 91 F6 BD 60 21 07 08
0A20  00 5F 00 30 E2 A9 70 0B 07 02 0E E2 03 10 0A E0
0A30  EE FA 21 07 0B 80 A9 70 21 06 FF FF 5F 00 02 0E
0A40  F2 03 10 30 E2 A9 73 0B 07 10 00 E7 FA 95 F6 9E
0A50  08 5F 00 02 0F 02 03 10 31 70 61 21 00 00 61 10
0A60  00 00 61 28 00 06 61 17 02 0F 12 03 10 00 02 61
0A70  1A 00 04 0B 07 FF FF EE 03 A1 A1 AB 11 02 0F 22
0A80  03 10 E8 F6 61 19 00 06 01 07 08 00 5F 00 31 14
0A90  A9 15 02 0F 32 03 10 F0 92 5F 00 31 82 9E 08 5F
0AA0  00 31 70 61 28 00 08 02 0F 42 03 10 61 24 00 02
0AB0  61 43 00 00 5F 00 0F 5A 01 04 00 06 02 0F 52 03
0AC0  10 F3 85 5F 00 31 82 9E 08 5F 00 31 70 61 45 00
0AD0  02 02 0F 62 03 10 61 46 00 04 61 50 00 00 8D 18
0AE0  8D 28 60 69 00 00 02 0F 72 03 10 60 6A 00 01 5F
0AF0  00 0F B8 61 6A 00 04 0B 0A 00 00 02 0F 82 03 10
0B00  E6 17 61 67 00 02 81 07 01 07 08 00 61 69 00 06
0B10  02 0F 92 03 10 5F 00 31 14 61 6A 00 0A 0B 0A 00
0B20  00 E6 09 61 67 02 0F A2 03 10 00 08 81 07 01 07
0B30  08 00 61 69 00 0C 5F 00 31 14 02 0F B2 03 10 5F
0B40  00 31 82 9E 08 5F 00 31 70 03 01 00 02 03 02 02
0B50  0F C2 03 10 00 02 5F 00 2B 8A 5F 00 31 82 9E 08
0B60  91 F4 5F 00 02 0F D2 03 10 0F EC 0B 04 FF FF E6
0B70  FB 5F 00 10 58 61 45 00 06 02 0F E2 03 10 1F 50
0B80  5F 00 10 66 95 F4 9E 08 91 F0 91 FA 93 F5 02 0F
0B90  F2 03 10 5F 00 10 42 0B 0A 00 00 EE 03 0B 0B 00
0BA0  00 E6 1A 02 10 02 03 10 61 24 00 02 61 41 00 00
0BB0  61 45 00 02 A1 A0 4A 58 02 10 12 03 10 00 02 E7
0BC0  0D 4A 58 00 03 EB 0A A1 B0 4A 58 00 04 02 10 22
0BD0  03 10 E7 06 4A 58 00 05 EB 03 61 00 64 02 E8 05
0BE0  01 04 02 10 32 03 10 00 06 F1 96 21 04 FF FF 97
0BF0  F5 95 FA 95 F0 9E 08 02 10 42 03 10 7C 01 61 0A
0C00  80 80 61 0B 80 82 4D 08 80 80 4D 08 02 10 52 03
0C10  10 80 82 7C 05 9E 08 93 F8 21 08 00 68 5F 00 0F
0C20  5A 02 10 62 03 10 97 F8 9E 08 93 F8 61 28 00 08
0C30  5F 00 0F 5A 97 F8 02 10 72 03 10 9E 08 5F 00 31
0C40  70 61 24 00 04 61 40 00 00 61 28 02 10 82 03 10
0C50  00 0A 61 47 00 02 0B 07 FF FF EE 04 61 44 00 04
0C60  02 10 92 03 10 AB 41 E8 F7 61 49 00 06 1F 90 A9
0C70  45 F0 8E 5F 00 02 10 A2 03 10 31 82 9E 08 5F 00
0C80  31 70 21 09 93 69 61 47 00 02 02 10 B2 03 10 01
0C90  07 08 00 61 4A 00 04 5F 00 31 14 5F 00 31 82 02
0CA0  10 C2 03 02 9E 08 02 10 C4 03 06 65 00 93 3E 9E
0CB0  08 02 10 CA 03 10 14 08 12 13 15 0D 01 09 0D 0F
0CC0  15 14 13 16 09 0F 02 10 DA 03 10 15 14 10 0B 00
0CD0  06 12 11 00 00 13 19 0E 03 0E 0F 02 10 EA 03 10
0CE0  13 19 0E 03 20 1B 1B 0D 13 00 00 00 00 00 00 00
0CF0  02 10 FA 03 10 01 09 0D 00 5F 00 31 70 5F 00 33
0D00  F0 67 0F 91 B2 02 11 0A 03 10 E6 6E 21 00 08 40
0D10  21 01 00 18 21 03 00 00 5F 00 02 11 1A 03 10 30
0D20  94 4D 04 80 86 EE 1B 21 03 00 00 21 00 0A 77 02
```

```
0D30  11 2A 03 10 21 01 00 09 5F 00 30 94 21 00 0A 97
0D40  5F 00 30 94 02 11 3A 03 10 21 00 0A B7 5F 00 30
0D50  94 21 00 0A D7 5F 00 30 94 02 11 4A 03 10 21 00
0D60  09 99 5F 00 30 94 63 0A 92 8C E8 10 21 08 02 11
0D70  5A 03 10 12 5E 21 09 12 50 21 0A 12 54 5F 00 06
0D80  B2 65 0A 02 11 6A 03 10 92 8C 65 08 92 8C 5F 00
0D90  13 CC 5F 00 12 78 4D 01 02 11 7A 03 10 93 00 00
0DA0  0C E7 03 4D 05 93 00 00 0C 8D 08 61 01 02 11 8A
0DB0  03 10 92 FE 5B 00 93 00 61 02 93 00 B3 29 FF FF
0DC0  8B 02 02 11 9A 03 10 EB 01 A9 10 6F 01 93 1C 21
0DD0  00 93 1C 21 01 00 04 02 11 AA 03 10 21 02 92 90
0DE0  8D 38 5F 00 2E 3A 21 00 08 F9 21 01 02 11 BA 03
0DF0  10 00 04 21 02 92 90 5F 00 30 64 21 00 A0 08 21
0E00  01 02 11 CA 03 10 00 04 21 02 92 90 8D 38 5F 00
0E10  2E 3A 21 00 09 99 02 11 DA 03 10 21 01 00 04 21
0E20  02 92 90 5F 00 30 64 E8 31 21 00 02 11 EA 03 10
0E30  08 F9 21 01 00 04 21 03 00 00 5F 00 30 94 21 00
0E40  02 11 FA 03 10 09 99 5F 00 30 94 21 00 0A 39 5F
0E50  00 30 94 21 00 02 12 0A 03 10 0A 77 21 01 00 09
0E60  5F 00 30 94 21 00 0A 97 5F 00 02 12 1A 03 10 30
0E70  94 21 00 0A B7 5F 00 30 94 21 00 0A D7 5F 00 02
0E80  12 2A 03 10 30 94 63 0A 92 8C 63 09 92 8C 67 08
0E90  92 8C E6 08 02 12 3A 03 10 21 00 08 41 21 01 00
0EA0  17 21 02 12 60 5F 00 30 64 02 12 4A 03 10 5F 00
0EB0  31 82 7B 00 02 77 07 02 0A BA 00 02 33 93 02 12
0EC0  5A 03 10 0A 98 00 07 33 8B 0C 0F 17 00 13 09 07
0ED0  0E 01 0C 02 12 6A 03 10 25 25 09 0D 10 12 0F 16
0EE0  05 00 01 09 0D 00 61 00 02 12 7A 03 10 80 56 61
0EF0  01 80 5A 5F 00 12 96 6F 02 80 54 6F 03 02 12 8A
0F00  03 10 80 5B 6F 04 80 5C 5F 00 13 02 9E 08 8D 68
0F10  A1 07 02 12 9A 03 10 19 06 00 64 5B 06 80 1E A1
0F20  73 61 07 80 1E B3 79 02 12 AA 03 10 FF FF 8B 76
0F30  E7 01 A9 30 14 08 00 00 00 00 14 0A 02 12 BA 03
0F40  10 00 00 00 00 A1 0B 8D 68 AD 06 98 08 1A 08 00
0F50  01 02 12 CA 03 10 86 A0 EF 03 21 0B FF FF E8 05
0F60  10 08 00 00 C3 50 02 12 DA 03 10 E7 01 A9 B0 A1
0F70  B4 AD 06 8D 68 A1 47 19 06 00 64 02 12 EA 03 10
0F80  5B 06 80 1E EF 03 21 07 FF FF E8 04 0B 06 00 32
0F90  02 12 FA 03 10 E7 01 A9 70 A1 72 9E 08 67 0E 92
0FA0  8C E6 48 21 00 02 13 0A 03 10 80 5C 21 01 00 05
0FB0  21 02 92 90 21 03 00 02 5F 00 02 13 1A 03 10 2E
0FC0  3A 21 00 0A A1 21 01 00 04 21 02 92 90 5F 00 02
0FD0  13 2A 03 10 30 64 21 00 80 54 21 01 00 05 21 02
0FE0  92 90 21 03 02 13 3A 03 10 00 02 5F 00 2E 3A 21
0FF0  00 0A A6 21 01 00 04 21 02 02 13 4A 03 10 92 90
1000  5F 00 30 64 21 00 80 56 21 01 00 06 21 02 02 13
1010  5A 03 10 92 90 21 03 00 02 5F 00 2E 3A 21 00 0A
1020  AB 21 01 02 13 6A 03 10 00 03 21 02 92 90 5F 00
1030  30 64 21 00 80 58 21 01 02 13 7A 03 10 00 06 21
1040  02 92 90 21 03 00 02 5F 00 2E 3A 21 00 02 13 8A
1050  03 10 0A AF 21 01 00 03 21 02 92 90 5F 00 30 64
1060  21 00 02 13 9A 03 10 80 5A 21 01 00 07 21 02 92
1070  90 21 03 00 02 5F 00 02 13 AA 03 10 2E 3A 21 00
1080  0A 39 21 01 00 04 21 02 92 90 5F 00 02 13 BA 03
1090  10 30 64 67 0E 92 8C E6 04 21 00 0A B2 5F 00 30
```

```
10A0 64 02 13 CA 03 10 9E 08 14 00 00 00 00 00 8D 48
10B0 8D 28 61 03 80 1C 02 13 DA 03 10 61 05 80 98 98
10C0 40 61 05 80 86 98 40 18 00 00 00 02 13 EA 03 10
10D0 00 64 1A 00 00 00 0C 6E 10 02 00 00 FF FF E7 03
10E0 02 13 FA 03 10 21 03 FF FF 8D 18 0B 01 06 37 E3
10F0 01 A9 30 6F 03 02 14 0A 03 0C 80 56 61 00 80 8A
1100 6F 00 80 5A 9E 08 02 00 00 03 10 0E 00 40 00 05
1110 AC C1 00 00 01 C1 00 05 08 C1 00 02 00 10 03 10
1120 04 02 C1 00 04 02 C1 00 04 02 C1 00 04 02 C1 00
1130 02 00 20 03 10 04 02 C1 00 04 02 C1 00 04 02 C1
1140 00 04 02 C1 00 02 00 30 03 10 04 02 C1 00 04 02
1150 C1 00 03 02 C1 00 04 02 C1 00 02 00 40 03 10 02
1160 02 C1 00 02 02 C1 00 02 02 C1 00 02 02 C1 00 02
1170 00 50 03 10 02 02 C1 00 02 02 C1 00 02 02 C1 00
1180 02 02 C1 00 02 00 60 03 10 02 02 C1 00 02 02 C1
1190 00 01 02 C1 00 02 02 D0 00 02 00 70 03 10 00 00
11A0 00 00 00 00 00 03 83 E3 FB FF FB E3 02 00
11B0 80 03 10 83 03 03 03 00 00 00 00 00 C0 C1 C7 DF
11C0 FF DF C7 02 00 90 03 10 C1 C0 C0 C0 00 00 00 00
11D0 00 FF FF FF FF FF FF FF 02 00 A0 03 10 FF F0 F0
11E0 F0 F0 F0 F0 F4 F4 F4 F4 F4 F4 80 80 02 00 B0
11F0 03 10 80 80 80 80 84 84 84 84 F0 40 40 40 F0
1200 F0 F0 02 00 C0 03 01 F0 02 01 00 03 10 00 00 00
1210 00 40 00 05 AC 40 00 05 AC 40 00 05 AC 02 01 10
1220 03 10 40 00 05 AC 40 00 05 AC 40 00 05 AC 40 00
1230 06 FA 02 01 20 03 10 14 8C 10 FE 06 E2 00 00 00
1240 00 00 00 00 00 10 28 02 01 30 03 10 44 7C 44 44
1250 44 00 78 44 44 78 44 44 78 00 38 44 02 01 40 03
1260 10 40 40 40 44 38 00 70 48 44 44 44 48 70 00 7C
1270 40 02 01 50 03 10 40 78 40 40 7C 00 7C 40 40 78
1280 40 40 40 00 38 44 02 01 60 03 10 40 40 5C 44 38
1290 00 44 44 44 7C 44 44 44 00 7C 10 02 01 70 03 10
12A0 10 10 10 10 7C 00 04 04 04 04 04 44 38 00 44 48
12B0 02 01 80 03 10 50 60 50 48 44 00 40 40 40 40 40
12C0 40 7C 00 44 6C 02 01 90 03 10 54 44 44 44 44 00
12D0 44 44 64 54 4C 44 44 00 38 44 02 01 A0 03 10 44
12E0 44 44 38 00 78 44 44 78 40 40 40 00 38 44 02
12F0 01 B0 03 10 44 44 54 4C 3C 00 78 44 44 78 50 48
1300 44 00 38 44 02 01 C0 03 10 40 38 04 44 38 00 7C
1310 10 10 10 10 10 00 44 44 02 01 D0 03 10 44 44
1320 44 44 38 00 44 44 44 44 28 28 10 00 44 44 02 01
1330 E0 03 10 44 54 54 54 7C 00 44 44 28 10 28 44 44
1340 00 44 44 02 01 F0 03 10 28 10 10 10 10 00 7C 04
1350 08 10 20 40 7C 00 38 44 02 02 00 03 10 44 44 44
1360 44 38 00 10 30 10 10 10 10 38 00 38 44 02 02 10
1370 03 10 04 08 10 20 7C 00 38 44 04 18 04 44 38 00
1380 0C 14 02 02 20 03 10 44 7C 04 04 04 00 7C 40 40
1390 78 04 44 38 00 3C 40 02 02 30 03 10 40 78 44 44
13A0 38 00 7C 44 04 08 10 10 10 00 38 44 02 02 40 03
13B0 10 44 38 44 44 38 00 38 44 44 3C 04 04 78 00 00
13C0 00 02 02 50 03 10 00 00 00 00 10 00 00 00 00 7C
13D0 00 00 00 00 00 02 02 60 03 10 10 00 10 00 00
13E0 00 38 44 04 18 10 00 10 00 00 00 02 02 70 03 10
13F0 00 00 00 00 00 7E 38 08 10 38 00 00 00 00 04
1400 02 02 80 03 10 08 10 20 40 00 00 60 44 80 10 20
```

```
1410  4C 0C 00 10 28 02 02 90 03 10 28 44 44 82 82 FE
1420  01 01 01 01 01 01 01 01 80 80 02 02 A0 03 10 80
1430  80 80 80 80 80 FF 00 00 00 00 00 00 00 10 38 02
1440  02 B0 03 10 54 10 10 10 10 00 10 10 10 10 54 38
1450  10 00 04 0C 02 02 C0 03 10 1C 3C 1C 0C 04 00 20
1460  30 38 3C 38 30 20 00 00 00 02 02 D0 03 10 00 00
1470  00 00 FF FF 00 00 00 00 FF FF 00 00 00 00 02 02
1480  E0 03 10 FF FF 00 00 00 00 FF FF 00 00 00 00 00
1490  00 FF 10 02 02 F0 03 10 10 00 00 00 00 00 FF 10
14A0  10 10 10 00 00 00 80 80 02 03 00 03 10 80 E0 80
14B0  80 80 80 80 80 80 F8 80 80 80 80 01 01 02 03 10
14C0  03 10 01 1F 01 01 01 01 01 01 01 07 01 01 01 01
14D0  00 00 02 03 20 03 10 00 00 FF FF FF FF FF FF FF
14E0  FF 00 00 00 00 0F 0F 02 03 30 03 10 0F 0F 0F 0F
14F0  0F 0F F0 F0 F0 F0 F0 F0 F0 F0 F0 F0 02 03 40 03
1500  10 F0 F0 00 00 00 00 00 00 00 0F 0F 0F 0F 0F
1510  0F 02 03 50 03 10 0F 0F 00 00 00 00 00 00 00 00
1520  F0 F0 F0 F0 FF 00 02 03 60 03 10 00 00 00 00 00
1530  00 FF 80 80 80 80 00 00 00 FF 40 02 03 70 03 10
1540  40 40 40 00 00 FF 20 20 20 20 00 00 00 FF 10
1550  02 03 80 03 10 10 10 10 00 00 00 FF 08 08 08 08
1560  00 00 00 FF 04 02 03 90 03 10 04 04 04 00 00 00
1570  FF 02 02 02 02 00 00 00 FF 01 02 03 A0 03 10 01
1580  01 01 00 00 00 D6 D9 D6 DA D6 DB D6 DC D6 DD 02
1590  03 B0 03 10 D6 DE D6 D6 D7 D6 D8 D6 D9 D6 DA D6
15A0  DB D6 DC D6 02 03 C0 03 10 DD D6 DE D6 D6 D7 13
15B0  05 0C 05 03 14 00 06 15 0E 02 03 D0 03 10 03 14
15C0  09 0F 0E 27 05 0E 14 05 12 00 10 01 14 09 02 03
15D0  E0 03 10 05 0E 14 00 04 01 14 01 0D 05 01 13 15
15E0  12 05 00 02 03 F0 03 10 03 01 12 04 09 01 03 00
15F0  0F 15 14 10 15 14 13 05 02 04 00 03 10 14 00 04
1600  01 14 05 00 01 0E 04 00 14 09 0D 05 12 02 04 10
1610  03 10 05 14 01 09 0E 00 05 18 09 13 14 09 0E 07
1620  00 04 02 04 20 03 10 01 14 01 28 0D 2A 0D 0D 5D
1630  5E 05 0E 14 05 12 00 02 04 30 03 10 0B 0E 0F 17
1640  0E 00 16 01 0C 15 05 03 01 0C 03 15 02 04 40 03
1650  10 0C 01 14 05 00 06 12 0F 0D 00 08 14 2B 17 14
1660  10 02 04 50 03 10 01 14 09 05 0E 14 00 08 05 09
1670  07 08 14 00 29 29 02 04 60 03 10 29 00 03 0D 00
1680  0F 12 10 01 14 09 05 0E 14 00 17 02 04 70 03 10
1690  05 09 07 08 14 00 29 29 29 00 0B 07 00 0F 12 41
16A0  02 04 80 03 10 46 3B 45 09 0E 44 3A 43 3F 0B 07
16B0  0C 02 48 39 4C 02 04 90 03 10 41 3D 46 4C 4A 3D
16C0  3B 47 4A 3C 4B 4D 44 4C 4A 39 02 04 A0 03 10 3B
16D0  47 45 39 5E 45 47 3C 3D 48 4A 3D 4B 3D 46 4C 02
16E0  04 B0 03 10 3B 5D 47 5D 04 09 01 0D 05 14 05 12
16F0  00 04 01 14 02 04 C0 03 10 01 00 13 0F 15 12 03
1700  05 28 03 01 12 04 09 01 03 02 04 D0 03 10 00 0F
1710  15 14 10 15 14 00 29 29 29 29 00 0C 2B 0D 02 04
1720  E0 03 10 09 0E 45 3D 46 4D 46 47 4A 45 39 44 4B
1730  3B 39 44 02 04 F0 03 10 3D 3E 4A 3D 3D 52 3D 3D
1740  46 4C 3D 4A 01 0F 12 14 02 05 00 03 10 01 00 0D
1750  05 01 13 15 12 05 0D 05 0E 14 0C 05 06 02 05 10
1760  03 10 14 12 09 07 08 14 10 01 14 09 05 0E 14 00
1770  09 04 02 05 20 03 10 00 0E 15 0D 02 05 12 02 0F
```

```
1780  04 19 00 13 15 12 06 02 05 30 03 10 01 03 05 00
1790  01 12 05 01 28 01 0F 12 14 09 03 00 02 05 40 03
17A0  10 04 09 01 0D 05 14 05 12 51 3D 4B 46 47 04 01
17B0  14 02 05 50 03 10 01 00 04 09 13 10 0C 01 19 00
17C0  00 00 4B 4C 47 4A 02 05 60 03 10 3D 48 4A 47 3A
17D0  3D 0D 01 09 0E 14 01 09 0E 4C 41 02 05 70 03 10
17E0  45 3D 3A 39 4B 3D 10 12 0F 02 05 00 10 0F 13 09
17F0  02 05 80 03 10 14 09 0F 0E 25 25 25 01 0C 09 07
1800  0E 09 0E 07 25 02 05 90 03 10 25 25 0D 01 09 0E
1810  14 01 09 0E 00 03 01 12 0F 14 02 05 A0 03 10 09
1820  04 03 0F 03 09 13 16 13 09 08 12 21 00 01 00 02
1830  05 B0 03 10 7D 0D 8D 08 7D 0B 21 0F FF FE 7D FF
1840  5F 00 06 24 02 05 C0 03 10 61 01 64 06 4D 05 64
1850  02 00 00 4D 05 60 04 00 02 02 05 D0 03 10 4D 05
1860  68 06 80 03 8D 08 6F 00 74 02 4D 05 60 06 02 05
1870  E0 03 10 00 01 4D 05 93 3C 64 04 5F 00 06 34 21
1880  00 00 00 02 05 F0 03 10 21 01 18 00 21 02 80 00
1890  5F 00 30 64 5F 00 06 68 02 06 00 03 10 21 00 08
18A0  00 21 01 03 00 21 02 0B 84 21 04 00 00 02 06 10
18B0  03 10 5F 00 2F FC 5F 00 14 16 8D 07 21 00 50 00
18C0  7D 0A 02 06 20 03 10 5E 08 15 A6 A1 F1 AB 11 0D
18D0  18 AB 11 0B 01 80 00 02 06 30 03 10 EF FB 9E 08
18E0  21 08 06 60 21 09 00 80 8D 48 7D 02 02 06 40 03
18F0  10 7C 01 4D 05 64 02 80 00 20 8C 6F 04 64 04 6F
1900  09 02 06 50 03 10 64 04 A9 80 A9 90 0B 09 00 88
1910  E7 F6 7D 0A 9E 08 02 06 60 03 10 00 80 02 2C 00
1920  17 02 00 21 0A 06 76 21 08 06 B0 02 06 70 03 10
1930  5F 00 06 D0 9E 08 00 00 01 88 01 26 01 C0 01 38
1940  02 06 80 03 10 01 26 02 F8 00 20 02 AE 03 40 01
1950  28 01 26 04 C0 02 06 90 03 10 01 28 01 26 05 E0
1960  00 20 02 CE 06 20 00 90 02 CE 02 06 A0 03 10 0B
1970  00 00 20 00 A1 10 00 00 48 00 71 0B 80 00 7C 02
1980  06 B0 03 10 00 06 14 00 00 00 00 00 21 90 A9 91
1990  8D 18 20 99 02 06 C0 03 10 A9 90 8D 28 20 9A A9
19A0  90 5F 00 2B 8A 8B A9 E7 F1 02 06 D0 03 10 14 A0
19B0  A9 A3 21 A2 5F 00 30 64 A9 A1 8B 8A E3 F8 02 06
19C0  E0 03 10 9E 08 93 F0 8D 08 60 08 68 01 6F 00 80
19D0  80 60 08 02 06 F0 03 10 68 03 6F 00 80 82 97 F0
19E0  7B 00 67 05 80 66 E6 13 02 07 00 03 10 67 01 80
19F0  66 E6 07 4D 05 80 80 00 DC 4D 05 80 82 02 07 10
1A00  03 10 00 44 E8 09 67 02 80 66 E6 06 4D 05 80 80
1A10  00 D0 02 07 20 03 0E 4D 05 80 82 00 13 7B 00 7A
1A20  00 7B 00 7B 00 02 14 16 03 10 5F 00 31 70 4D 05
1A30  6C 00 00 00 21 01 93 2C 5F 00 02 14 26 03 10 26
1A40  8C 5F 00 27 A0 8D 04 EE 06 5F 00 27 2E 5F 00 02
1A50  14 36 03 10 28 0C 8D 04 E6 02 5F 00 14 70 65 04
1A60  93 3E 65 05 02 14 46 03 10 93 3E 4D 05 6C 1E 00
1A70  00 DF FD 5F 00 31 82 9E 08 02 14 56 03 10 91 F0
1A80  BD 1A 61 00 6C 1E F1 83 4D 05 6C 1E 00 09 02 14
1A90  66 03 10 4D 05 6C 1C 00 01 95 F0 9E 08 91 F0 21
1AA0  01 6C 08 02 14 76 03 10 21 00 6C 1A 0D 15 00 00
1AB0  A9 11 8B 01 E3 FB 4D 08 02 14 86 03 06 60 08 95
1AC0  F0 9E 08 02 14 8C 03 10 5F 00 31 70 21 01 93 3C
1AD0  0D 15 64 04 DF CF 21 0B 02 14 9C 03 10 80 64 21
1AE0  0C 93 3E 27 BF E6 0A 21 07 0B 86 21 06 02 14 AC
```

```
1AF0  03 10 00 00 27 C8 E6 02 21 06 00 05 5F 00 30 E2
1B00  27 BC 02 14 BC 03 10 EE 0C 27 B2 E6 0A 21 07 0B
1B10  80 21 06 00 D0 27 C8 02 14 CC 03 10 E6 02 21 06
1B20  00 A5 5F 00 30 E2 27 C8 E6 03 23 C8 02 14 DC 03
1B30  10 8D 68 E8 03 25 C8 21 06 00 27 21 07 0A FD 5F
1B40  00 02 14 EC 03 10 30 E2 BD 1A 61 00 6C 1E F1 83
1B50  5F 00 31 82 7B 00 02 14 FC 03 10 5F 00 31 70 61
1B60  00 6C 08 07 00 00 0F 0B 00 00 0F 02 15 0C 03 10
1B70  E6 F9 21 01 93 2C 21 07 0A FB 21 08 00 00 A1 19
1B80  02 15 1C 03 10 BD A5 21 02 93 5A 67 05 93 3E E6
1B90  06 2F 20 5F 00 02 15 2C 03 10 27 2E 5F 00 31 14
1BA0  E8 23 0B 20 E6 21 2F 20 5F 00 02 15 3C 03 10 27
1BB0  2E 5F 00 31 14 A1 12 21 03 15 9C BD 45 BA 36 02
1BC0  15 4C 03 10 04 2E E6 1F 5F 00 26 8C A1 12 21 03
1BD0  15 A1 BD 45 02 15 5C 03 10 BA 36 04 2E E6 11 60
1BE0  08 60 09 A9 00 0A 08 63 63 02 15 6C 03 10 E3 01
1BF0  8D 08 6F 00 60 08 5F 00 26 8C E8 05 67 04 02 15
1C00  7C 03 10 93 3E E6 07 5F 00 26 8C 21 07 0A F1 BD
1C10  A8 5F 00 02 15 8C 03 10 31 14 63 04 93 3E 63 05
1C20  93 3E 5F 00 31 82 9E 08 02 15 9C 03 0A 30 30 A7
1C30  30 30 30 31 A6 30 31 02 15 A6 03 10 4D 08 80 66
1C40  5F 00 2C 18 21 00 08 00 21 01 02 E0 02 15 B6 03
1C50  10 21 02 0B 84 8D 48 5F 00 2F FC 21 08 16 66 21
1C60  09 02 15 C6 03 10 16 44 21 0A 16 50 5F 00 06 B2
1C70  5F 00 30 42 5F 00 02 15 D6 03 10 06 34 5F 00 2C
1C80  32 5F 00 06 68 5F 00 2D 48 0B 0A 02 15 E6 03 10
1C90  00 14 E7 FB 0B 0A 00 5B EB F8 0B 0B 00 94 EB F5
1CA0  02 15 F6 03 10 0B 0B 00 78 E7 04 61 00 64 02 5E
1CB0  08 16 68 0B 0B 02 16 06 03 10 00 77 EB EB 0B 0B
1CC0  00 60 E7 0C 61 00 64 02 4D 04 02 16 16 03 10 80
1CD0  1E 5E 06 16 94 4D 04 80 20 5E 06 17 3C 5E 08 02
1CE0  16 26 03 10 31 D0 0B 0B 00 5F EB D9 0B 0B 00 48
1CF0  E7 D6 61 00 02 16 36 03 10 64 02 5E 08 16 3C 5F
1D00  00 28 44 5E 08 15 A6 00 C4 02 16 46 03 10 02 01
1D10  01 24 02 01 01 84 02 01 08 62 00 10 03 C6 02 16
1D20  56 03 10 08 E9 00 12 03 D6 09 49 00 16 03 E8 09
1D30  A9 00 11 02 16 66 03 02 03 FE 02 16 68 03 10 4D
1D40  05 80 66 00 01 67 01 80 64 EE 1B 5F 00 2C 18 02
1D50  16 78 03 10 21 00 08 00 21 01 02 E0 21 02 0B 84
1D60  8D 48 5F 00 02 16 88 03 10 2F FC 5F 00 18 F8 E8
1D70  02 5F 00 18 9E 5F 00 1A 06 02 16 98 03 10 5F 00
1D80  1E 86 65 01 80 64 5F 00 17 F2 67 0F 92 8C 02 16
1D90  A8 03 10 EE 1E 5F 00 2C 18 21 00 08 00 21 01 02
1DA0  E0 21 02 02 16 B8 03 10 0B 84 8D 48 5F 00 2F FC
1DB0  21 08 17 A0 21 09 17 6A 02 16 C8 03 10 21 0A 17
1DC0  7E 5F 00 06 B2 21 0C 00 03 5F 00 20 FC 02 16 D8
1DD0  03 10 5F 00 2C 32 5F 00 2D 48 5F 00 2D 20 EE 04
1DE0  5F 00 02 16 E8 03 10 2D 38 5E 08 15 A6 21 00 00
1DF0  00 21 01 00 A8 21 02 02 16 F8 03 10 00 8C 21 03
1E00  00 B0 5F 00 2D C6 EE 03 5F 00 18 9E 02 17 08 03
1E10  10 E8 CB 21 00 00 00 21 01 00 A0 21 02 00 6C 21
1E20  03 02 17 18 03 10 00 8C 5F 00 2D C6 EE 03 5F 00
1E30  1A 06 E8 BD 21 00 02 17 28 03 10 00 00 21 01 00
1E40  98 21 02 00 4C 21 03 00 6C 5F 00 02 17 38 03 10
1E50  2D C6 EE 03 5F 00 1E 86 E8 AF 21 00 00 00 21 01
```

```
1E60  02 17 48 03 10 00 98 21 02 00 28 21 03 00 48 5F
1E70  00 2D C6 EE C2 02 17 58 03 10 21 01 80 00 0C 18
1E80  A9 10 0B 01 80 28 E7 FB 5E 08 02 17 68 03 10 16
1E90  8A 00 61 11 01 00 E1 11 01 00 1A 04 01 01 61 02
1EA0  17 78 03 10 0F 01 01 E1 10 01 08 3B 00 04 04 E2
1EB0  08 22 00 0F 02 17 88 03 10 17 A2 08 82 00 11 17
1EC0  B1 09 02 00 11 17 C2 09 82 02 17 98 03 10 00 0F
1ED0  17 D3 0A 02 00 10 17 E2 14 0F 15 03 08 00 02 17
1EE0  A8 03 10 14 0F 00 12 05 16 09 13 05 48 39 4C 41
1EF0  3D 46 4C 02 17 B8 03 10 38 41 3C 38 46 4D 45 3A
1F00  3D 4A 3A 47 3C 51 38 4B 02 17 C8 03 10 4D 4A 3E
1F10  39 3B 3D 38 39 4A 3D 39 39 47 4A 4C 41 02 17 D8
1F20  03 10 3B 38 3C 41 39 45 3D 4C 3D 4A 39 44 44 38
1F30  48 39 02 17 E8 03 10 4C 41 3D 46 4C 38 3C 39 4C
1F40  39 5F 00 31 70 21 00 02 17 F8 03 10 08 00 21 01
1F50  02 E0 21 02 0B 84 8D 48 5F 00 2F FC 02 18 08 03
1F60  10 21 0C 00 03 5F 00 20 FC 21 08 18 9C 21 09 18
1F70  68 02 18 18 03 10 21 0A 18 74 5F 00 06 B2 21 00
1F80  00 1A 21 01 00 12 02 18 28 03 10 5F 00 22 0C 5F
1F90  00 2C 32 5F 00 2D 48 5F 00 2D 20 02 18 38 03 10
1FA0  EE 05 5F 00 31 82 97 FE 5E 08 15 A6 5F 00 30 16
1FB0  02 18 48 03 10 E6 06 5F 00 30 2C EE F0 63 0F 92
1FC0  8C E8 04 5F 00 02 18 58 03 10 22 38 65 0F 92 8C
1FD0  5F 00 22 26 5F 00 31 82 9E 08 02 18 68 03 10 00
1FE0  1A 04 01 02 88 03 01 02 93 02 01 08 82 00 11 02
1FF0  18 78 03 10 05 16 08 3B 00 04 04 E2 09 02 00 11
2000  05 27 09 82 02 18 88 03 10 00 0F 05 39 0A 46 00
2010  15 04 0F 0A A9 00 03 05 48 02 18 98 03 10 0A B4
2020  00 02 05 4B 5F 00 31 70 21 00 08 00 21 01 02 18
2030  A8 03 10 02 DF 21 02 0B 88 8D 48 5F 00 2F FC 8D
2040  C8 5F 00 02 18 B8 03 10 20 FC 5F 00 2D 38 21 06
2050  80 6E 21 07 80 00 BD 8B 02 18 C8 03 10 BA 71 08
2060  60 21 01 00 14 21 02 80 00 21 05 00 0B 02 18 D8
2070  03 10 0C 24 E6 06 A9 10 A9 20 AB 50 0B 01 00 1F
2080  E7 F8 02 18 E8 03 10 6F 01 80 6A 01 01 08 80 A1
2090  10 5F 00 2C 00 E8 16 02 18 F8 03 10 5F 00 31 70
20A0  21 00 08 00 21 01 02 DF 21 02 0B 88 02 19 08 03
20B0  10 8D 48 5F 00 2F FC 5F 00 2D 38 21 00 08 94 21
20C0  05 02 19 18 03 10 00 0B 5F 00 2C 00 4D 05 80 6A
20D0  00 14 4D 05 80 6C 02 19 28 03 10 00 04 5F 00 2C
20E0  4C 21 08 1A 04 21 09 19 E2 21 0A 02 19 38 03 10
20F0  19 EE 5F 00 06 B2 5F 00 2C 7A 21 05 00 0B 61 04
2100  02 19 48 03 10 80 6A 03 04 00 14 5F 00 2C 32 5F
2110  00 21 94 5F 00 02 19 58 03 10 2D 48 5F 00 2D 20
2120  EE 07 5F 00 2D 38 5F 00 31 82 02 19 68 03 10 97
2130  FE 5E 08 15 A6 21 06 08 94 21 07 FF FF 5F 00 02
2140  19 78 03 10 2E 96 E6 EB 21 06 08 94 21 07 FF FF
2150  63 0D 80 64 02 19 88 03 10 63 0C 92 8C 5F 00 2F
2160  0C E6 E0 21 00 00 A4 21 01 02 19 98 03 10 00 C3
2170  21 02 00 24 21 03 00 48 5F 00 2D C6 EE 09 02 19
2180  A8 03 10 BB 54 EF D3 21 00 00 26 6E 48 80 6E 5F
2190  00 2F 8E 02 19 B8 03 10 E8 CC 5F 00 2D 6E EE C9
21A0  65 01 80 64 21 06 80 00 02 19 C8 03 10 21 07 80
21B0  6E 21 05 00 0B BA 71 05 60 5F 00 30 42 02 19 D8
21C0  03 10 5F 00 2D 38 5F 00 31 82 9E 08 00 1A 04 01
```

```
21D0  02 15 02 19 E8 03 10 01 01 02 95 01 01 08 3B 00
21E0  04 04 E2 0A 36 00 01 02 19 F8 03 10 04 29 0A B6
21F0  00 01 04 28 08 82 00 11 05 16 5F 00 02 1A 08 03
2200  10 31 70 21 00 08 00 21 01 02 E0 21 02 0B 04 8D
2210  48 02 1A 18 03 10 5F 00 2F FC 21 0C 00 00 5F 00
2220  20 FC 21 08 1E 64 02 1A 28 03 10 21 09 1E 3C 21
2230  0A 1E 48 5F 00 06 B2 21 00 00 13 02 1A 38 03 10
2240  21 01 00 08 5F 00 22 0C 5F 00 2C 32 5F 00 2D 48
2250  02 1A 48 03 10 5F 00 2D 20 EE 05 5F 00 31 82 97
2260  FE 5E 08 15 A6 02 1A 58 03 10 21 00 00 00 21 01
2270  00 40 21 02 00 58 21 03 00 80 02 1A 68 03 10 5F
2280  00 2D C6 E6 76 21 00 00 00 21 01 00 40 21 02 02
2290  1A 78 03 10 00 30 21 03 00 57 5F 00 2D C6 EE E0
22A0  5F 00 2C 18 02 1A 88 03 10 5F 00 22 26 21 00 09
22B0  13 21 01 01 CC 21 02 0B 84 02 1A 98 03 10 8D 48
22C0  5F 00 2F FC 21 0C 00 01 5F 00 20 FC 5F 00 02 1A
22D0  A8 03 10 2C 7A 4D 05 80 6A 00 18 4D 05 80 6C 00
22E0  08 BD 44 02 1A B8 03 10 4D 01 80 1E 00 00 EE 0A
22F0  4D 05 80 6A 00 14 8D 48 02 1A C8 03 10 21 00 09
2300  14 BD 54 5F 00 2C 00 E8 07 21 06 80 6E 02 1A D8
2310  03 10 21 07 80 0B BD 84 BA 71 08 60 5F 00 2C 4C
2320  5F 00 02 1A E8 03 10 2C 32 21 05 00 04 5F 00 21
2330  94 21 00 00 00 5F 00 02 1A F8 03 10 21 F4 5F 00
2340  2D 48 5F 00 2D 20 EE 07 5F 00 2D 38 02 1B 08 03
2350  10 5F 00 31 82 97 FE 5E 08 15 A6 21 06 09 14 21
2360  07 02 1B 18 03 10 00 01 5F 00 2E 96 E6 E7 21 06
2370  09 14 21 07 00 01 02 1B 28 03 10 65 0C 92 8C 5F
2380  00 2F 0C E6 DE 5F 00 2D 6E EE DB 02 1B 38 03 10
2390  8D 44 E6 D9 63 0C 92 8C 21 00 80 6E 21 01 00 04
23A0  02 1B 48 03 10 5F 00 2D E8 6F 02 80 1E 5F 00 2D
23B0  38 5F 00 31 82 02 1B 58 03 10 9E 0B 5F 00 2C 18
23C0  5F 00 22 26 21 00 09 40 21 01 02 1B 68 03 10 01
23D0  9F 21 02 0B 84 8D 48 5F 00 2F FC 5F 00 2C 7A 02
23E0  1B 78 03 10 63 0E 80 64 21 00 09 14 21 01 00 07
23F0  21 02 0B 84 02 1B 88 03 10 8D 48 5F 00 2F FC 21
2400  08 1E 84 21 09 1E 66 21 0A 02 1B 98 03 10 1E 6E
2410  5F 00 06 B2 4D 05 80 6A 00 13 4D 05 80 6C 02 1B
2420  A8 03 10 00 0A 5F 00 2C 4C 5F 00 2C 32 8D 48 21
2430  05 00 03 02 1B B8 03 10 5F 00 21 94 5F 00 2D 48
2440  5F 00 2D 20 EE 07 5F 00 02 1B C8 03 10 2D 38 5F
2450  00 31 82 97 FE 5E 08 15 A6 21 06 09 53 02 1B D8
2460  03 10 21 07 00 04 5F 00 2E 96 E6 EB 21 06 09 53
2470  21 07 02 1B E8 03 10 00 04 65 0D 80 64 5F 00 2F
2480  0C E6 E2 21 00 00 C8 02 1B F8 03 10 21 01 00 FF
2490  21 02 00 60 21 03 00 80 5F 00 2D C6 02 1C 08 03
24A0  10 EE 21 21 00 09 5D 21 01 00 02 21 02 04 81 67
24B0  0E 02 1C 18 03 10 80 64 E6 02 21 02 04 7F 5F 00
24C0  30 64 21 00 09 57 02 1C 28 03 10 21 01 00 02 21
24D0  02 04 83 67 0E 80 64 E6 02 21 02 02 1C 38 03 10
24E0  04 62 5F 00 30 64 61 00 80 64 09 00 40 00 6F 00
24F0  02 1C 48 03 10 80 64 E8 B6 5F 00 2D 6E EE B3 65
2500  0D 80 64 21 00 02 1C 58 03 10 80 6E 21 01 00 03
2510  5F 00 2D E8 A1 29 67 0E 80 64 02 1C 68 03 10 E6
2520  08 19 08 00 FE 1B 08 00 64 0B 08 00 32 E7 01 02
2530  1C 78 03 10 A9 90 0B 09 00 D1 EF 03 0B 09 00 40
```

```
2540 EF 04 5F 00 02 1C 88 03 10 2D 38 5E 08 1B 78 6F
2550 09 80 22 4D 05 80 6A 00 13 02 1C 98 03 10 4D 05
2560 80 6C 00 0D 5F 00 2C 4C 21 04 00 00 21 05 02 1C
2570 A8 03 10 00 03 63 0E 80 64 5F 00 21 94 5F 00 2D
2580 48 5F 00 02 1C B8 03 10 2D 20 EE 07 5F 00 2D 38
2590 5F 00 31 82 97 FE 5E 08 02 1C C8 03 10 15 A6 21
25A0 06 09 B3 21 07 00 03 5F 00 2E 96 E6 EB 02 1C D8
25B0 03 10 21 06 09 B3 21 07 00 04 65 0D 80 64 5F 00
25C0 2F 0C 02 1C E8 03 10 E6 E2 21 00 00 C8 21 01 00
25D0 FF 21 02 00 48 21 03 02 1C F8 03 10 00 60 5F 00
25E0 2D C6 EE 21 21 00 09 BD 21 01 00 02 02 1D 08 03
25F0 10 21 02 04 87 67 0E 80 64 E6 02 21 02 04 85 5F
2600 00 02 1D 18 03 10 30 64 21 00 09 B7 21 01 00 02
2610 21 02 04 8B 67 0E 02 1D 28 03 10 80 64 E6 02 21
2620 02 04 7A 5F 00 30 64 61 00 80 64 02 1D 38 03 10
2630 09 00 40 00 6F 00 80 64 E8 B6 5F 00 2D 6E EE B3
2650 03 5F 00 2D E8 02 1D 58 03 10 A1 2B 67 0E 80 64
2660 E6 08 19 0A 11 B8 1B 0A 27 10 02 1D 68 03 10 0B
2670 0A 13 88 E7 01 A9 B0 0B 0B 00 0C E3 03 0B 0B 02
2680 1D 78 03 10 00 B6 E3 19 5F 00 2D 38 21 00 09 B2
2690 21 01 00 09 02 1D 88 03 10 21 02 04 75 5F 00 30
26A0 64 80 48 21 05 00 03 4D 05 02 1D 98 03 10 80 6A
26B0 00 13 4D 05 80 6C 00 0D 5F 00 2C 4C 65 0E 02 1D
26C0 A8 03 10 80 64 5E 08 1D 00 6F 0B 80 24 61 0B 80
26D0 22 0B 0B 02 1D B8 03 10 00 80 E7 06 19 0A 00 AB
26E0 16 0A 00 00 2E E0 E8 04 02 1D C8 03 10 19 0A 00
26F0 D0 01 0B 1C 20 61 0D 80 24 0B 0D 00 66 02 1D D8
2700 03 10 EB 0B 0B 0D 00 33 EB 0D 0B 0D 00 19 EB 0F
2710 21 01 02 1D E8 03 10 14 50 21 00 00 D2 E8 0E 21
2720 01 31 38 21 00 00 40 02 1D F8 03 10 E8 09 21 01
2730 24 B8 21 00 00 5F E8 04 21 01 1B BC 02 1E 08 03
2740 10 21 00 00 8C 99 0C 8D 08 96 0C 91 F8 98 C8 18
2750 08 02 1E 18 03 10 00 00 00 1B 1A 08 05 F5 E1 00
2760 10 08 02 FA F0 80 02 1E 28 03 10 E7 03 16 0A 00
2770 00 00 01 95 F8 6F 0B 80 1E 5F 00 02 1E 38 03 10
2780 31 82 9E 08 00 1A 04 01 01 43 01 01 01 A3 01 01
2790 02 1E 48 03 10 08 82 00 11 05 16 09 02 00 12 05
27A0 27 09 67 00 14 02 1E 58 03 10 04 3B 09 C7 00 11
27B0 04 2A 08 3B 00 04 04 E2 01 3C 02 1E 68 03 10 02
27C0 01 01 9C 02 01 09 44 00 18 04 4F 09 A4 00 18 02
27D0 1E 78 03 10 04 67 09 5D 00 02 04 7F 09 BD 00 02
27E0 04 85 5F 00 02 1E 88 03 10 31 70 5F 00 2C 18 21
27F0 00 08 00 21 01 02 E0 21 02 02 1E 98 03 10 0B 84
2800 8D 48 5F 00 2F FC 21 0C 00 01 5F 00 20 FC 02 1E
2810 A8 03 10 21 08 20 FA 21 09 20 BA 21 0A 20 C6 5F
2820 00 06 B2 02 1E B8 03 10 21 00 00 18 21 01 00 0F
2830 5F 00 22 0C 5F 00 2C 32 02 1E C8 03 10 5F 00 2D
2840 48 5F 00 2D 20 EE 05 5F 00 31 82 97 FE 02 1E D8
2850 03 10 5E 08 15 A6 21 00 00 80 21 01 00 E0 21 02
2860 00 10 02 1E E8 03 10 21 03 00 48 5F 00 2D C6 EE
2870 08 5F 00 22 26 5F 00 02 1E F8 03 10 07 2E 61 02
2880 80 20 5E 08 20 16 21 00 00 20 21 01 02 1F 08 03
2890 10 00 78 21 02 00 10 21 03 00 48 5F 00 2D C6 5E
28A0 0E 02 1F 18 03 10 1E C8 5F 00 2C 18 5F 00 22 26
28B0 21 00 09 C0 21 01 02 1F 28 03 10 01 1F 21 02 0B
```

```
28C0  84 8D 48 5F 00 2F FC 21 00 09 92 02 1F 38 03 10
28D0  21 05 00 04 5F 00 2C 00 21 00 09 97 21 01 00 02
28E0  02 1F 48 03 10 21 02 04 26 5F 00 30 64 5F 00 2C
28F0  7A 4D 05 80 6C 02 1F 58 03 10 00 0C 4D 05 80 6A
2900  00 12 21 05 00 04 8D 48 4D 01 02 1F 68 03 10 80
2910  20 00 00 E6 15 21 06 80 6E 21 07 80 0F 21 08 02
2920  1F 78 03 10 00 04 BA 71 08 60 21 00 09 92 21 01
2930  00 04 21 02 02 1F 88 03 10 80 6E 5F 00 30 64 4D
2940  05 80 6A 00 16 21 04 00 04 02 1F 98 03 10 5F 00
2950  2C 4C 5F 00 2C 32 5F 00 21 94 21 00 00 01 02 1F
2960  A8 03 10 5F 00 21 F4 5F 00 2D 48 5F 00 2D 20 EE
2970  07 5F 00 02 1F B8 03 10 2D 38 5F 00 31 82 97 FE
2980  5E 08 15 A6 21 06 09 92 02 1F C8 03 10 21 07 00
2990  02 5F 00 2E 96 E6 E7 21 06 09 92 21 07 02 1F D8
29A0  03 10 00 02 65 0C 92 8C 5F 00 2F 0C E6 DE 5F 00
29B0  2D 6E 02 1F E8 03 10 EE DB 8D 44 E6 D9 63 0C 92
29C0  8C 21 06 80 0F 21 07 02 1F F8 03 10 80 6E 21 08
29D0  00 04 BA 71 08 60 5F 00 2D 38 21 00 02 20 08 03
29E0  10 80 0F 21 01 00 04 5F 00 2D E8 6F 02 80 20 5F
29F0  00 02 20 18 03 10 21 7A 21 01 80 1C 2F 13 5F 00
2A00  31 82 9E 08 5F 00 02 20 28 03 10 2C 18 21 00 09
2A10  C0 21 01 01 1F 21 02 0B 84 8D 48 02 20 38 03 10
2A20  5F 00 2F FC 21 00 09 C5 21 01 00 19 21 02 04 C9
2A30  02 20 48 03 10 5F 00 30 64 5F 00 2C 7A 4D 05 80
2A40  6A 00 14 4D 05 02 20 58 03 10 80 6C 00 0E 21 05
2A50  00 04 8D 48 5F 00 2C 4C 5F 00 02 20 68 03 10 2C
2A60  32 5F 00 2D 48 5F 00 2D 20 EE 05 5F 00 2D 38 02
2A70  20 78 03 10 5F 00 31 82 97 FE 21 06 09 D4 21 07
2A80  00 02 5F 00 02 20 88 03 10 2E 96 E6 EF 21 06 09
2A90  D4 21 07 00 02 5F 00 2F 0C 02 20 98 03 10 E6 E8
2AA0  5F 00 2D 6E EE E5 21 00 80 6E 21 01 00 04 02 20
2AB0  A8 03 10 5F 00 2D E8 6F 07 80 26 65 0D 80 64 5F
2AC0  00 31 82 02 20 B8 03 10 9E 08 00 1A 04 01 02 25
2AD0  07 02 02 31 08 02 08 82 02 20 C8 03 10 00 11 05
2AE0  16 09 02 00 11 05 27 09 82 00 0F 05 39 02 20 D8
2AF0  03 10 09 E4 00 15 04 B4 08 3B 00 04 04 E2 0A 46
2B00  00 07 02 20 E8 03 10 04 8D 0A 66 00 07 04 94 0A
2B10  52 00 08 04 9B 0A 73 02 20 F8 03 10 00 06 04 A3
2B20  21 00 08 94 21 01 00 0B 21 02 80 00 02 21 08 03
2B30  10 5F 00 30 64 0B 0C 00 00 E6 33 21 00 80 1E BD
2B40  14 02 21 18 03 10 21 02 80 0B BD 32 5F 00 2E 3A
2B50  21 00 09 14 21 01 02 21 28 03 10 00 04 21 02 80
2B60  0B 5F 00 30 64 21 00 09 19 21 01 02 21 38 03 10
2B70  00 02 21 02 04 24 5F 00 30 64 0B 0C 00 01 E4 18
2B80  02 21 48 03 10 21 00 09 97 21 01 00 02 21 02 04
2B90  26 5F 00 30 64 02 21 58 03 10 21 00 80 20 BD 15
2BA0  21 02 80 0F BD 32 5F 00 2E 3A 02 21 68 03 10 21
2BB0  00 09 92 21 01 00 04 21 02 80 0F 5F 00 30 64 02
2BC0  21 78 03 10 9E 08 91 F0 A1 23 99 22 5B 00 21 8C
2BD0  5A 00 21 90 02 21 88 03 10 95 F0 9E 08 00 00 7A
2BE0  88 17 D7 84 00 5F 00 31 70 02 21 98 03 10 8D 44
2BF0  EE 17 5F 00 2C 18 21 00 0A 1A 21 01 00 03 02 21
2C00  A8 03 10 21 02 0B 84 5F 00 2F FC 21 00 0A 3A 5F
2C10  00 2F FC 02 21 B8 03 10 21 00 0A 5A 5F 00 2F FC
2C20  5F 00 2C 4C 5F 00 2C 32 02 21 C8 03 10 E8 0C 5F
```

```
2C30  00 2C 18 21 08 21 F0 21 09 21 E8 21 0A 02 21 D8
2C40  03 10 21 EC 5F 00 06 B2 5F 00 2C 32 5F 00 31 82
2C50  9E 08 02 21 E8 03 10 02 1A 01 01 0A 3B 00 01 21
2C60  F2 61 00 8D 04 EE 07 02 21 F8 03 10 21 00 09 15
2C70  21 03 00 25 5F 00 30 7C 9E 08 21 00 02 22 08 03
2C80  10 09 94 E8 F8 6F 00 80 6A 6F 01 80 6C 5F 00 2C
2C90  4C 02 22 18 03 10 21 00 0B 87 21 03 00 01 5F 00
2CA0  30 7C 9E 08 63 0F 02 22 28 03 10 80 64 21 00 0B
2CB0  87 21 03 00 08 5F 00 30 7C 9E 08 02 22 38 03 10
2CC0  5F 00 31 70 21 02 23 EA E8 04 5F 00 31 70 21 02
2CD0  02 22 48 03 10 23 B2 14 20 8C 84 E6 0E A7 0F E6
2CE0  03 A3 0F 8D 48 02 22 58 03 10 1F 10 8D 68 21 05
2CF0  00 13 61 03 70 00 A7 3F E6 05 02 22 68 03 10 F6
2D00  85 F5 86 5F 00 31 82 9E 08 20 1C 6F 04 70 00 02
2D10  22 78 03 10 A9 10 F0 91 A9 23 E8 E5 91 F2 91 F4
2D20  8D 58 21 01 02 22 88 03 10 80 6E 21 02 80 00 70
2D30  2B 05 00 8C B4 E6 14 21 04 02 22 98 03 10 00 40
2D40  0A 0B 1A 1A E3 12 21 04 00 15 0A 0B 24 24 02 22
2D50  A8 03 10 E3 0D 21 04 00 09 0A 0B 25 25 E6 08 21
2D60  04 00 07 02 22 B8 03 10 0A 0B 26 26 E6 03 21 03
2D70  00 20 8D 48 80 CB 72 1B 02 22 C8 03 10 05 00 A9
2D80  50 8B 05 EE DF 95 F4 95 F2 9E 08 61 0D 02 22 D8
2D90  03 10 93 2A 19 0C 00 64 E8 1B 61 0D 93 28 E8 17
2DA0  61 0D 02 22 E8 03 10 80 1E E8 1D 61 0D 93 26 E8
2DB0  11 61 0D 93 20 E8 0E 02 22 F8 03 10 61 0D 93 24
2DC0  E8 0B 61 0D 80 20 E8 08 61 0D 93 22 02 23 08 03
2DD0  10 E8 05 61 0D 93 1E 19 0C 00 64 E8 01 8D C8 1B
2DE0  0C 02 23 18 03 10 00 0A 0B 00 00 03 EE 03 8D C8
2DF0  1B 0C 00 0A 21 01 02 23 28 03 10 80 6E 91 F0 91
2E00  F2 4D 05 80 6E 20 20 8D C8 1B 0C 02 23 38 03 10
2E10  00 0A 01 0C 00 30 5F 00 23 70 AB 00 0B 00 00 03
2E20  02 23 48 03 10 EE 05 21 0C 00 2E 5F 00 23 70 F0
2E30  90 0B 0D 00 00 02 23 58 03 10 EE ED 0B 00 00 00
2E40  E2 05 21 0C 00 20 5F 00 23 70 02 23 68 03 10 F0
2E50  85 95 F2 95 F0 9E 08 91 F0 A1 C2 21 00 00 05 02
2E60  23 78 03 10 2C 1A A9 10 F0 83 95 F0 9E 08 93 F0
2E70  21 01 80 6E 02 23 88 03 10 5F 00 26 8C 21 00 00
2E80  2D 32 18 00 02 32 18 00 05 02 23 98 03 10 97 F0
2E90  9E 08 93 F0 21 01 80 6E 5F 00 27 2E 21 00 02 23
2EA0  A8 03 10 00 3A 32 18 00 02 97 F0 9E 08 00 13 24
2EB0  B5 80 03 02 23 B8 03 10 22 D6 00 12 24 47 80 03
2EC0  23 0A 00 13 24 A0 80 03 02 23 C8 03 10 22 EC 00
2ED0  11 24 6C 80 04 22 E0 00 13 24 59 80 03 02 23 D8
2EE0  03 10 22 F2 00 12 24 8E 80 03 23 04 00 11 24 7D
2EF0  80 04 02 23 E8 03 10 22 F8 00 12 24 35 80 04 22
2F00  FE 00 05 24 2B 80 05 02 23 F8 03 10 22 E6 00 05
2F10  24 30 00 04 24 27 80 0B 22 80 00 01 02 24 08 03
2F20  10 24 B3 00 01 24 B3 80 08 23 82 00 07 24 20 80
2F30  05 02 24 18 03 10 23 9C 00 02 24 B3 00 00 20 20
2F40  20 20 20 20 20 0D 02 24 28 03 10 49 44 20 0D 42
2F50  53 41 20 20 53 51 20 4D 0D 0D 41 02 24 38 03 10
2F60  4F 52 54 49 43 20 44 49 41 4D 45 54 45 52 20 0D
2F70  02 24 48 03 10 53 49 47 4E 41 4C 20 4C 45 56 45
2F80  4C 20 20 20 20 02 24 58 03 10 20 0D 0D 48 45 41
2F90  52 54 20 52 41 54 45 20 20 20 02 24 68 03 10 20
```

```
2FA0 20 20 20 0D 43 41 52 44 49 41 43 20 49 4E 44 02
2FB0 24 78 03 10 45 58 20 20 20 0D 43 41 52 44 49 41
2FC0 43 20 4F 55 02 24 88 03 10 54 50 55 54 20 20 0D
2FD0 53 54 52 4F 4B 45 20 56 4F 02 24 98 03 10 4C 55
2FE0 4D 45 20 20 20 20 0D 0D 53 54 52 4F 4B 45 02 24
2FF0 A8 03 10 20 49 4E 44 45 58 20 20 20 20 20 0D 0C
3000 0D 0D 45 02 24 B8 03 10 4A 45 43 54 20 54 49 4D
3010 45 20 20 20 20 20 20 20 02 93 3C 03 04 00 00 00
3020 00 02 93 55 03 0B 00 00 00 00 00 00 00 00 00 00
3030 00 02 93 85 03 01 00 02 93 8F 03 01 00 02 93 99
3040 03 01 00 02 24 C8 03 10 24 CE 24 CE 24 CE 24 DA
3050 24 FA 26 4E 00 00 00 38 02 24 D8 03 10 00 00 00
3060 05 00 82 00 04 26 5C 00 A7 00 08 26 6E 02 24 E8
3070 03 10 01 02 00 04 26 60 01 43 00 05 26 68 01 49
3080 00 05 02 24 F8 03 10 26 76 00 0D 25 4A 25 98 10
3090 C4 25 50 25 B4 29 00 02 25 0B 03 10 25 56 25 C2
30A0 29 0B 25 5C 25 D0 29 10 25 62 25 DE 02 25 18 03
30B0 10 29 18 25 68 25 EC 29 20 25 6E 26 32 29 DE 25
30C0 74 02 25 28 03 10 25 FA 29 28 25 7A 26 08 29 30
30D0 25 80 26 16 29 38 02 25 38 03 10 25 86 26 24 29
30E0 40 25 8C 25 A6 2B F8 25 92 26 40 02 25 48 03 10
30F0 2A 3E 00 1A C0 FF 98 BF 02 01 00 24 25 48 02 05
3100 02 25 58 03 10 25 44 25 48 02 09 45 64 25 48 02
3110 0D 65 84 25 48 02 25 68 03 10 02 11 85 A4 25 48
3120 02 1D C4 FF 24 46 02 81 00 24 02 25 78 03 10 00
3130 24 02 85 25 44 00 24 02 89 45 64 00 24 02 8D 02
3140 25 88 03 10 65 84 00 24 02 91 85 A4 00 24 02 99
3150 C4 FF 00 23 02 25 98 03 10 06 03 00 21 00 04 26
3160 64 00 00 00 00 00 00 03 03 02 25 A8 03 10 00 21
3170 00 01 26 81 00 00 00 00 00 00 03 03 00 21 02 25
3180 B8 03 10 00 01 26 82 00 00 00 00 00 00 03 03 00
3190 21 00 01 02 25 C8 03 10 26 83 00 00 00 00 00 00
31A0 03 03 00 21 00 01 26 84 02 25 D8 03 10 00 00 00
31B0 00 00 00 03 03 00 21 00 01 26 85 00 00 02 25 E8
31C0 03 10 00 00 00 03 03 00 21 00 01 26 86 00 00
31D0 00 00 02 25 F8 03 10 00 00 03 03 00 21 00 01 26
31E0 87 00 00 00 00 00 00 02 26 08 03 10 03 03 00 21
31F0 00 01 26 88 00 00 00 00 00 00 03 03 02 26 18 03
3200 10 00 21 00 01 26 89 00 00 00 00 00 00 03 03 00
3210 21 02 26 28 03 10 00 01 26 8A 00 00 00 00 00 00
3220 03 03 00 21 00 01 02 26 38 03 10 26 7B 00 00 00
3230 00 00 00 07 03 00 21 00 05 26 7C 02 26 48 03 10
3240 00 00 00 00 00 00 00 02 00 87 00 08 28 9C 01 09
3250 02 26 58 03 10 00 05 28 C8 44 41 54 45 54 49 4D
3260 45 4D 45 4E 55 02 26 68 03 10 32 34 20 48 52 20
3270 4D 4F 20 44 41 20 59 52 43 4C 02 26 78 03 10 4F
3280 43 4B A9 45 4E 54 45 52 30 31 32 33 34 35 36 02
3290 26 88 03 03 37 38 39 02 26 8C 03 10 5F 00 31 70
32A0 5F 00 26 B0 A1 14 21 01 93 4D 5F 00 02 26 9C 03
32B0 10 26 B0 A1 42 BD 38 BA 26 03 1E A1 41 E6 F3 5F
32C0 00 02 26 AC 03 10 31 82 9E 08 5F 00 31 70 8D 48
32D0 21 02 27 26 21 23 02 26 BC 03 10 8D 58 21 30 07
32E0 00 00 0F 0B 00 00 09 E3 04 F5 87 02 26 CC 03 10
32F0 5F 00 14 70 BD 08 01 00 00 30 2E 18 A9 21 A9 10
3300 02 26 DC 03 10 A9 40 0B 04 00 02 EE 03 0C 15 A6
```

```
3310  A6 E8 F8 0B 04 02 26 EC 03 10 00 05 E7 E5 0C 15
3320  A6 A6 8D 28 61 03 60 08 8C 38 02 26 FC 03 10 1B
3330  02 00 0A 0B 03 00 09 E3 05 14 02 00 00 00 00 02
3340  27 0C 0A 10 5F 00 14 70 01 02 00 30 01 03 00 30
3350  32 1B 00 01 02 27 1C 03 10 32 1A 00 02 5F 00 31
3360  82 9E 08 6C 18 6C 16 6C 12 02 27 2C 03 10 6C 10
3370  5F 00 31 70 5F 00 27 52 A1 14 21 01 93 4D 02 27
3380  3C 03 10 5F 00 27 52 A1 42 BD 35 BA 26 03 1E A1
3390  41 E6 F3 02 27 4C 03 10 5F 00 31 82 9E 08 5F 00
33A0  31 70 8D 48 21 02 27 98 02 27 5C 03 10 21 23 8D
33B0  58 21 30 07 00 00 0F 0B 00 00 0F EE 04 02 27 6C
33C0  03 10 F5 87 5F 00 14 70 8D 08 01 00 00 30 2E 18
33D0  A9 21 02 27 7C 03 10 A9 10 A9 40 0B 04 00 02 EE
33E0  03 0C 15 A7 A7 E8 F8 02 27 8C 03 10 0B 04 00 05
33F0  E7 E5 5F 00 31 82 9E 08 6C 0E 6C 0C 02 27 9C 03
3400  10 6C 0A 6C 08 8D 08 5F 00 31 70 5F 00 31 90 A1
3410  04 02 27 AC 03 10 A9 12 5F 00 31 90 A1 05 A9 12
3420  5F 00 31 90 0B 00 02 27 BC 03 10 00 63 EB 1A 8D
3430  44 E6 18 0B 04 00 0C EB 15 8D 54 02 27 CC 03 10
3440  E6 13 21 06 27 FE 8D 38 70 6B 04 00 8B 35 E3 0E
3450  02 27 DC 03 10 0B 04 00 02 EE 09 0B 05 00 1D EE
3460  06 A1 01 8D 08 02 27 EC 03 10 1B 00 00 04 8D 04
3470  E6 02 69 F0 00 00 5F 00 31 82 02 27 FC 03 10 9E
3480  08 00 1F 1C 1F 1E 1F 1E 1F 1F 1E 1F 1E 1F 00 02
3490  28 0C 03 10 8D 08 5F 00 31 70 5F 00 31 90 0B 00
34A0  00 17 EB 06 02 28 1C 03 10 A9 12 5F 00 31 90 0B
34B0  00 00 3B E3 02 69 F0 00 00 02 28 2C 03 10 5F 00
34C0  31 82 9E 08 91 F0 8D 08 20 18 03 00 00 30 02 28
34D0  3C 03 08 21 21 2F 10 95 F0 9E 08 02 28 44 03 10
34E0  91 F2 5F 00 0E D2 5F 00 28 74 21 02 24 C8 61 22
34F0  02 28 54 03 10 00 04 21 03 93 3E 5F 00 0F 00 5F
3500  00 0F 3A 5F 00 02 28 64 03 10 10 74 5F 00 0F CE
3510  27 30 E6 FA 23 30 95 F2 9E 08 02 28 74 03 10 93
3520  F1 21 01 93 40 5F 00 26 8C 21 01 93 48 5F 00 02
3530  28 84 03 10 27 2E 21 01 93 3E 23 13 25 14 25 15
3540  4D 08 93 58 02 28 94 03 10 5F 00 2B 54 97 F1 9E
3550  08 5F 00 31 70 21 01 24 C8 02 28 A4 03 10 61 11
3560  00 04 61 17 00 04 61 77 00 02 01 07 08 00 02 28
3570  B4 03 10 61 18 00 0A 21 09 93 40 BD A8 5F 00 31
3580  14 5F 00 02 28 C4 03 10 31 82 9E 08 5F 00 31 70
3590  21 01 24 C8 61 11 00 04 02 28 D4 03 10 61 17 00
35A0  04 01 07 00 06 61 77 00 02 01 07 08 00 02 28 E4
35B0  03 10 61 18 00 0A 21 09 93 48 BD A5 5F 00 31 14
35C0  5F 00 02 28 F4 03 10 31 82 9E 08 4D 05 93 56 00
35D0  00 E8 24 4D 05 93 56 02 29 04 03 10 00 01 E8 20
35E0  4D 05 93 56 00 02 E8 1C 4D 05 93 56 02 29 14 03
35F0  10 00 03 E8 18 4D 05 93 56 00 04 E8 14 4D 05 93
3600  56 02 29 24 03 10 00 05 E8 10 4D 05 93 56 00 06
3610  E8 0C 4D 05 93 56 02 29 34 03 10 00 07 E8 08 4D
3620  05 93 56 00 08 E8 04 4D 05 93 56 02 29 44 03 10
3630  00 09 E8 00 5F 00 31 70 61 04 93 58 67 03 93 3E
3640  02 29 54 03 10 EE 1D 0B 04 00 08 E6 37 21 01 93
3650  40 8D 44 EE 06 02 29 64 03 10 21 02 29 D0 BD 38
3660  A1 15 BA 21 03 50 61 00 93 56 02 29 74 03 10 01
3670  00 00 30 72 18 04 00 A9 40 69 00 80 6A 0B 04 02
```

```
3680  29 84 03 10 00 02 E6 FA 0B 04 00 05 E6 F7 E8 19
3690  0B 04 00 05 02 29 94 03 10 E6 1A 21 01 93 48 8D
36A0  44 EE 06 21 02 29 D8 BD 35 02 29 A4 03 10 A1 15
36B0  BA 21 03 50 61 00 93 56 01 00 00 30 72 18 02 29
36C0  B4 03 10 04 00 A9 40 69 00 80 6A 0B 04 00 02 E6
36D0  FA 6F 04 02 29 C4 03 10 93 58 5F 00 2C 4C 5F 00
36E0  31 82 9E 08 A9 A9 A6 A9 02 29 D4 03 10 A9 A6 A9
36F0  A9 A9 A9 A7 A9 A9 00 5F 00 31 70 61 04 02 29 E4
3700  03 10 93 58 8D 44 E6 27 AB 40 6B 00 80 6A 67 03
3710  93 3E 02 29 F4 03 10 E6 06 21 01 93 48 0B 04 00
3720  04 E6 06 E8 0D 21 01 02 2A 04 03 10 93 40 0B 04
3730  00 07 EE 05 6F 04 93 58 5F 00 2B 54 02 2A 14 03
3740  10 E8 0B 0B 04 00 05 E6 03 0B 04 00 02 EE 03 AB
3750  40 02 2A 24 03 10 6B 00 80 6A 6F 04 93 58 21 00
3760  00 A9 72 18 04 00 02 2A 34 03 10 5F 00 2C 4C 5F
3770  00 31 82 9E 08 5F 00 31 70 61 00 02 2A 44 03 10
3780  93 58 67 03 93 3E EE 49 21 01 93 40 8D 04 E6 40
3790  02 2A 54 03 10 0B 00 00 08 EE 70 5F 00 27 A0 8D
37A0  04 EE 33 8D 08 02 2A 64 03 10 21 02 2B 44 4D 08
37B0  6C 1C A1 13 5F 00 28 32 A9 21 02 2A 74 03 10 A9
37C0  00 A9 10 0B 00 00 02 E6 FB 0B 00 00 05 E7 F5 02
37D0  2A 84 03 10 8D 08 30 38 00 06 03 00 00 30 B3 09
37E0  00 01 A1 01 02 2A 94 03 10 B3 09 00 02 81 01 8D
37F0  08 30 38 00 07 03 00 00 30 02 2A A4 03 10 81 01
3800  6F 01 60 08 8D 08 1B 00 00 04 21 01 2B 40 02 2A
3810  B4 03 10 A1 02 70 18 02 00 6F 00 6C 1A 65 04 93
3820  3E 5F 00 02 2A C4 03 10 14 56 E8 08 21 02 29 D0
3830  BD 38 BA 21 03 10 E8 2F 02 2A D4 03 10 5F 00 26
3840  0C 65 03 93 3E E6 2A 21 01 93 48 8D 04 02 2A E4
3850  03 10 E6 22 0B 00 00 05 EE 27 5F 00 28 0C 8D 04
3860  EE 15 02 2A F4 03 10 8D 08 21 02 2B 4C 4D 08 6C
3870  1C 5F 00 28 32 A9 21 02 2B 04 03 10 A9 00 A9 10
3880  0B 00 00 02 E6 FB 0B 00 00 05 E7 F5 02 2B 14 03
3890  10 65 05 93 3E 5F 00 14 56 E8 08 21 02 29 D8 BD
38A0  35 02 2B 24 03 10 BA 21 03 10 E8 04 5F 00 27 2E
38B0  63 03 93 3E 4D 08 02 2B 34 03 10 93 58 5F 00 2B
38C0  54 5F 00 31 82 9E 08 08 01 02 04 02 2B 44 03 10
38D0  6C 18 6C 16 6C 12 6C 10 6C 0E 6C 0C 6C 0A 6C 08
38E0  02 2B 54 03 10 91 F0 21 01 24 C8 61 11 00 04 61
38F0  11 00 04 67 03 02 2B 64 03 10 93 3E E6 02 01 01
3900  00 06 61 11 00 02 41 01 93 58 02 2B 74 03 10 8D
3910  08 1B 00 00 20 6F 00 80 6A 6F 01 80 6C 5F 00 02
3920  2B 84 03 06 2C 4C 95 F0 9E 08 02 2B 8A 03 10 5C
3930  09 00 0E 92 6E 01 00 08 00 A1 0D 21 03 00 D3 02
3940  2B 9A 03 10 5F 00 30 7C 21 03 00 CE A9 00 5F 00
3950  30 94 81 10 02 2B AA 03 10 21 03 00 D5 5F 00 30
3960  7C 01 0D 00 20 A1 D0 21 03 02 2B BA 03 10 00 D0
3970  5F 00 30 7C 21 03 00 38 A9 00 5F 00 30 94 02 2B
3980  CA 03 10 81 10 21 03 00 D1 5F 00 30 7C F2 92 01
3990  0D 00 20 02 2B DA 03 10 A1 D0 21 03 00 D4 5F 00
39A0  30 7C 21 03 00 CF A9 00 02 2B EA 03 10 5F 00 30
39B0  94 81 10 21 03 00 D2 5F 00 30 7C 5C 01 02 2B FA
39C0  03 10 00 0E 92 6E 9E 08 93 F1 93 F3 8D 54 E6 05
39D0  A1 51 02 2C 0A 03 10 21 03 00 29 5F 00 30 94 97
39E0  F3 97 F1 9E 08 4D 05 02 2C 1A 03 10 64 02 80 00
```

```
39F0  4D 05 64 04 00 80 4D 05 64 04 00 81 02 2C 2A 03
3A00  10 4D 05 64 02 00 00 9E 08 4D 05 64 02 80 00 4D
3A10  05 02 2C 3A 03 10 64 04 00 C0 4D 05 64 04 00 81
3A20  4D 05 64 02 00 00 02 2C 4A 03 10 9E 08 93 F0 93
3A30  F3 21 00 0B 84 61 03 80 6C B3 39 02 2C 5A 03 10
3A40  00 03 AB 30 5F 00 30 7C A9 00 61 03 80 6A B3 39
3A50  02 2C 6A 03 10 00 03 5F 00 30 7C 65 0F 80 64 97
3A60  F3 97 F0 9E 08 02 2C 7A 03 10 5F 00 31 70 21 08
3A70  2D 00 21 09 2C 94 21 0A 2C C0 02 2C 8A 03 10 5F
3A80  00 06 B2 5F 00 31 82 9E 08 02 01 01 01 02 05 02
3A90  2C 9A 03 10 01 01 02 09 01 01 02 0D 01 01 02 11
3AA0  01 01 02 81 02 2C AA 03 10 01 01 02 85 01 01 02
3AB0  89 01 01 02 8D 01 01 02 91 02 2C BA 03 10 01 01
3AC0  02 99 05 01 0A 22 00 01 2D 02 0A 26 00 01 02 2C
3AD0  05 0A 32 02 2C DA 03 10 00 01 2D 06 0A A2 00 01
3AE0  2D 07 0A A6 00 01 2D 08 02 2C EA 03 10 0A AA 00
3B00  01 2D 09 0A AE 00 01 2D 0A 0A B2 00 01 02 2C FA
3B10  03 10 2D 0B 0A B6 00 05 04 F7 54 55 56 57 58 59
3B20  5A 5B 02 2D 0A 03 10 5C 53 A1 70 21 01 00 01 21
3B30  02 00 01 5F 00 2B 8A 02 2D 1A 03 10 A9 73 F8 89
3B40  9E 08 0B 0A 00 C0 E7 07 0B 0B 00 98 02 2D 2A 03
3B50  10 E7 04 8D 41 61 00 64 02 9E 08 8D 43 9E 08 21
3B60  00 02 2D 3A 03 10 00 0B 21 01 80 6E 0C 18 A9 10
3B70  F0 83 9E 08 65 05 02 2D 4A 03 10 80 66 61 0A 80
3B80  80 07 0A 00 FF E6 F9 8D B8 7C 01 02 2D 5A 03 10
3B90  4D 08 80 80 6D 0B 80 82 7C 05 07 0B 00 FF 63 05
3BA0  02 2D 6A 03 10 80 66 9E 08 0B 0A 00 C4 E7 0C 0B
3BB0  0B 00 00 E7 09 02 2D 7A 03 10 0B 0B 00 23 EB 06
3BC0  8D 41 61 00 64 02 63 0D 80 64 02 2D 8A 03 10 9E
3BD0  08 8D 43 9E 08 5F 00 31 70 61 08 2D C4 61 09 02
3BE0  2D 9A 03 10 2D AA 61 0A 2D AE 5F 00 06 B2 5F 00
3BF0  31 82 9E 08 02 2D AA 03 10 00 1A 04 01 08 3B 00
3C00  04 04 E2 08 82 00 11 05 16 02 2D BA 03 10 09 02
3C10  00 0C 80 1E 09 82 00 0F 05 39 8B 0A E7 0D 02 2D
3C20  CA 03 10 8B 1A EB 0B 8B 2B E7 09 8B 3B EB 07 67
3C30  07 92 8C 02 2D DA 03 10 EE 02 61 00 64 02 8D 41
3C40  9E 08 8D 43 9E 08 91 F4 02 2D EA 03 10 91 F6 A1
3C50  06 8D 28 8D 44 E6 1B A1 45 0C 61 25 25 02 2D FA
3C60  03 10 E6 1A A1 27 B3 79 00 01 B3 29 00 03 81 72
3C70  8D 54 02 2E 0A 03 10 E2 07 8D 78 20 6F 8D 74 E6
3C80  02 03 07 00 1B 81 72 02 2E 1A 03 10 A9 60 AB 50
3C90  F4 95 67 0D 80 64 E6 05 63 0D 80 64 02 2E 2A 03
3CA0  10 95 F6 95 F4 9E 08 65 0D 80 64 21 04 00 03 E8
3CB0  F0 02 2E 3A 03 10 A1 08 21 89 8D 88 A1 2A 81 1A
3CC0  AB A0 A1 AB 1B 08 02 2E 4A 03 10 00 0A 01 08 00
3CD0  1B AD 08 2E A9 AD 80 8D 88 AB A0 02 2E 5A 03 10
3CE0  AB 10 AB 30 0B 03 00 00 EE 03 0C A5 25 25 E8 F7
3CF0  02 2E 6A 03 10 0B 01 00 00 EB 0A 0B 09 00 00 9E
3D00  06 A1 29 0C 95 02 2E 7A 03 10 24 24 A9 90 8B B9
3D10  E7 FB 9E 08 0B 03 FF FF E9 DF 02 2E 8A 03 10 0B
3D20  09 00 00 EE DC 0C A5 00 00 E8 E1 0B 0A 00 C4 02
3D30  2E 9A 03 10 E7 0A 0B 0A 00 FF EB 07 0B 0B 00 24
3D40  E7 04 0B 0B 02 2F AA 03 10 00 46 EB 01 F8 0. 8D
3D50  43 9E 0E 0B 04 00 00 9E 06 02 2E BA 03 10 8D 08
3D60  A1 41 AB 10 60 1B 80 6F 4C 15 80 6E 00 00 02 2E
```

```
3D70 CA 03 10 A1 71 91 F0 6B 00 80 6A 5F 00 2C 4C A1
3D80 60 A1 41 02 2E DA 03 10 21 02 80 6E 5F 00 30 64
3D90 AB 40 A1 60 81 40 BD 11 02 2E EA 03 10 21 02 2F
3DA0 0A 5F 00 30 64 95 F0 0A 08 25 25 EE 04 02 2E FA
3DB0 03 10 63 0D 80 64 8B 14 E6 DC 61 00 64 02 8D 41
3DC0 9E 08 02 2F 0A 03 10 29 29 0B 0B 00 48 EB 12 0B
3DD0 0B 00 00 E7 0F 0B 0A 02 2F 1A 03 10 00 00 E7 0C
3DE0 8B 54 EF 0A 0B 0B 00 24 EF 47 0B 0A 02 2F 2A 03
3DF0 10 00 23 EB 06 4C 45 80 6E 21 21 E8 2C 0D 43 9E
3E00 08 02 2F 3A 03 10 0B 0A 00 43 EB 04 4C 45 80 6E
3E10 22 22 E8 23 0B 0A 02 2F 4A 03 10 00 63 EB 04 4C
3E20 45 80 6E 23 23 E8 1C 0B 0A 00 83 02 2F 5A 03 10
3E30 EB 04 4C 45 80 6E 24 24 E8 15 0B 0A 00 A3 EB 04
3E40 02 2F 6A 03 10 4C 45 80 6E 1B 1B E8 0E 0B 0A 00
3E50 C3 EB DF 67 0C 02 2F 7A 03 10 92 8C EE DC 67 0D
3E60 80 64 EE D9 65 0D 80 64 4C 45 02 2F 8A 03 10 80
3E70 6E 25 25 A9 40 69 00 80 6A 67 0D 80 64 EE 02 02
3E80 2F 9A 03 10 8B 74 E6 F0 5F 00 2C 4C A1 60 A1 41
3E90 21 02 80 6E 02 2F AA 03 10 5F 00 30 64 8D 41 61
3EA0 00 64 02 9E 08 0B 0A 00 23 02 2F BA 03 10 EB 04
3EB0 4C 45 80 6E 1C 1C E8 E5 0B 0A 00 43 EB 04 02 2F
3EC0 CA 03 10 4C 45 80 6E 1D 1D E8 DE 0B 0A 00 63 EB
3ED0 04 4C 45 02 2F DA 03 10 80 6E 1E 1E E8 D7 0B 0A
3EE0 00 83 EB 04 4C 45 80 6E 02 2F EA 03 10 1F 1F E8
3EF0 D0 0B 0A 00 A3 EB A1 4C 45 80 6E 20 20 02 2F FA
3F00 03 10 E8 C9 93 F0 93 F3 A1 43 5F 00 30 94 A1 20
3F10 21 03 02 30 0A 03 10 00 D0 5F 00 30 7C 97 F3 97
3F20 F0 9E 08 21 00 00 30 02 30 1A 03 10 21 01 00 7F
3F30 21 02 00 00 21 03 00 2F 5F 00 2D C6 02 30 2A 03
3F40 10 9E 08 21 00 00 80 21 01 00 C4 21 02 00 00 21
3F50 03 02 30 3A 03 10 00 2F 5F 00 2D C6 9E 08 21 00
3F60 0A E1 21 01 00 02 02 30 4A 03 10 21 02 05 1E 5F
3F70 00 30 64 21 00 0A E4 21 01 00 0B 02 30 5A 03 10
3F80 21 02 80 00 5F 00 30 64 9E 08 93 F4 21 04 64 04
3F90 02 30 6A 03 10 DF E6 97 F4 9E 08 93 F4 21 04 64
3FA0 00 DF DC 97 F4 02 30 7A 03 10 9E 08 93 F4 21 04
3FB0 64 04 DF E2 97 F4 9E 08 93 F4 02 30 8A 03 10 21
3FC0 04 64 00 DF EE 97 F4 9E 08 93 F4 21 04 64 04 02
3FD0 30 9A 03 10 DF F4 97 F4 9E 08 91 F0 91 F2 20 2B
3FE0 DF F4 A9 20 02 30 AA 03 10 A9 00 F1 85 95 F2 95
4000 95 F0 9E 08 95 F0 A5 0E 7D E2 7C 01 4D 05 02 30
4010 CA 03 10 44 02 80 00 2F 40 AC 08 2F 40 4D 05 64
4020 02 00 00 02 30 DA 03 08 2F 43 7D EA 97 F0 9E 08
4030 02 30 E2 03 10 91 F0 93 F2 7D 22 7C 01 4D 05 64
4040 02 80 00 21 01 02 30 F2 03 10 93 3C 21 11 BD 00
4050 A0 F8 2F 10 A0 78 05 00 00 40 02 31 02 03 10 2F
4060 10 4D 05 64 02 00 00 2F 16 7D 2A 97 F2 95 F0 02
4070 31 12 03 10 9E 08 DF D3 DF FA D0 1C A9 70 A9 90
4080 FA 85 DF D0 02 31 22 03 10 9E 08 8D 08 20 98 A7
4090 07 E6 04 07 00 00 7F 8D 68 02 31 32 03 10 E8 14
40A0 21 06 FF EB 0B 00 00 30 E7 0B 00 00 39 02 31
40B0 42 03 10 E3 0C 21 06 FF C0 0B 00 00 41 E7 03 0B
40C0 00 00 5A 02 31 52 03 10 E3 04 21 06 FF E0 21 00
40D0 00 20 81 06 81 86 9E 08 02 31 62 03 10 93 F6 01
40E0 06 00 1B 81 86 D0 45 97 F6 9E 08 2D FE 02 31 72
```

| | | | | | | | | | | | | | | |
|---|---|---|---|---|---|---|---|---|---|---|---|---|---|---|
| 40F0 | 03 | 10 | 34 | FF | FF | E4 | 1C | F9 | 00 | 0D | 93 | FE | 61 | FE | 00 | 1E |
| 4100 | 9E | 08 | 02 | 31 | 82 | 03 | 10 | 97 | FE | 1C | F1 | 00 | 0D | 34 | FF | 00 |
| 4110 | 1C | 2D | FE | 9E | 08 | 93 | F2 | 02 | 31 | 92 | 03 | 10 | 8D | 08 | 20 | 18 |
| 4120 | 03 | 00 | 00 | 30 | 0B | 00 | 00 | 09 | EB | 0F | B3 | 09 | 02 | 31 | A2 | 03 |
| 4130 | 10 | 00 | 01 | A1 | 02 | B3 | 09 | 00 | 02 | 81 | 20 | 8D | 28 | 30 | 1A | 00 |
| 4140 | 01 | 02 | 31 | B2 | 03 | 10 | 03 | 02 | 00 | 30 | 81 | 20 | 0B | 02 | 00 | 09 |
| 4150 | E3 | 01 | 8D | 08 | 97 | F2 | 02 | 31 | C2 | 03 | 0E | 9E | 08 | 4D | 05 | 80 |
| 4160 | 6C | 00 | 1D | 5F | 00 | 2C | 4C | 9E | 08 | 02 | 31 | D0 | 03 | 10 | 4D | 05 |
| 4170 | 80 | 66 | 00 | 04 | 8D | 88 | 21 | 07 | 0A | 37 | 21 | 06 | 93 | 1C | 02 | 31 |
| 4180 | E0 | 03 | 10 | 93 | 68 | 0B | 06 | 92 | CE | EB | FC | 93 | 67 | AB | 70 | 0B |
| 4190 | 06 | 92 | 9E | 02 | 31 | F0 | 03 | 10 | EB | FB | 4D | 05 | 92 | 9C | 92 | CC |
| 41A0 | 4D | 05 | 93 | 02 | 93 | 04 | 5F | 00 | 02 | 32 | 00 | 03 | 10 | 2C | 18 | 21 |
| 41B0 | 00 | 08 | 00 | 21 | 01 | 02 | E0 | 8D | 48 | 21 | 02 | 0B | 84 | 02 | 32 | 10 |
| 41C0 | 03 | 10 | 5F | 00 | 2F | FC | 21 | 00 | 08 | 78 | 21 | 01 | 00 | 0F | 21 | 08 |
| 41D0 | 00 | 2F | 02 | 32 | 20 | 03 | 10 | 21 | 09 | 00 | 2F | 5F | 00 | 34 | F2 | 21 |
| 41E0 | 00 | 0A | 40 | 21 | 06 | 00 | 08 | 02 | 32 | 30 | 03 | 10 | 21 | 05 | 00 | 30 |
| 41F0 | 21 | 03 | 00 | 30 | 21 | 04 | 00 | 30 | 5F | 00 | 35 | 20 | 02 | 32 | 40 | 03 |
| 4200 | 10 | 21 | 08 | 33 | 56 | 21 | 09 | 33 | 24 | 21 | 0A | 33 | 28 | 5F | 00 | 06 |
| 4210 | B2 | 02 | 32 | 50 | 03 | 10 | 5F | 00 | 2C | 32 | 65 | 00 | 80 | 90 | 4D | 05 |
| 4220 | 80 | 98 | 00 | 01 | 4D | 05 | 02 | 32 | 60 | 03 | 10 | 80 | 8E | 00 | 01 | 61 |
| 4230 | 01 | 80 | 8E | 6F | 01 | 74 | 02 | 65 | 0C | 80 | 64 | 02 | 32 | 70 | 03 | 10 |
| 4240 | 63 | 02 | 80 | 64 | 4D | 05 | 60 | 04 | 80 | 02 | 5F | 00 | 2D | 48 | 5F | 00 |
| 4250 | 02 | 32 | 80 | 03 | 10 | 2D | 20 | EE | 10 | 63 | 00 | 80 | 8E | 61 | 01 | 80 |
| 4260 | 8E | 6F | 01 | 74 | 00 | 02 | 32 | 90 | 03 | 10 | 63 | 00 | 80 | 90 | 63 | 02 |
| 4270 | 80 | 90 | 63 | 04 | 80 | 90 | 4D | 08 | 92 | 8C | 02 | 32 | A0 | 03 | 10 | 5E |
| 4290 | 32 | B0 | 03 | 10 | 00 | 1F | 21 | 02 | 00 | 00 | 21 | 03 | 00 | 24 | | 00 |
| 42A0 | 2D | C6 | FE | DD | 02 | 32 | C0 | 03 | 10 | 65 | 0E | 92 | 8C | 21 | 08 | 33 |
| 42B0 | 6C | 21 | 09 | 33 | 58 | 21 | 0A | 33 | 5C | 02 | 32 | D0 | 03 | 10 | 5F | 00 |
| 42C0 | 04 | B2 | 7C | 01 | 5F | 00 | 12 | 78 | 61 | 00 | 80 | 5A | 6F | 00 | 02 | 32 |
| 42D0 | E0 | 03 | 10 | 93 | 20 | 61 | 00 | 80 | 56 | 6F | 00 | 93 | 22 | 61 | 00 | 80 |
| 42E0 | 5C | 6F | 00 | 02 | 32 | F0 | 03 | 10 | 93 | 24 | 61 | 00 | 80 | 58 | 6F | 00 |
| 42F0 | 93 | 26 | 61 | 00 | 80 | 54 | 6F | 00 | 02 | 33 | 00 | 03 | 10 | 93 | 28 | 61 |
| 4300 | 00 | 93 | 1C | 6F | 00 | 93 | 1E | 61 | 00 | A0 | 08 | 6F | 00 | 02 | 33 | 10 |
| 4310 | 03 | 10 | 93 | 2A | 7C | 05 | 65 | 09 | 92 | 8C | 63 | 0E | 92 | 8C | 5F | 00 |
| 4320 | 22 | 42 | 02 | 33 | 20 | 03 | 10 | 5E | 08 | 32 | 7A | 00 | 1A | 04 | 01 | 08 |
| 4330 | 26 | 00 | 0E | 03 | F0 | 08 | 3B | 02 | 33 | 30 | 03 | 10 | 00 | 04 | 04 | E2 |
| 4340 | 09 | 39 | 00 | 05 | 33 | 82 | 09 | 59 | 00 | 04 | 33 | 87 | 02 | 33 | 40 | 03 |
| 4350 | 10 | 08 | 99 | 00 | 06 | 33 | 6E | 08 | B9 | 00 | 05 | 33 | 74 | 09 | D9 | 00 |
| 4360 | 05 | 02 | 33 | 50 | 03 | 10 | 33 | 79 | 09 | F9 | 00 | 04 | 33 | 7E | 02 | 77 |
| 4370 | 07 | 02 | 0A | 98 | 00 | 07 | 02 | 33 | 60 | 03 | 10 | 33 | 8B | 0A | BA | 00 |
| 4380 | 02 | 33 | 93 | 0A | 63 | 00 | 13 | 33 | 95 | 13 | 09 | 02 | 33 | 70 | 03 | 10 |
| 4390 | 07 | 0E | 01 | 0C | 0C | 05 | 16 | 05 | 0C | 08 | 05 | 01 | 12 | 14 | 12 | 01 |
| 43A0 | 02 | 33 | 80 | 03 | 10 | 14 | 05 | 05 | 0A | 05 | 03 | 14 | 14 | 09 | 0D | 05 |
| 43B0 | 45 | 3D | 39 | 4B | 4D | 02 | 33 | 90 | 03 | 10 | 4A | 3D | 38 | 3B | 47 | 03 |
| 43C0 | 0F | 00 | 00 | 00 | 03 | 09 | 00 | 00 | 13 | 16 | 02 | 33 | A0 | 03 | 10 | 00 |
| 43D0 | 00 | 13 | 09 | 00 | 00 | 08 | 12 | 21 | 00 | 00 | 1A | 21 | 01 | 00 | 04 | 02 |
| 43E0 | 33 | B0 | 03 | 10 | 21 | 02 | 00 | 01 | 5F | 00 | 2B | 8A | 21 | 00 | 08 | 3B |
| 43F0 | 21 | 01 | 00 | 04 | 02 | 33 | C0 | 03 | 10 | 21 | 02 | 04 | E2 | 5F | 00 | 30 |
| 4400 | 64 | 9E | 08 | 7C | 00 | 01 | 00 | 40 | 00 | 02 | 33 | D0 | 03 | 10 | 4D | 05 |
| 4410 | 64 | 02 | 80 | 00 | 6F | 00 | 64 | 04 | AC | 08 | 6F | 00 | 64 | 04 | 02 | 33 |
| 4420 | E0 | 03 | 10 | AC | 08 | 4D | 05 | 64 | 02 | 00 | 00 | 6F | 03 | 64 | 04 | 7C |
| 4430 | 04 | 9E | 08 | 02 | 33 | F0 | 03 | 10 | 61 | 03 | 80 | 88 | 8D | 28 | 1B | 02 |
| 4440 | 00 | 0F | 0B | 02 | 00 | 07 | E7 | 01 | 02 | 34 | 00 | 03 | 10 | A9 | 30 | 0B |
| 4450 | 03 | 00 | 00 | ED | 02 | 21 | 03 | 00 | 00 | 61 | 04 | 93 | 02 | 02 | 34 | 10 |
| 4460 | 03 | 10 | 6D | 03 | 92 | FE | 41 | 03 | 92 | FE | 03 | 43 | 6D | 03 | 92 | FE |

```
4470 2F 43 02 34 20 03 10 A9 41 0B 04 93 1A E3 02 21
4480 04 93 04 6F 04 93 02 02 34 30 03 10 69 00 93 00
4490 4D 01 80 8A 2E E0 E7 06 67 0D 80 90 02 34 40 03
44A0 10 E6 03 63 0D 80 90 E8 17 65 0D 80 90 0B 03 00
44B0 3B 02 34 50 03 10 E3 02 21 03 00 3B 21 08 00 3B
44C0 83 38 B3 89 FF FE 02 34 60 03 10 B3 89 00 05 01
44D0 08 08 77 A1 39 07 09 00 03 01 09 02 34 70 03 10
44E0 00 BC 5F 00 34 78 9E 08 8D 38 21 0D 92 9E 97 D0
44F0 02 34 80 03 10 5F 00 30 7C 0B 0D 92 CC E3 FA 21
4500 0D 92 9E 2B D0 02 34 90 03 10 A9 D1 0B 0D 92 CC
4510 E3 FB 69 01 92 9C 4D 01 92 9C 02 34 A0 03 10 92
4520 CC E3 03 4D 05 92 9C 92 9E 61 0D 92 9C 2F D8 02
4530 34 B0 03 10 01 00 00 30 2F D9 03 0D 00 18 0B 0D
4540 92 CE EF 06 02 34 C0 03 10 21 0C 92 CE 83 DC 21
4550 0D 92 FE 83 CD 21 09 0B 09 02 34 D0 03 10 00 00
4560 E6 03 01 09 00 08 2F D9 21 0C 92 CE 21 0D 02 34
4570 E0 03 10 92 9E 97 D0 97 C3 5F 00 30 7C 0B 0D 92
4580 CC E3 F9 02 34 F0 03 02 9E 08 02 34 F2 03 10 A7
4590 10 EE 02 A1 93 E8 01 A1 83 5F 00 30 7C 01 00 02
45A0 35 02 03 10 00 20 F1 8A 9E 08 61 02 89 CE 81 20
45B0 01 00 89 D0 02 35 12 03 10 A1 04 21 43 25 01 03
45C0 00 2F 43 AB 10 9E 08 5F 00 02 35 22 03 10 30 7C
45D0 A9 00 AD 43 5F 00 30 7C A9 00 AD 43 AD 53 02 35
45E0 32 03 0E 5F 00 30 7C A9 00 AD 53 F6 8E 9E 08 9E
45F0 08 00 00 1A 1A 1A 1A 1A 1A 1A 1A 1A 1A 1A 1A 1A

A>

CPU 322
0000 01 01 20 02 00 00 03 10 00 00 40 00 01 20 00 00
0010 16 E3 2D C7 5B 8E 00 00 02 00 10 03 0E 00 31 00
0020 62 00 C3 00 00 04 00 02 00 01 00 02 01 00 03 10
0030 00 00 00 00 40 00 01 20 40 00 01 20 40 00 01 20
0040 02 01 10 03 10 40 00 01 20 40 00 01 20 40 00 01
0050 20 40 00 01 20 02 01 20 03 10 21 00 01 00 7D 0D
0060 8D 08 7D 0B 21 0F 8F FE 7D FF 02 01 30 03 10 21
0070 01 90 00 0D 18 AB 11 08 01 80 00 EF FB 4D 05 02
0080 01 40 03 10 78 00 00 01 4D 05 80 38 00 01 4D 05
0090 80 14 00 30 02 01 50 03 10 4D 05 80 40 00 30 4D
00A0 05 80 8E 80 90 4D 05 80 6C 02 01 60 03 10 80 6E
00B0 4D 05 80 4A 80 4C 4D 05 80 A2 80 A4 4D 05 02 01
00C0 70 03 10 80 FE 81 00 4D 05 81 1C 81 1E 4D 05 80
00D0 FC 00 0C 02 01 80 03 10 4D 05 80 42 00 00 61 00
00E0 80 14 6F 00 80 A0 21 0E 02 01 90 03 10 82 40 5F
00F0 00 08 96 67 00 80 02 E6 0C 5F 00 0A 18 02 01 A0
0100 03 10 69 00 80 3E 67 05 80 02 E6 14 63 00 80 02
0110 4D 08 02 01 B0 03 10 80 3E E8 0F 5F 00 08 DE 69
0120 00 80 3C 67 06 80 02 02 01 C0 03 10 E6 08 65 00
0130 80 02 69 00 80 04 4D 08 80 06 4D 08 02 01 D0 03
0140 10 80 3C 4D 05 60 00 80 90 61 01 60 02 61 01 60
0150 02 02 01 E0 03 10 07 01 00 09 5E 06 04 88 69 00
0160 80 00 61 08 80 38 02 01 F0 03 10 B3 89 00 01 61
0170 09 80 00 4B 89 00 0E EE 52 4D 08 02 02 00 03 10
0180 80 00 5F 00 0A 54 69 00 80 06 4D 01 80 06 00 05
0190 02 02 10 03 10 E1 48 4D 08 80 04 4D 08 80 06 4D
```

```
01A0  01 80 3C 00 C8 02 02 20 03 10 E2 15 61 05 80 40
01B0  B3 59 FF FF 6F 05 80 40 4D 01 02 02 30 03 10 80
01C0  40 00 00 EE 03 4D 05 80 40 00 01 61 04 80 14 02
01D0  02 40 03 10 43 04 80 40 6F 04 80 14 4D 08 80 3C
01E0  4D 01 80 3E 02 02 50 03 10 00 C8 E2 15 61 05 80
01F0  40 B3 59 FF FF 6F 05 80 40 02 02 60 03 10 4D 01
0200  80 40 00 00 EE 03 4D 05 80 40 00 01 61 04 02 02
0210  70 03 10 80 14 41 04 80 40 6F 04 80 14 4D 08 80
0220  3E 4D 01 02 02 80 03 10 80 14 00 60 EA 04 4D 01
0230  80 14 00 00 E9 0A 4D 05 02 02 90 03 10 80 14 00
0240  30 4D 05 80 40 00 30 4D 08 80 3E 4D 08 02 02 A0
0250  03 10 80 3C 4D 01 80 04 00 05 E9 04 21 0E 82 40
0260  5E 08 02 02 B0 03 10 01 80 65 0E 80 02 65 0A 80
0270  02 65 0F 80 3A 4D 05 02 02 C0 03 10 60 00 A0 0C
0280  61 01 60 02 8D 14 EE 02 21 01 00 0C 02 02 D0 03
0290  10 6F 01 80 FC 21 0E 82 40 5F 00 08 96 69 00 80
02A0  08 02 02 E0 03 10 69 00 80 00 61 08 80 38 B3 89
02B0  00 01 61 09 80 00 02 02 F0 03 10 4B 89 00 0E E7
02C0  09 4D 08 80 00 69 00 80 06 4D 01 02 03 00 03 10
02D0  80 06 00 05 5E 09 01 20 67 00 80 02 5E 0E 07 52
02E0  02 03 10 03 10 67 01 80 02 5E 0E 06 4E 67 0D 80
02F0  02 EE 0C 67 08 02 03 20 03 10 78 06 EE 09 67 0F
0300  70 06 E6 06 65 0D 80 02 61 0E 02 03 30 03 10 80
0310  08 6F 0E 80 F8 5F 00 08 DE 67 06 80 02 E6 18 02
0320  03 40 03 10 65 00 80 02 4D 08 80 06 61 01 80 08
0330  21 03 00 0C 02 03 50 03 10 61 02 80 4A AB 21 0B
0340  02 80 4C EF 02 21 02 80 6A 02 03 60 03 10 0D 21
0350  00 00 E6 02 AB 10 F3 8B A9 10 6F 01 80 F6 02 03
0360  70 03 10 67 01 80 02 E6 7E 4D 01 80 12 00 02 5E
0370  06 04 A0 02 03 80 03 10 4D 01 80 12 00 01 EE 75
0380  61 09 80 A2 01 09 00 30 02 03 90 03 10 8D B8 21
0390  00 00 0C 61 01 80 FC 8D 38 01 9B AB 10 02 03 A0
03A0  03 10 8D 14 E5 01 01 93 AB 91 0B 09 80 D4 EF 02
03B0  21 09 02 03 B0 03 10 80 EA F0 8C 8D A8 1B 0A 00
03C0  0C 0B 0A 00 06 E7 01 02 03 C0 03 10 A9 B0 61 01
03D0  80 FC 8D 28 9B 12 B3 19 FF FF 8B 12 02 03 D0 03
03E0  10 E7 01 A9 30 A1 3D 61 0E 80 38 0B 0E 00 03 EE
03F0  01 02 03 E0 03 10 A9 E0 99 EC 19 0C 0B FD 1B 0C
0400  00 0A 0B 0C 00 05 02 03 F0 03 10 E7 01 A9 D0 6F
0410  0D 80 EC 0B 0B 00 14 E3 1A 4D 01 02 04 00 03 10
0420  80 38 00 03 EF 36 69 00 80 38 21 0A 00 0B 61 09
0430  02 04 10 03 10 80 A2 01 09 00 30 8D D8 21 9C B3
0440  C9 FF FF B5 DC 02 04 20 03 10 2F 9C AB 91 0B 09
0450  80 D4 EF 02 21 09 80 EA FA 8C 02 04 30 03 10 E8
0460  1A 0B 0B 00 08 EF 1D 4D 01 80 38 00 01 E3 19 02
0470  04 40 03 10 6B 00 80 38 21 0A 00 0B 61 09 80 A2
0480  01 09 00 30 02 04 50 03 10 21 9C B3 C9 00 01 2F
0490  9C AB 91 0B 09 80 D4 EF 02 02 04 60 03 10 21 09
04A0  80 EA FA 8B 61 00 80 38 6F 00 78 00 65 0B 02 04
04B0  70 03 10 80 02 4D 05 60 00 80 90 61 01 60 02 61
04C0  01 60 02 02 04 80 03 10 07 01 00 09 5E 0E 02 D4
04D0  4D 05 78 00 00 00 61 01 02 04 90 03 10 60 02 61
04E0  01 60 02 07 01 00 09 E6 F6 5E 08 01 20 02 04 A0
04F0  03 10 61 09 80 A2 31 97 00 18 8D B8 67 0C 80 02
0500  65 0C 02 04 B0 03 10 80 02 E6 7B A1 73 61 04 81
```

```
0510 1C A1 41 43 01 80 FC 02 04 C0 03 10 43 01 80 FC
0520 0B 01 81 1E EF 06 21 00 81 1E 83 10 02 04 D0 03
0530 10 21 01 81 36 83 01 43 03 80 F6 6F 03 81 38 61
0540 03 02 04 E0 03 10 80 F6 43 03 80 F8 6F 03 81 70
0550 61 03 80 FA 43 03 02 04 F0 03 10 80 F6 6F 03 81
0560 54 61 03 81 36 03 13 41 03 81 38 02 05 00 03 10
0570 6F 03 81 36 61 03 81 6E 31 15 00 30 83 53 41 03
0580 02 05 10 03 10 81 70 6F 03 81 6E 61 03 81 52 31
0590 15 00 1C 83 53 02 05 20 03 10 41 03 81 54 6F 03
05A0 81 52 61 03 81 38 2F 43 61 03 02 05 30 03 10 81
05B0 70 33 43 00 38 61 03 81 54 33 43 00 1C A9 41 02
05C0 05 40 03 10 0B 04 81 34 E3 02 21 04 81 1E 6F 04
05D0 81 1C 61 01 02 05 50 03 10 80 FC 19 00 00 64 A1
05E0 10 B3 19 FF FF 61 04 80 38 02 05 60 03 10 B3 49
05F0 00 01 61 45 00 16 61 03 81 36 99 52 9B 02 02 05
0600 70 03 10 8B 12 E7 01 A9 30 6F 03 80 F2 61 03 81
0610 6E 99 52 02 05 80 03 10 9B 02 8B 12 E7 01 A9 30
0620 03 03 00 14 8D 34 ED 02 02 05 90 03 10 21 03 00
0630 00 6F 03 80 F4 61 03 81 52 99 52 9B 02 02 05 A0
0640 03 10 8B 12 E7 01 A9 30 6F 03 80 F0 61 03 80 FC
0650 67 0B 02 05 B0 03 10 80 02 E6 05 63 0B 80 02 0D
0660 95 00 00 E8 40 01 9B 02 05 C0 03 10 0D 91 00 00
0670 E6 3C AB 91 0B 09 80 A4 EF 02 21 09 02 05 D0 03
0680 10 80 BA F3 8B 8D A8 5B 0A 80 FC 61 03 80 FC B3
0690 39 02 05 E0 03 10 FF FF 8B 3A E7 01 A9 B0 6F 0B
06A0 80 2A 61 09 80 A2 02 05 F0 03 10 61 0A 80 FC B3
06B0 A9 00 01 AB A1 8D A4 EE 01 A9 A1 02 06 00 03 10
06C0 83 A9 0B 09 80 A4 EF 06 21 0B 80 A4 83 9B 21 09
06D0 02 06 10 03 10 80 BC 83 B9 31 9C 00 18 83 C7 B3
06E0 A9 FF FF A1 A5 02 06 20 03 10 61 08 80 38 B3 89
06F0 00 01 59 84 00 06 9B 74 B3 79 02 06 30 03 10 FF
0700 FF 8B 74 E7 01 A9 50 6F 05 80 10 E8 04 4D 08 02
0710 06 40 03 10 80 2A 4D 08 80 10 5F 00 0A 54 5E 08
0720 04 72 4D 05 02 06 50 03 10 80 2C 00 20 69 00 80
0730 12 4D 01 80 12 00 04 E7 6E 02 06 60 03 10 21 0C
0740 82 2E 21 0D 82 0C 8D 18 01 D1 A9 D1 8B CD 02 06
0750 70 03 10 E3 FC 8D 08 19 00 00 09 1B 00 00 24 0B
0760 00 00 12 02 06 80 03 10 E3 01 A9 10 8D 08 56 00
0770 80 16 5D 00 80 16 69 00 02 06 90 03 10 80 1A 4D
0780 01 80 38 00 01 EE 06 4D 01 80 1A 00 08 02 06 A0
0790 03 10 5E 01 03 70 E8 05 4D 01 80 1A 00 10 5E 01
07A0 03 70 02 06 B0 03 10 54 02 80 16 14 08 00 00 00
07B0 00 5D 08 80 16 5B 02 02 06 C0 03 10 80 1A 61 09
07C0 80 1A B3 99 FF FF 4D 08 80 1A 8B 92 02 06 D0 03
07D0 10 E7 01 A9 30 67 0A 80 02 E6 0A 21 08 80 90 2F
07E0 83 02 06 E0 03 10 A9 81 0B 08 80 9E E3 FB 63 0A
07F0 80 02 E8 1B 61 06 02 06 F0 03 10 80 8E 2F 63 A9
0800 61 0B 06 80 9E E3 02 21 06 80 90 02 07 00 03 10
0810 6F 06 80 8E 21 06 80 90 14 02 00 00 00 00 01 63
0820 02 07 10 03 10 A9 61 0B 06 80 9E E3 FB 1B 02 00
0830 08 0B 02 00 04 02 07 20 03 10 E3 01 A9 30 6F 03
0840 80 14 63 01 80 02 4D 08 80 12 02 07 30 03 10 4D
0850 08 80 2C 4D 08 80 1C 5E 08 03 70 4D 01 80 12 02
0860 07 40 03 10 00 03 5E 0E 03 70 5F 00 0A 32 63 0D
0870 80 02 5E 08 02 07 50 03 10 03 70 5F 00 09 1E 4B
```

```
0880  00 80 1C E2 08 6F 00 80 1C 02 07 60 03 10 6F 00
0890  F1 00 61 0D 80 08 6F 0D 80 FA 69 00 80 1E 02 07
08A0  70 03 10 61 01 80 1C 41 01 80 1C 41 01 80 1C B3
08B0  19 FF FD 02 07 80 03 10 8D 28 B5 21 A1 12 81 21
08C0  81 21 8D 38 21 02 00 03 02 07 90 03 10 61 04 80
08D0  4A AB 41 0B 04 80 4C EF 02 21 04 80 6A 02 07 A0
08E0  03 10 01 43 F2 88 8B 31 E3 66 8D 28 69 01 80 A2
08F0  4D 01 02 07 B0 03 10 80 A2 80 BA E3 03 4D 05 80
0900  A2 80 A4 61 08 80 A2 02 07 C0 03 10 61 09 80 20
0910  2F 89 61 09 80 08 33 89 00 18 61 09 02 07 D0 03
0920  10 80 1C 33 89 00 30 61 05 80 20 6F 05 80 26 4D
0930  08 02 07 E0 03 10 80 20 4D 08 80 1C 4D 08 80 1E
0940  63 00 80 02 65 01 02 07 F0 03 10 80 02 61 07 80
0950  FE A1 71 43 01 80 FC 43 01 80 FC 02 08 00 03 10
0960  0B 01 81 00 EF 06 21 00 81 00 83 10 21 01 81 18
0970  02 08 10 03 10 83 01 61 0B 81 1A 61 08 80 38 AB
0980  00 B3 DB 08 00 02 08 20 03 10 8D A8 18 08 00 01
0990  24 AB 1A 08 00 00 27 10 0B 09 02 08 30 03 10 13
09A0  88 E7 01 A9 B0 21 12 2D 7B 6D 0B 81 18 83 2B 02
09B0  08 40 03 10 01 7B 6F 0B 81 18 A9 71 0B 07 81 16
09C0  E3 02 21 07 02 08 50 03 10 81 00 6F 07 80 FE 8D
09D0  A8 61 00 80 FC 9B 0A B3 09 02 08 60 03 10 FF FF
09E0  8D 0A E7 01 A9 B0 6F 0B 80 EE 4D 08 81 1A 02 08
09F0  70 03 10 5E 08 03 70 61 09 80 1E 61 08 80 38 B3
0A00  89 00 01 02 08 80 03 10 4B 89 00 0E EF 91 41 00
0A10  80 20 6F 00 80 20 63 05 02 08 90 03 10 80 02 5F
0A20  08 03 70 21 0D 78 02 21 0B 78 00 67 00 02 08 A0
0A30  03 10 78 00 EE FD 54 00 78 02 67 00 78 00 E6 FD
0A40  21 0C 02 08 B0 03 10 80 01 07 BC 9E 06 ED FB 14
0A50  D0 8D 02 ED 01 8D 02 02 08 C0 03 10 8D 12 ED 01
0A60  8D 12 A1 02 A1 13 B3 25 FF FF A3 3F 02 08 D0 03
0A70  10 81 30 81 21 8B 10 ED 01 A1 10 93 E0 E8 E8 5F
0A80  00 02 08 E0 03 10 09 1E 4B 00 80 1C E3 08 6F 00
0A90  80 1C 6F 00 F1 00 02 08 F0 03 10 61 0D 80 08 6F
0AA0  0D 80 FA 61 06 80 48 6F 06 80 20 02 09 00 03 10
0AB0  4D 01 80 48 00 48 E7 06 65 06 80 02 4D 05 80 2C
0AC0  02 09 10 03 10 00 40 9E 08 63 06 80 02 4D 08 80
0AD0  20 9E 08 21 00 02 09 20 03 10 00 1F 21 03 82 00
0AE0  61 01 80 14 0B 31 E7 06 A9 31 02 09 30 03 10 AB
0AF0  00 0B 00 00 03 EA F9 8D 08 61 01 80 6C 2F 10 02
0B00  09 40 03 10 A1 14 A9 11 0B 01 80 8C E3 02 21 01
0B10  80 6E 14 02 02 09 50 03 10 00 00 00 00 6F 01 80
0B20  6C 21 06 00 02 61 05 80 38 02 09 60 03 10 B3 63
0B30  05 00 A1 65 01 43 AB 41 0B 04 80 6E EF 02 02 09
0B40  70 03 10 21 04 80 8C AB 60 EE F7 9B 52 B3 59 FF
0B50  FF 8B 52 02 09 80 03 10 E7 01 A9 30 0B 03 00 03
0B60  EA 01 8D 38 6D 03 80 48 02 09 90 03 10 41 03 80
0B70  48 6D 03 80 48 61 01 80 4A 2D 13 A9 17 02 09 A0
0B80  03 10 0B 01 80 6A E3 04 03 01 80 6A 01 01 80 4A
0B90  21 13 02 09 B0 03 10 6D 03 80 48 43 03 80 48 6F
0BA0  03 80 48 61 01 80 4A 02 09 C0 03 10 21 13 A9 11
0BB0  0B 01 80 6A E3 02 21 01 80 4C 6F 01 02 09 D0 03
0BC0  10 80 4A 6F 03 F0 02 6F 00 F0 00 A1 30 61 0A 80
0BD0  4A 02 09 E0 03 10 4D 01 80 38 00 03 E6 0E 4D 01
0BE0  80 38 00 02 E6 01 02 09 F0 03 10 A9 A7 A9 A7 A9
```

```
0BF0  A5 0B 0A 80 6A E3 04 03 0A 80 6A 02 0A 00 03 10
0C00  01 0A 80 4A A1 0C 03 AC ED 01 8D C8 4D 0C 81 1A
0C10  02 0A 10 03 10 E3 02 6F 0C 81 1A 9E 08 5F 00 09
0C20  1E 63 05 80 02 02 0A 20 03 10 4D 01 80 48 00 48
0C30  9E 09 65 05 80 02 5F 00 0A 32 02 0A 30 03 10 9E
0C40  08 21 01 80 6E 0D 18 A9 11 0B 01 80 8C E3 FB 02
0C50  0A 40 03 10 21 01 80 4C 0D 18 A9 11 0B 01 80 6A
0C60  E3 FB 4D 08 02 0A 50 03 10 80 48 9E 08 61 01 80
0C70  3A 4D 05 60 00 91 B2 6F 01 02 0A 60 03 10 60 02
0C80  61 01 80 10 19 00 00 64 4D 05 60 00 80 8A 02 0A
0C90  70 03 10 6F 01 60 02 61 01 80 26 4D 05 60 00 80
0CA0  88 6F 01 02 0A 80 03 10 60 02 61 01 80 2A 4D 05
0CB0  60 00 80 86 6F 01 60 02 02 0A 90 03 10 61 01 80
0CC0  38 4D 05 60 00 A0 00 6F 01 60 02 61 01 02 0A A0
0CD0  03 10 80 EC 4D 05 60 00 A0 02 6F 01 60 02 61 01
0CE0  80 EE 02 0A B0 03 10 4D 05 60 00 A0 04 6F 01 60
0CF0  02 61 01 80 F0 4D 05 02 0A C0 03 10 60 00 A0 06
0D00  6F 01 60 02 61 01 80 F2 4D 05 60 00 02 0A D0 03
0D10  10 A0 08 6F 01 60 02 61 01 80 F4 67 08 78 06 E6
0D20  01 02 0A E0 03 10 8D 18 4D 05 60 00 A0 0A 6F 01
0D30  60 02 61 01 60 04 02 0A F0 03 10 9E 08 8D 07 7A
0D40  00 8D 07 7A 00 8D 07 7A 00 8D 07 02 0B 00 03 0E
0D50  7A 00 8D 07 7A 00 8D 07 7A 00 8D 07 7A 00 00 00
0D60  1A 1A 1A 1A 1A 1A 1A 1A 1A 1A 1A 1A 1A 1A 1A 1A
0D70  1A 1A 1A 1A 1A 1A 1A 1A 1A 1A 1A 1A 1A 1A 1A 1A
0D80  1A 1A 1A 1A 1A 1A 1A 1A 1A 1A 1A 1A 1A 1A 1A 1A
0D90  1A 1A 1A 1A 1A 1A 1A 1A 1A 1A 1A 1A 1A 1A 1A 1A
0DA0  1A 1A 1A 1A 1A 1A 1A 1A 1A 1A 1A 1A 1A 1A 1A 1A
0DB0  1A 1A 1A 1A 1A 1A 1A 1A 1A 1A 1A 1A 1A 1A 1A 1A
0DC0  1A 1A 1A 1A 1A 1A 1A 1A 1A 1A 1A 1A 1A 1A 1A 1A
0DD0  1A 1A 1A 1A 1A 1A 1A 1A 1A 1A 1A 1A 1A 1A 1A 1A
0DE0  1A 1A 1A 1A 1A 1A 1A 1A 1A 1A 1A 1A 1A 1A 1A 1A
0DF0  1A 1A 1A 1A 1A 1A 1A 1A 1A 1A 1A 1A 1A 1A 1A 1A
```

What is claimed is:

1. A method for the noninvasive measurement of cardiac output of a mammalian patient on a real time, beat-by-beat basis as a combined function of the cross-sectional area of the ascending aorta and the systolic velocity of blood flow therethrough, comprising the steps of:

a. pulsedly insonifying the ascending aorta of said patient with repetitive, intermittent ultrasonic energy propagating along a line generally transverse with respect to the axis of said ascending aorta to define a first insonification zone;

b. receiving pulses of ultrasonic energy reflected from anatomical structure within said first insonification zone, including energy reflected from the anterior and posterior walls of said ascending aorta characteristic of the separation thereof along the transverse line of propagation;

c. discriminating said pulses of received ultrasonic energy to detect the transverse dimension of said ascending aorta between said anterior and posterior walls thereof;

d. developing an aortic diameter signal proportional to and indicative of said transverse dimension;

e. computing the cross-sectional area of said ascending aorta in the plane of said transverse line of propagation of pulsed energy;

f. continuously insonifying said ascending aorta with uninterrupted ultrasonic energy propagating along a line generally axial with respect to the axis of said ascending aorta to define a second insonification zone;

g. receiving Doppler-shifted ultrasonic energy reflected from pulsatile blood flow through said ascending aorta, frequency-shifted from said uninterrupted ultrasonic energy by values characteristic of systolic velocity of said blood flow;

h. developing a systolic velocity energy signal proportional to and indicative of said systolic velocity;

i. subjecting said systolic velocity energy signal to frequency spectrum analysis at a predetermined signal sampling rate to yield a velocity component profile signal;

j. integrating said velocity component profile signal over time for each period of said pulsatile flow to calculate a systolic velocity integral;

k. computing systolic volume as a combined function of said cross-sectional area and said systolic velocity integral;

l. computing cardiac output as the sum of said systolic volumes for n periods and dividing the sum by the time duration thereof.

2. The method of claim 1, wherein said step of subjecting said systolic velocity energy signal to frequency spectrum analysis includes the steps of:
   a. establishing a plurality of signal sampling rates;
   b. establishing a plurality of statistically anticipated systolic velocity ranges for pulsatile blood flow;
   c. selecting high and low threshold values for said ranges;
   d. monitoring systolic velocity to determine its value within a given one of said ranges relative to said threshold values; and,
   e. adjusting said signal sampling rate to a predetermined one of said plurality corresponding to the value of said systolic velocity within the high and low threshold values for said predetermined range.

3. The method of claim 2, further comprising the step of providing an operator-interactive visual display for presenting a visual sequence of procedural operator options, including the step of measuring said aortic diameter by:
   a. locating a pulse-echo ultrasonic transducer probe to establish said first insonification zone through said patient's cardiac window;
   b. presenting a scaled visual display of said received ultrasonic energy indicative of the anatomical structure within said insonification zone including said anterior and posterior walls of said ascending aorta;
   c. measuring the scaled dimension between said walls to develop said transverse aortic signal; and
   d. delivering said transverse aortic signal to processor means for computing said cross-sectional area in accordance with an adaptive algorithm stored therein.

4. The method of claim 3, further comprising the step of manipulating said probe to minimize the scaled distance between said walls and returns from structure other than said walls appearing on said visual display.

5. The method of claim 4, wherein said measuring step includes:
   a. visually discriminating the returns corresponding respectively to said anterior and posterior walls for the correct cross section of said aorta;
   b. positioning a first moveable visual marker over said return for said anterior wall;
   c. positioning a second moveable visual marker over said return for said posterior wall; and,
   d. measuring the scaled distance between said first and second markers.

6. The method of claim 5, wherein said display is a cathode ray tube display and said presenting step includes:
   a. amplifying received pulse-echo signals indicative of returned ultrasonic energy from said first insonification zone;
   b. selectively attenuating said pulse-echo signals inversely proportional to the propagation distance between said probe and the structure within said first insonification zone responsible for a given return to spatially normalize said pulse-echo signals;
   c. digitizing the normalized pulse-echo signals to develop digital raster scan signals; and,
   d. controlling raster scan of said cathode ray tube with said digital raster scan signals to present said visual display.

7. The method of claim 6, wherein said display includes a touch-sensitive overlay for operator interaction, whereby said sequence of procedural operator options are elected upon a manual touch of active field areas of said overlay.

8. The method of claim 3, further comprising the steps of providing a continuous wave transducer probe having a transmitter crystal for developing said uninterrupted ultrasonic energy at a transmitter frequency and a receiver crystal for detecting received, Doppler-shifted energy from said second insonification zone having a frequency shift proportional to said systolic velocity, and converting said received energy to a Doppler signal, wherein said step of developing said systolic velocity energy signal comprises the steps of:
   a. amplifying said Doppler signal;
   b. mixing said Doppler signal with at least one reference signal having a reference frequency selected to develop an audio frequency Doppler signal; and,
   c. digitizing said audio frequency Doppler signal and applying same to said frequency spectrum analysis.

9. The method of claim 8, wherein said mixing step includes the steps of:
   a. selectively attenuating said Doppler signal to develop an amplitude normalized RF Doppler signal;
   b. mixing said normalized RF Doppler signal with a first reference frequency signal having a frequency different from said transmitter frequency by a frequency f to develop an intermediate frequency Doppler signal;
   c. selectively attenuating said intermediate frequency Doppler signal to develop an amplitude normalized intermediate frequency Doppler signal; and,
   d. mixing said normalized intermediate frequency Doppler signal with a second reference frequency signal having a frequency f to develop an audio frequency Doppler signal having a frequency directly proportional to systolic velocity, constituting said systolic velocity energy signal.

10. The method of claim 9, wherein said step of subjecting said systolic velocity energy signal to frequency spectrum analysis includes:
    a. sampling said systolic velocity energy signal at a first of said signal sampling rates to develop a sampled systolic velocity energy signal;
    b. digitizing said sampled systolic velocity energy signal;
    c. subjecting the digitized systolic velocity energy signals to fast Fourier transformation; and,
    d. selecting the peak component frequency in each sampling period to develop said velocity component profile signal.

11. The method of claim 10, wherein said step of establishing a plurality of signal sampling rates includes establishing a first range for systolic velocities up to about 82 cm/s, a second range for systolic velocities up to about 165 cm/s and a third range for systolic velocities up to about 330 cm/sec.; and further wherein said step of adjusting said signal sampling rate comprises:
    a. initially sampling at a first rate corresponding to said first range;
    b. monitoring said velocity component profile signal for a predetermined number of cardiac cycles to determine systolic velocity;
    c. comparing systolic velocity to a high threshold value for said first range;
    d. adjusting said sampling rate to a second rate corresponding to said second range upon the occurrence of systolic velocities in excess of the high threshold value for said first range;

e. comparing systolic velocity ot a high and low threshold values for said second range;

f. adjusting said sampling rate to said first rate upon the occurrence of systolic velocities lower than the low threshold value for said second range or to said third rate upon the occurrence of systolic velocities in excess of said high threshold value for said second range;

g. comparing systolic velocity to a low threshold value for said third range; and, h. adjusting said sampling rate to said second rate upon the occurrence of systolic velocities lower than said low threshold value for said third range.

12. The method of claim 11, wherein said velocity component profile signal is applied to processor means for computing the time integral of each of said signals over the corresponding cardiac period to yield said systolic velocity integral and for computing cardiac stroke volume as the product of said systolic velocity integral and said aortic cross-sectional area.

13. The method of claim 12, further comprising the step of visually displaying said systolic velocity integral on a cathode ray tube display.

14. The method of claim 13, further comprising the steps of manipulating said continuous wave transducer probe to maximize the value of the displayed systolic velocity integral.

15. The method of claim 14, wherein said cardiac output is calculated as the average of the sum of discrete stroke volume values based on the sum of cardiac cycle periods.

16. The method of claim 15, further comprising the steps of calculating cardiac index as the ratio of cardiac output to body surface area of said patient and stroke index as the ratio of stroke volume to said body surface area.

17. A system for the noninvasive measurement of cardiac output of a mammalian patient on a real time, beat-by-beat basis as a combined function of the cross-sectional area of the ascending aorta and the systolic velocity of blood flow therethrough, comprising:

a. pulse-echo transducer means for developing repetitive, intermittent bursts of ultrasonic energy and applying same to said patient to define a first insonification zone enveloping the region of the ascending aorta of said patient and for detecting energy reflected from the anatomical structure within said first insonification zone, including the anterior and posterior walls of said ascending aorta;

b. pulse transmitter means for exciting said pulse-echo transducer to develop said bursts of energy;

c. pulse receiver means for developing an echo signal proportional to and indicative of detected energy;

d. operator-interactive visual display means for presenting control and display capabilities, including a graphic, scaled display of echo signals representative of the spatial conformation of said anatomical structure and signal strength representative of pulsatile blood flow therethrough;

e. measurement means in operative association with said visual display means for determining the spatial separation between anterior and posterior walls represented on said scaled display, to develop an aortic diameter signal, f. area processor means receiving said aortic diameter signal for determining the cross-sectional area of said ascending aorta;

g. continuous wave transducer means for developing uninterrupted ultrasonic energy and applying same to define a second insonification zone within said region of said ascending aorta and for detecting Doppler-shifted energy reflected from pulsatile blood flow therethrough;

h. continuous wave transmitter means for exciting said continuous wave transducer to develop said uninterrupted ultrasonic energy at a continuous wave transmitter frequency;

i. continuous wave receiver means for developing a Doppler signal having a frequency shift from said continuous wave transmitter frequency proportional to and indicative of the systolic velocity of said pulsatile blood flow;

j. converter means for processing said Doppler signal to an audio frequency systolic velocity energy signal;

k. spectrum analyzer means receiving said systolic velocity energy signal for developing a frequency domain velocity component profile signal characteristic of the velocity profile of systolic flow over an observed cardiac cycle;

l. velocity processor means receiving said velocity component profile signal for computing the time integral thereof over the period of said caridac cycle, in accordance with an adaptive algorithm stored therein, to yield a systolic velocity integral signal and a stroke volume signal as a function of said cross-sectional area and said stroke volume; and, m. cardiac output processor means receiving said stroke volume signal and a heart rate signal for determining cardiac output as the time-averaged sum of a plurality of cyclic stroke volumes.

18. The system of claim 17, wherein said pulse receiver means comprises:

a. echo amplifier means for developing an amplitude-conditioned radio frequency echo signal;

b. controlled attenuator means for amplitude alteration of said amplitude-conditioned radio frequency echo signal inversely proportional to the propagation distance between said pulse-echo transducer means and the anatomical structure within said first insonification zone responsible for a given return to develop a spatially normalized echo signal;

c. detector means for rectifying and filtering said spatially normalized echo signal to yield an envelope signal proportional to and indicative of said detected energy; and, d. analog-to-digital converter means receiving said envelope signal for developing a digital echo signal output.

19. The system of claim 18, wherein said visual display is a cathode ray tube display; said system further comprising raster scan driving and storage means receiving said digital echo signal for visual presentation of said detected energy on a scaled video display representing said anatomical structure.

20. The system of claim 19, wherein said measurement means is comprised of moveable markers appearing on said display for operator registration with the video display at returns representative of said anterior and posterior walls respectively.

21. The system of claim 20, further comprising touch-sensitive overlay means in operative association with said visual display, wherein said markers are moveable in response to a manual touch of an active field area on said display and said aortic diameter signal is developed as a signal proportional to the distance between said markers when registered with said returns.

22. The system of claim 21, wherein said continuous wave receiver means includes:
   a. Doppler signal amplifier means for developing an amplitude-conditioned radio frequency Doppler signal; and,
   b. mixer means for frequency translation of said Doppler signal to yield a frequency normalized Doppler signal.

23. The system of claim 22, wherein said receiver means includes first and second mixer stages preceded respectively by first and second controlled attenuator means; and further wherein said first mixer stage receives said radio frequency Doppler signal and a beat frequency reference signal having a frequency different from said transmitter frequency by a frequency f to yield an intermediate frequency Doppler signal and said second mixer stage receives said intermediate frequency Doppler signal and a beat frequency reference signal having a frequency f to yield an audio frequency Doppler signal having a frequency profile directly proportional to said systolic velocity.

* * * * *